US011155609B2

United States Patent
Chain et al.

(10) Patent No.: US 11,155,609 B2
(45) Date of Patent: Oct. 26, 2021

(54) ANTI-TAUC3 ANTIBODIES AND USES THEREOF

(71) Applicant: TauC3 Biologics Limited, London (GB)

(72) Inventors: Daniel Chain, New York, NY (US); Preeti Bakrania, Stevenage (GB); Seema Patel, Stevenage (GB)

(73) Assignee: TauC3 Biologies Limited, London (GB)

( * ) Notice: Subject to any disclaimer, the term of this patent is extended or adjusted under 35 U.S.C. 154(b) by 0 days.

(21) Appl. No.: 16/838,235

(22) Filed: Apr. 2, 2020

(65) Prior Publication Data

US 2020/0407431 A1 Dec. 31, 2020

Related U.S. Application Data

(60) Provisional application No. 62/829,774, filed on Apr. 5, 2019.

(51) Int. Cl.
*C07K 16/18* (2006.01)

(52) U.S. Cl.
CPC .......... *C07K 16/18* (2013.01); *C07K 2317/24* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 3,955,137 A | 5/1976 | Harrington et al. |
| 3,978,797 A | 9/1976 | Harrington et al. |
| 4,092,603 A | 5/1978 | Harrington |
| 4,166,817 A | 9/1979 | Ferres et al. |
| 5,492,812 A | 2/1996 | Voohies |
| 5,846,546 A | 12/1998 | Hurwitz et al. |
| 6,232,437 B1 | 5/2001 | Vandermeeren et al. |
| 6,376,205 B1 | 4/2002 | Wischik et al. |
| 6,762,179 B2 | 7/2004 | Cochran et al. |
| 6,953,794 B2 | 10/2005 | Wischik et al. |
| 7,238,788 B2 | 7/2007 | Lee |
| 7,256,190 B2 | 8/2007 | Cochran et al. |
| 7,335,505 B2 | 2/2008 | Wischik et al. |
| 7,335,652 B2 | 2/2008 | Wischik et al. |
| 7,488,727 B2 | 2/2009 | Cochran et al. |
| 7,534,786 B2 | 5/2009 | Wischik et al. |
| 7,605,179 B2 | 10/2009 | Wischik et al. |
| 7,713,962 B2 | 5/2010 | Wischik et al. |
| 7,737,138 B2 | 6/2010 | Wischik et al. |
| 7,741,446 B2 | 6/2010 | Pardridge et al. |
| 7,790,881 B2 | 9/2010 | Storey et al. |
| 7,834,237 B2 | 11/2010 | Wischik et al. |
| 7,901,689 B2 | 3/2011 | Chain |
| 8,012,936 B2 | 9/2011 | Sigurdsson et al. |
| 8,173,127 B2 | 5/2012 | Chain |
| 8,703,137 B2 | 4/2014 | Chain |
| 2002/0086847 A1 | 7/2002 | Chain |
| 2002/0168687 A1 | 11/2002 | Wischik et al. |
| 2003/0194742 A1 | 10/2003 | Vanmechelen |
| 2004/0078835 A1 | 4/2004 | Wischik et al. |
| 2004/0082763 A1 | 4/2004 | Novak |
| 2004/0268425 A1 | 12/2004 | Bookbinder |
| 2005/0075308 A1 | 4/2005 | Wilson |
| 2006/0088548 A1 | 4/2006 | Chain |
| 2006/0167227 A1 | 7/2006 | Kontsekova |
| 2007/0166311 A1 | 7/2007 | Greferath |
| 2008/0050383 A1 | 2/2008 | Sigurdsson et al. |
| 2008/0125347 A1 | 5/2008 | Grabstein |
| 2008/0207603 A1 | 8/2008 | Storey et al. |
| 2008/0207604 A1 | 8/2008 | Wischik et al. |
| 2008/0219929 A1 | 9/2008 | Wischik et al. |
| 2008/0220449 A1 | 9/2008 | Vasan |
| 2009/0054419 A1 | 2/2009 | Wischik et al. |
| 2009/0075984 A1 | 3/2009 | Wischik et al. |
| 2009/0093002 A1 | 4/2009 | Pfeifer |
| 2009/0123936 A1 | 5/2009 | Novak |
| 2009/0155249 A1 | 6/2009 | Pfeifer |
| 2009/0209526 A1 | 8/2009 | Wischik et al. |
| 2009/0258031 A1 | 10/2009 | Karrer |
| 2010/0015095 A1 | 1/2010 | Pan |
| 2010/0280975 A1 | 11/2010 | Wischik et al. |
| 2010/0285605 A1 | 11/2010 | Wischik et al. |
| 2010/0290986 A1 | 11/2010 | Wischik et al. |
| 2010/0316564 A1 | 12/2010 | Sigurdsson |
| 2011/0142824 A1 | 6/2011 | Burbridge et al. |
| 2011/0177109 A1 | 7/2011 | Smith, III et al. |
| 2012/0087861 A1 | 4/2012 | Nitsch et al. |

(Continued)

FOREIGN PATENT DOCUMENTS

| | | |
|---|---|---|
| WO | WO 2005/035550 A2 | 4/2005 |
| WO | WO 2009/008725 A2 | 1/2009 |
| WO | WO 2012/045882 | 4/2012 |

(Continued)

OTHER PUBLICATIONS

International Search Report dated Aug. 17, 2012, in connection with International Application PCT/US2012/023375.
Written Opinion of the International Searching Authority dated Aug. 17, 2012, in connection with International Application PCT/US2012/023375.
Sengupta et al., "Degradation of Tau Protein by Puromycin-Sensitive Aminopeptidase in Vitro", Biochemistry, Nov. 24, 2006, vol. 45, pp. 15111-15119.
Gamblin et al., "Caspase cleavage of tau: Linking amyloid and neurofibrillary tangles in Alzheimer's disease", Proceedings of the National Academy of Sciences, Aug. 19, 2003,vol. 100, No. 17, pp. 10032-10037.
Yamamoto et al., "Phosphorylation of tau at serine 416 by Ca2+/calmodulin-dependent protein kinase II in neuronal soma in brain", Journal of Neurochemistry, Jul. 5, 2005, vol. 94, pp. 1438-1447.

(Continued)

*Primary Examiner* — Adam Weidner
(74) *Attorney, Agent, or Firm* — Davidson, Davidson & Kappel, LLC

(57) ABSTRACT

Anti-TauC3 antibodies that are at least several orders of magnitude more specific for TauC3 than for full length tau (2N4R) are described. Also described are methods of using anti-TauC3 antibodies.

20 Claims, 47 Drawing Sheets

Specification includes a Sequence Listing.

(56) References Cited

U.S. PATENT DOCUMENTS

2012/0244159 A1 9/2012 Chain
2020/0079825 A1 3/2020 Takeda et al.

FOREIGN PATENT DOCUMENTS

| WO | WO 2012/149365 | | 11/2012 |
|---|---|---|---|
| WO | WO 2015/031673 | A2 | 3/2015 |
| WO | WO 2015/155694 | A1 | 10/2015 |
| WO | WO 2017/027685 | A2 | 2/2017 |
| WO | WO 2018/007950 | A1 | 1/2018 |
| WO | WO 2020/206093 | A1 | 10/2020 |

OTHER PUBLICATIONS

Vestergaard et al., "Detection of Alzheimer's tau protein using localised surface plasmon resonance-based immunochip", Talanta, Jun. 17, 2007, vol. 74, pp. 1039-1042.
Lars M. Ittner et al., "Amlyiod-B and tau—a toxic pas de deux in Alzheimer's disease", Nature Reviews, NeuroScience, Feb. 2011, vol. 12.
Alix de Calignon et al., "Caspase activation precedes and leads to tangles", vol. 464: 12, Apr. 2, 2010.
B. Kovacech et al., Tau Truncation in a productive Pottranslational Modification of Neurofibrillary Degeneration in Alzheimer's Disease, Current Alzheimer's Research, 2010, pp. 708-716.
"Robert A. Rissman et al., Caspase-cleavage of tau is an early event in Alzheimer disease tangle pathology", The Journal of Clinical Investigation, Jul. 2001, vol. 114, pp. 115-130.
Khurana V, Elson-Schwab I, Fulga TA, Sharp KA, Loewen CA, et al.. Lysosomal Dysfunction Promotes Cleavage and Neurotoxicity of Tau In Vivo. PLoS Genet 6(7): e1001026. doi:10.1371/journal. pgen.1001026, (2010).
Peleg M. Horowitz et al., Early Changes and Capase-6 Cleavage of Tau in Alzheimers Disease, The Journal of Neuroscience, Sep. 8, 2004, vol. 24(36) pp. 7895-7902.
Patrice Delobel et al, "Analysis of Tau Phosphorylation and Truncation in a Mouse Model of Human Tauopathy", Molecular Pathogenesis of Genetic and Inherited Diseases; The American Journal of Pathology, vol. 172, Jan. 2008. pp. 123-131.
Ayodeji A. Asuni et al., "Immunotherapy Targeting Pathological Tau Conformers in a Tangle Mouse Model Reduces Brain Pathology with Associated Functional Improvements", Neurobiology of Disease, The Journal of Neuroscience, Aug. 22, 2007, vol. 27(34), pp. 9115-9129.
Einar M. Sigurdsson, "Tau-Focused Immunotherapy for Alzheimer's Disease and Related Tauopathies", Current Alzheimer Research, Jun. 2009, pp. 446-450.
Einar M.Sigurdsson, "Immunotherapy Tageting Pathological Tau Protein in Alzheimer's Disease and Related Tauopathies", journal of Alzheimer's Disease 15, 2008, pp. 157-168.
F. Incardona et al. 1995 "How much are homologous peptides homologous?" J theor bioi 175:437-455.
Qipeng Zhang et al., Truncated tau at D421 is associated with neurodegeneration and tangle formation in the brain of Alzheimer transgenic models, Acta Neuropathol , 2009. vol. 117, pp. 687-697.
Invitrogen, "Mouse (monoclonal) Anti-tau (421/422) Cleavage Site Specific Antibody, Unconjugated", Product Analysis Sheet. Catalog No. AHB0061, (2010).
Millipore, Anti-cleaved-Tau (Asp421), clone C3, Uniprot No. P10636, Jan. 16, 2011, http://www.millipore.com/catalogue/item/36-017.
Allal Boutajangout et al., Immunotherapy targeting pathological tau prevents cognitive decline in a new tangle mouse model, Journal Section: Neurobiology of Disease, (2010).
Saido 1992 "Autolytic transition of .mu.-calpain upon activation as resolved by antibodies distinguishing between the pre- and post-autolysis forms" J biochem 111 :81-86.
Saido 1993 "Spatial resolution of fodrin proteolysis in postischemic brain" J bio chem 268(33):25239-25243.
Saido 1994 "Spatial resolution of the primary .beta.-amyloidogenic process induced in postischemic hippocampus" J bio chem 269(21 ):15253-15257.
Castillo-Carranza et al. 2013 "Tau aggregates as immunotherapeutic targets" Frontiers in Bioscience 5:426-438.
Delrieu et al. 2012 "Clinical trials in Alzheimer's disease: immunotherapy approaches" J Neurochem 120(Supp 1):186-193.
Rosenmann et al. 2006 "Tauopathy-like Abnormalities and neurologic deficits in mice immunized with neuronal tau protein" Arch Neurol 63:1459-1467.
Harlow and Lane 1988 "Antibodies: A Labratory Manual" Cold Spring Harbor Labratory, Chapter 5, p. 76.
Basurto-Islas et al. 2008 "Accumulation of Aspartic Acid 421 and glutamic acid 391 cleaved tau in neurofibrillary tangles correlates with progression in alzheimer's disease" J neuropathol exp neural 67(5):470-483.
Rafii and Aisen 2009 "recent developments in alzheimer's disease therapeutics" BMC medicine 7(7):1-4.
Nicholls "characterization of tauc3 antibody and demonstration of its potential to block tau propagation" PLOS one 12(5):e0177914 (Year: 2017).
Guillozet-Bongaarts 2005 "tau truncation during neurofibrillary tangle evolution in alzheimer's disease" Neurobiol aging 26:1015-1022.
Declaration of Daniel Chain, dated Mar. 29, 2018.
Chen et al. "Enhancement and destruction of antibody function by somatic mutation: unequal occurrence is controlled by V gene combinatorial associations" the EMBO Journal; vol. 14; No. 12; pp. 2784-2794 (year: 1995).
Kussie et al. "A Single Engineered Amino Acid Substitution Changes Antibody Fine Specificity" J immunol 152(1); pp. 146-152 (year: 1994).
Panza et al. "Beyond the neurotransmitter-focused approach in treating Alzheimer's disease: drugs targeting beta-amyloid and tau protein." Aging Clin Exp Res 21(6): abstract.
International Search Report dated Jul. 9, 2020, in connection with International Application PCT/IB2020/000243.
Written Opinion of the International Searching Authority dated Jul. 9, 2020, in connection with International Application PCT/IB2020/ 000243.
International Search Report dated Sep. 14, 2020, in connection with International Application PCT/US2020/026349.
Written Opinion of the International Searching Authority dated Sep. 14, 2020, in connection with International Application PCT/US/ 2020/026349.
Pacific "What is an epitope" accessed from pacificimmunology.com (Year: 2018).

Figure 1. Protein and DNA sequence of MoTau01 Kappa Light Chain Variable Region

Figure 2. Protein and DNA Sequence of MoTau01 Heavy Chain Variable Region

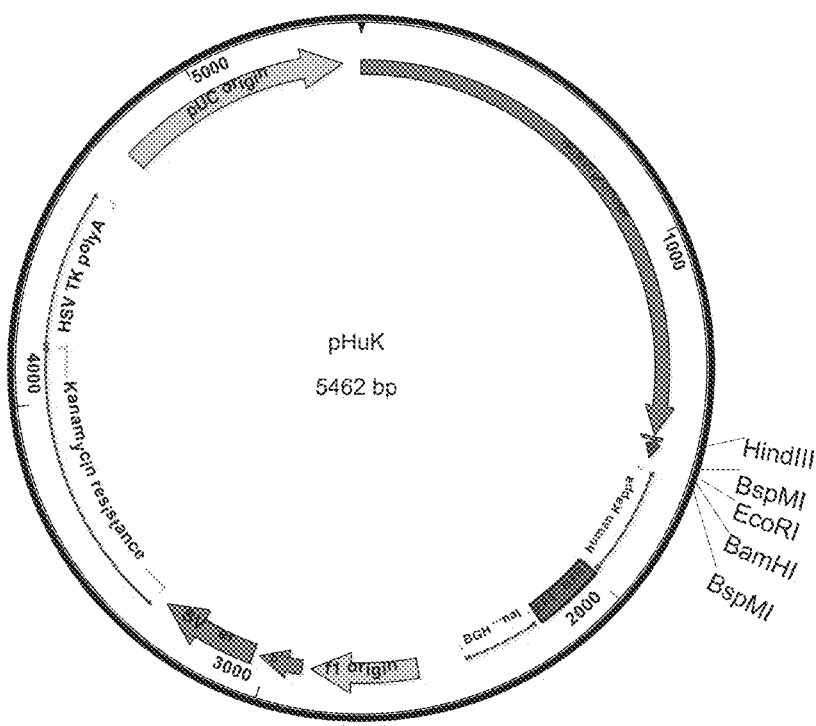
Figure 3. pHuK LIC vector

Figure 4. pHuG4 LIC vector
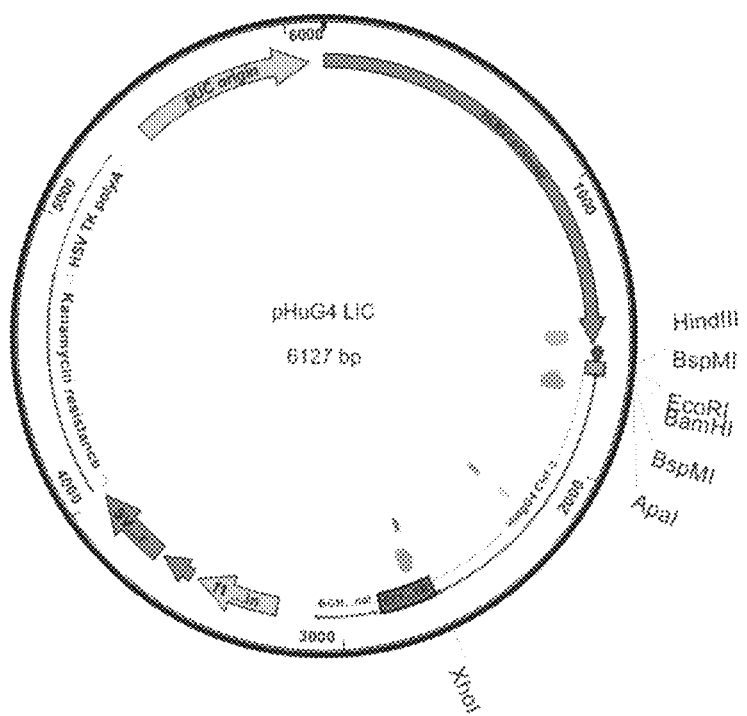

Figure 5. Protein and DNA Sequence of chimeric MoTau01 VK

Figure 6. Protein and DNA Sequence of chimeric MoTau01 VH

Binding test of chimeric Tau01 to TauC3 and FL Tau using binding ELISA

*Binding test of murine and chimeric Tau01 antibodies to TauC3 and FL Tau using the Octet*

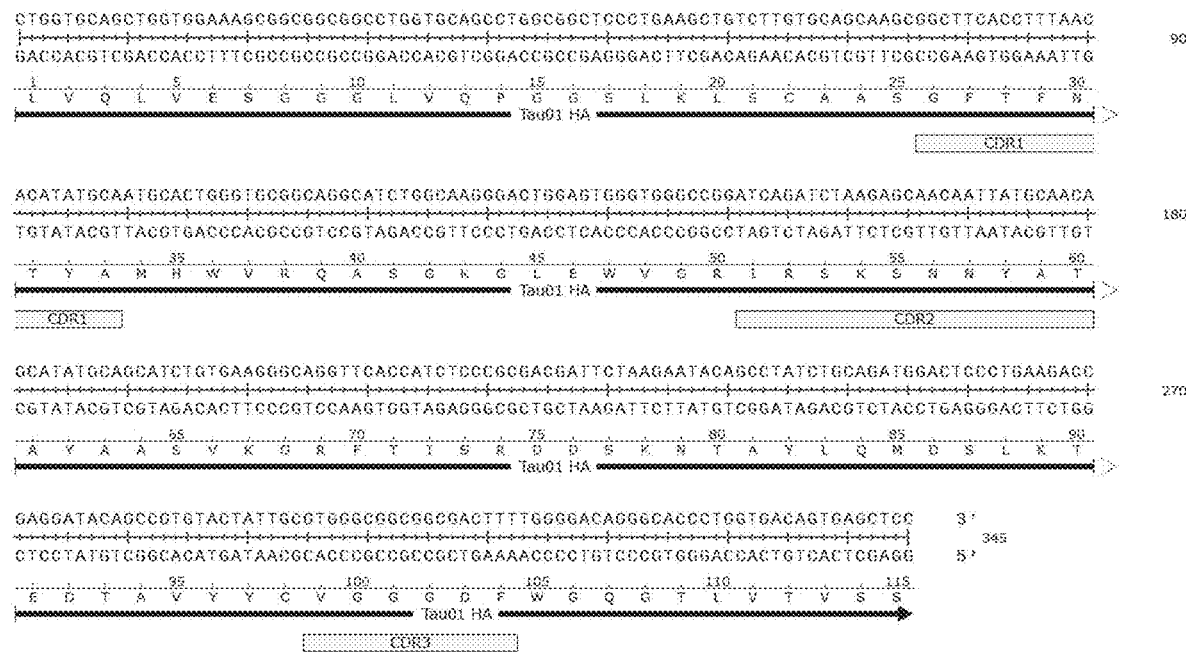
Figure 9. Protein and DNA Sequence of Tau01 HA

Figure 10. Protein and DNA Sequence of Tau01 HB

```
GAGGTGCAGGTGGTGGAAAGCGGCGGCGGCCTGGTGCAGCCTGGCGGCAGCCTGAAGCTGTCCTGTGCAGCATCTGGCTTCACCTTTAAC
|-+-+-+-+-+-+-+-+-+-+-+-+-+-+-+-+-+-+-+-+-+-+-+-+-+-+-+-+-+-+-+-+-+-+-+-+-+-+-+-+-+-+-+-+-|   90
CTCCACGTCCACCACCTTTCGCCGCCGCCGGACCACGTCGGACCGCCGTCGGACTTCGACAGGACACGTCGTAGACCGAAGTGGAAATTG
   1         5              10             15             20             25             30
   E   V   Q   V   V   E   S   G   G   G   L   V   Q   P   G   G   S   L   K   L   S   C   A   A   S   G   F   T   F   N
   >----------------------------------------- Tau01 HB -----------------------------------------
                                                                               [    CDR1    ]

ACATACGCCATGAATTGGGTGCGGCAGGCATCTGGCAAGGGACTGGAGTGGGTGGCCCGGATCAGATCTAAGAGCAACAATTACGCCACC
|-+-+-+-+-+-+-+-+-+-+-+-+-+-+-+-+-+-+-+-+-+-+-+-+-+-+-+-+-+-+-+-+-+-+-+-+-+-+-+-+-+-+-+-+-|  180
TGTATGCGGTACTTAACCCACGCCGTCCGTAGACCGTTCCCTGACCTCACCCACCGGGCCTAGTCTAGATTCTCGTTGTTAATGCGGTGG
         35             40             45             50             55             60
   T   Y   A   M   N   W   V   R   Q   A   S   G   K   G   L   E   W   V   A   R   I   R   S   K   S   N   N   Y   A   T
   >----------------------------------------- Tau01 HB -----------------------------------------
[    CDR1    ]                                                  [              CDR2              ]

TACTATGCCGACAGCGTGAAGGGCAGGTTCACAATCTCCCGCGACGATTCCAAGTCTATGGTGTATCTGCAGATGGACTCCCTGAAGACC
|-+-+-+-+-+-+-+-+-+-+-+-+-+-+-+-+-+-+-+-+-+-+-+-+-+-+-+-+-+-+-+-+-+-+-+-+-+-+-+-+-+-+-+-+-|  270
ATGATACGGCTGTCGCACTTCCCGTCCAAGTGTTAGAGGGCGCTGCTAAGGTTCAGATACCACATAGACGTCTACCTGAGGGACTTCTGG
         65             70             75             80             85             90
   Y   Y   A   D   S   V   K   G   R   F   T   I   S   R   D   D   S   K   S   M   V   Y   L   Q   M   D   S   L   K   T
   >----------------------------------------- Tau01 HB -----------------------------------------

GAGGATACAGCCGTGTACTATTGCGTGGGCGGCGGCGACTTTTGGGGACAGGGCACCCTGGTGACAGTGAGCTCC       3'
|-+-+-+-+-+-+-+-+-+-+-+-+-+-+-+-+-+-+-+-+-+-+-+-+-+-+-+-+-+-+-+-+-+-+-+-+-|       345
CTCCTATGTCGGCACATGATAACGCACCCGCCGCCGCTGAAAACCCCTGTCCCGTGGGACCACTGTCACTCGAGG       5'
         95            100            105            110            115
   E   D   T   A   V   Y   Y   C   V   G   G   G   D   F   W   G   Q   G   T   L   V   T   V   S   S
   >----------------------------------------- Tau01 HB -----------------------------------------
              [    CDR3    ]
```

*Figure 11. Protein and DNA Sequence of Tau01 HC*

```
CTGGTGCAGCTGGTGGAAAGCGGCGGCGGCCTGGTGCAGCCTGGCGGCAGCCTGAAGCTGTCCTGTGCAGCATCTGGCTTCACCTTTAAC
|---+---+---+---+---+---+---+---+---+---+---+---+---+---+---+---+---+---+---+---+---+---+---|   90
GACCACGTCGACCACCTTTCGCCGCCGCCGGACCACGTCGGACCGCCGTCGGACTTCGACAGGACACGTCGTAGACCGAAGTGGAAATTG
     1       5           10          15          20          25          30
     L   V   Q   L   V   E   S   G   G   G   L   V   Q   P   G   G   S   L   K   L   S   C   A   A   S   G   F   T   F   N
     |~~~~~~~~~~~~~~~~~~~~~~~~~~~~~~~~~~~~~~~~~~~~~~ Tau01 HC ~~~~~~~~~~~~~~~~~~~~~~~~~~~~~~~~~~~~~~~~~~~~~~~~~~~~~~~|>
                                                                                                    [::::CDR1::::]
```

```
ACATACGCCATGAATTGGGTGCGCCAGGCATCTGGCAAGGGACTGGAGTGGGTGGGCCGGATCAGATCTAAGAGCAACAATTACGCCACC
|---+---+---+---+---+---+---+---+---+---+---+---+---+---+---+---+---+---+---+---+---+---+---|   180
TGTATGCGGTACTTAACCCACGCCGTCCGTAGACCGTTCCCTGACCTCACCCACCCGGCCTAGTCTAGATTCTCGTTGTTAATGCGGTGG
         35          40          45          50          55          60
     T   Y   A   M   N   W   V   R   Q   A   S   G   K   G   L   E   W   V   G   R   I   R   S   K   S   N   N   Y   A   T
     |~~~~~~~~~~~~~~~~~~~~~~~~~~~~~~~~~~~~~~~~~~~~~~ Tau01 HC ~~~~~~~~~~~~~~~~~~~~~~~~~~~~~~~~~~~~~~~~~~~~~~~~~~~~~~~|>
     [::::CDR1::::]                                          [::::::::CDR2::::::::]
```

```
TACTATGCCGCCAGCGTGAAGGGCAGGTTCACAATCTCCCGCGACGATTCCAAGTCTATGGCCTATCTGCAGATGGACTCCCTGAAGACC
|---+---+---+---+---+---+---+---+---+---+---+---+---+---+---+---+---+---+---+---+---+---+---|   270
ATGATACGGCGGTCGCACTTCCCGTCCAAGTGTTAGAGGGCGCTGCTAAGGTTCAGATACCGGATAGACGTCTACCTGAGGGACTTCTGG
         65          70          75          80          85          90
     Y   Y   A   A   S   V   K   G   R   F   T   I   S   R   D   D   S   K   S   M   A   Y   L   Q   M   D   S   L   K   T
     |~~~~~~~~~~~~~~~~~~~~~~~~~~~~~~~~~~~~~~~~~~~~~~ Tau01 HC ~~~~~~~~~~~~~~~~~~~~~~~~~~~~~~~~~~~~~~~~~~~~~~~~~~~~~~~|>
```

```
GAGGATACAGCCGTGTACTATTGCGTGGGCGGCGGCGACTTTTGGGGACAGGGCACCCTGGTGACAGTGAGCTCC              3'
|---+---+---+---+---+---+---+---+---+---+---+---+---+---+---+---+---+---+---|            345
CTCCTATGTCGGCACATGATAACGCACCCGCCGCCGCTGAAAACCCCTGTCCCGTGGGACCACTGTCACTCGAGG              5'
         95          100         105         110         115
     E   D   T   A   V   Y   Y   C   V   G   G   G   D   F   W   G   Q   G   T   L   V   T   V   S   S
     |~~~~~~~~~~~~~~~~~~~~~~~~~~~~~~~~~~~~~~~~~~~~~~ Tau01 HC ~~~~~~~~~~~~~~~~~~~~|>
                                     [::::::CDR3::::::]
```

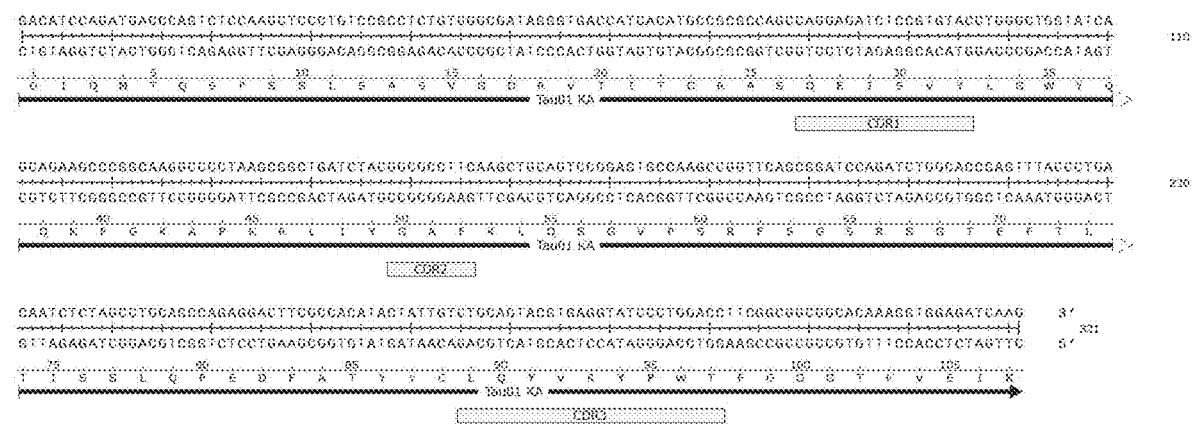
Figure 12. Protein and DNA Sequence of Tau01 KA

Figure 13. Protein and DNA Sequence of Tau01 KB

Figure 14. Protein and DNA Sequence of Tau01 KC

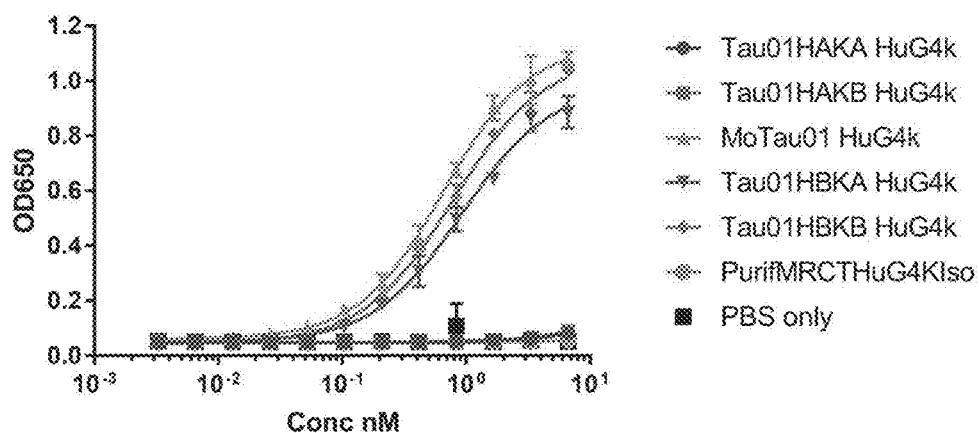
*Figure 15. Binding of humanized and chimeric Tau01 to TauC3: A and B versions*

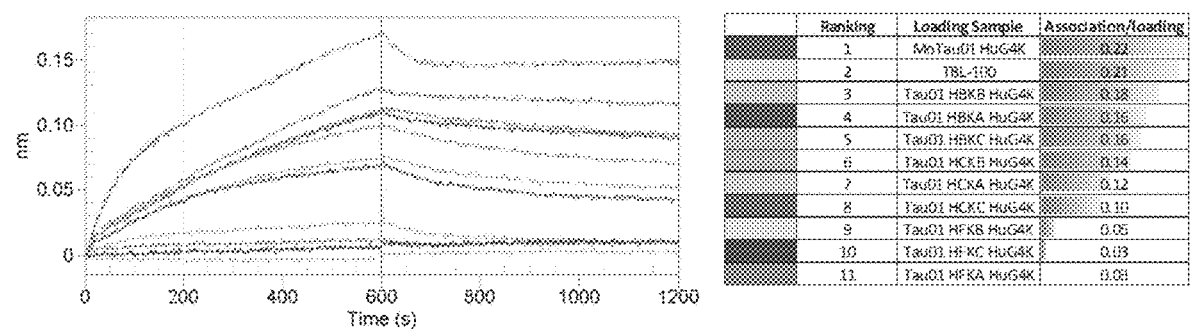
Figure 17. Octet screening of humanized Tau01 antibodies to TauC3: HB, HC and HF with KA-KC

*Binding ELISA of the humanized Tau01 antibodies to TauC3: KA to KJ variants*

| Ab(HuG4K) | EC50 (nM) |
|---|---|
| MoTau01HuG4K | 0.7238 |
| H8KA | 0.7942 |
| H8KB | 0.7675 |
| H8KD | 3.035 |
| H8KE | 0.9153 |
| H8KF | 0.7861 |
| H8KG | 0.7608 |
| H8KH | 0.8066 |
| H8KI | 0.7048 |
| H8KJ | 0.8309 |
| PurifMRCTHuG4K Iso | — |

Fig. 18A

| Ab(HuG4K) | EC50 (nM) |
|---|---|
| MoTau01HuG4K | 0.7238 |
| HCKA | 0.9593 |
| HCKB | 0.6985 |
| HCKD | 2.035 |
| HCKE | 1.237 |
| HCKF | 2.25 |
| HCKG | 0.9798 |
| HCKH | 1.028 |
| HCKI | 0.7813 |
| HCKJ | 1.015 |
| PurifMRCTHuG4K Iso | — |

Fig. 18B

*Binding ELISA of the second round of humanized Tau01 antibodies to TauC3: HM, HN and HO variants*

HM Variants

HN Variants

HO Variants

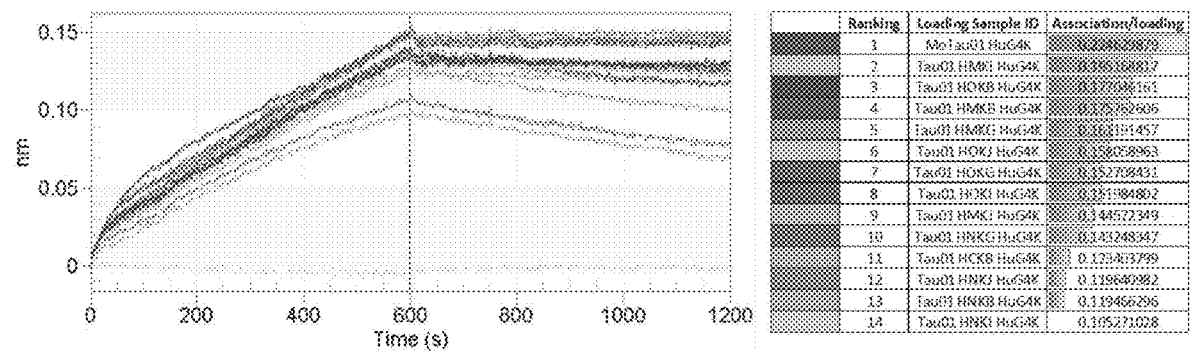
Figure 21. Octet screening of the second round of humanized Tau01 antibodies to TauC3: HM, HN and HO variants

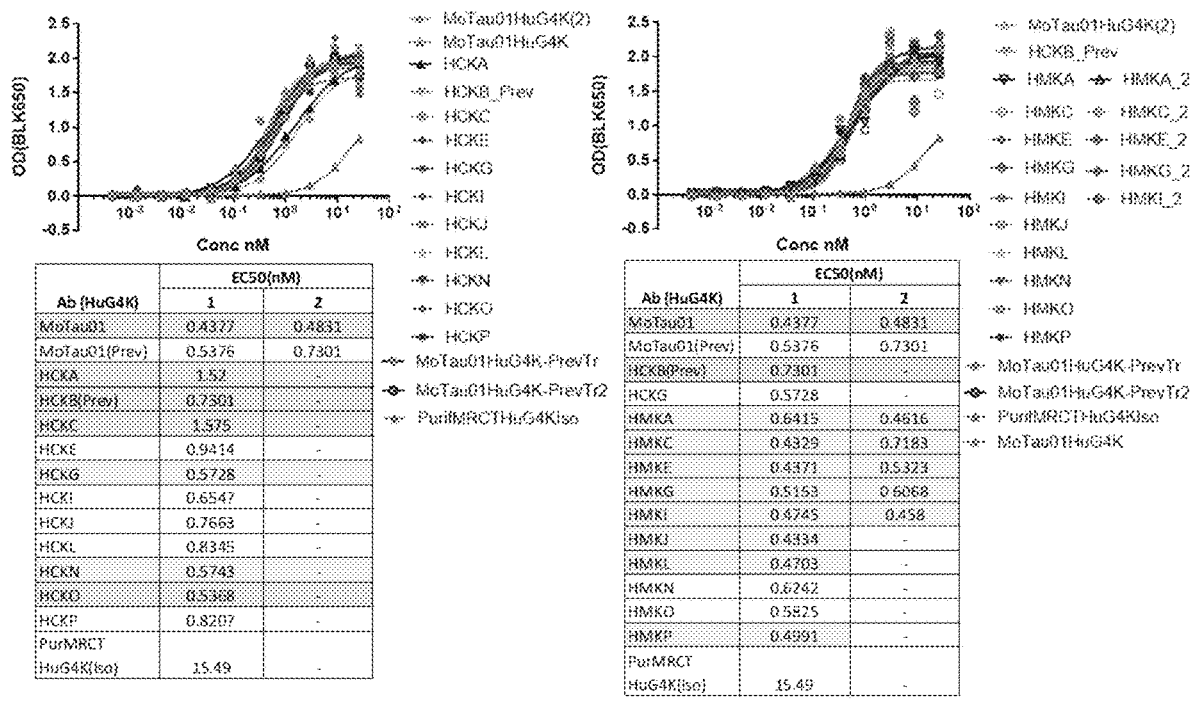
Figure 22. Binding ELISA of HC and HM containing humanized antibodies to TauC3

Figure 23. Octet screening of the second round of humanized Tau01 antibodies to TauC3: HM variants
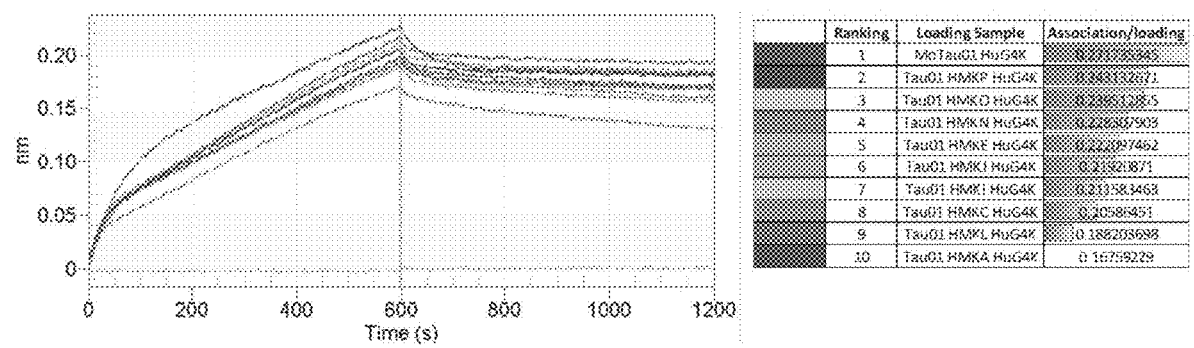

Octet screening of the second round of humanized Tau01 antibodies to TauC3 and FL Tau: Lead variants

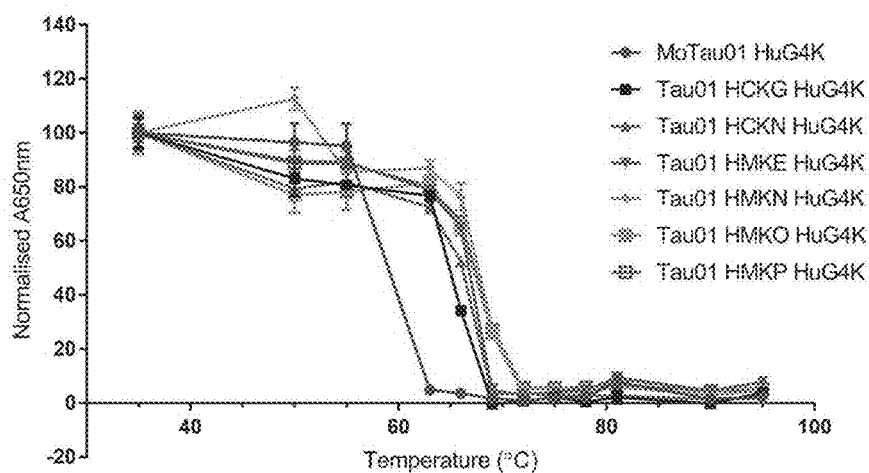
Figure 27. Thermal stability of the chimeric and humanized candidate antibodies

SEC-MALS aggregation analysis of purified MoTau01 HuG4K and Tau01 HCKB HuG4K antibodies

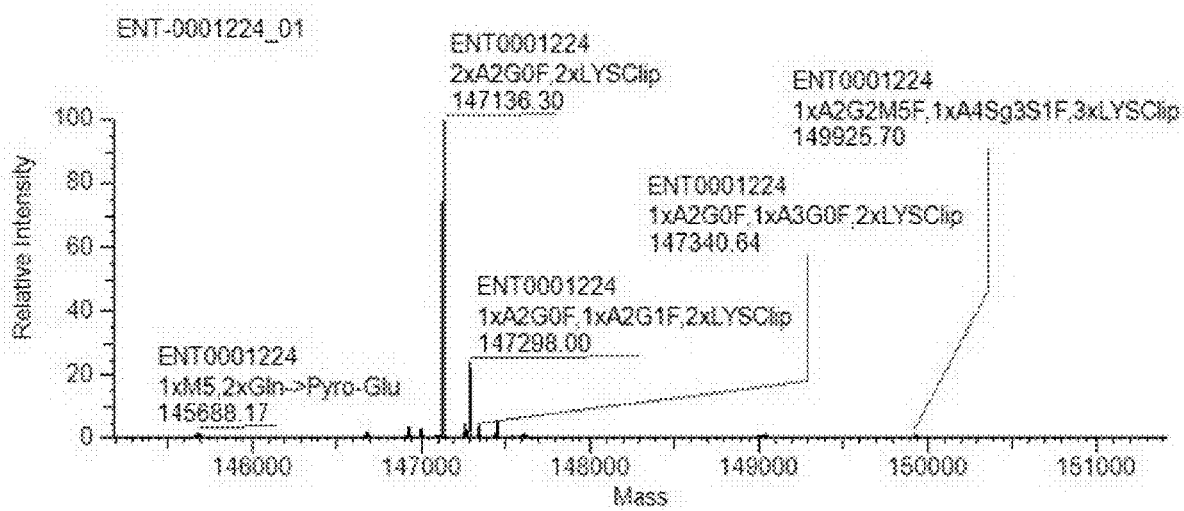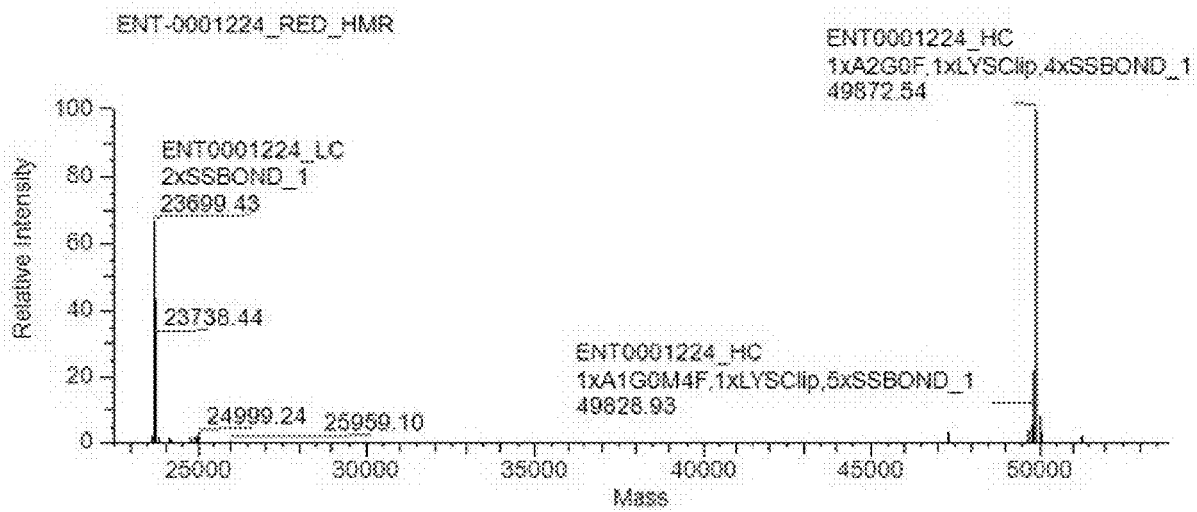
Fig. 30A

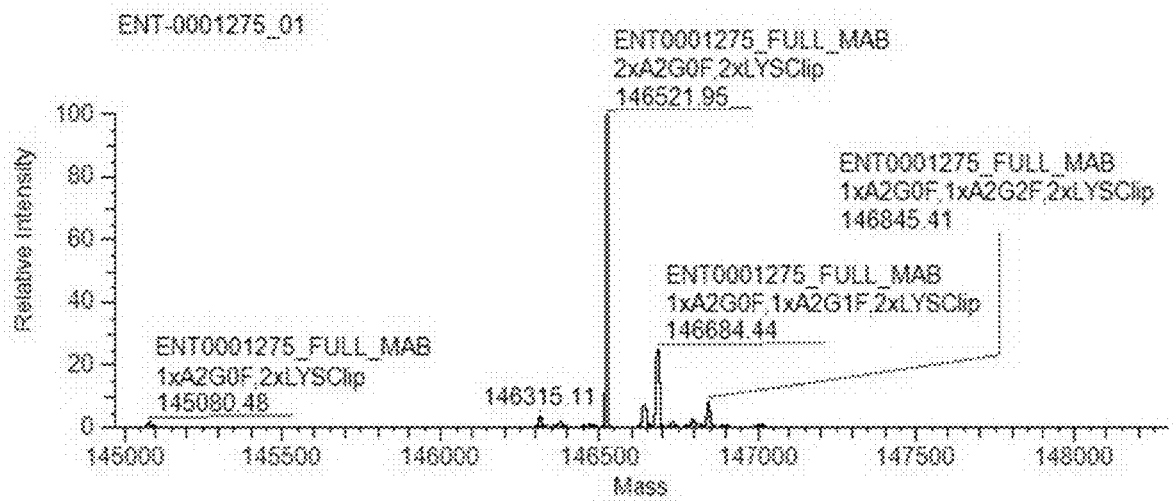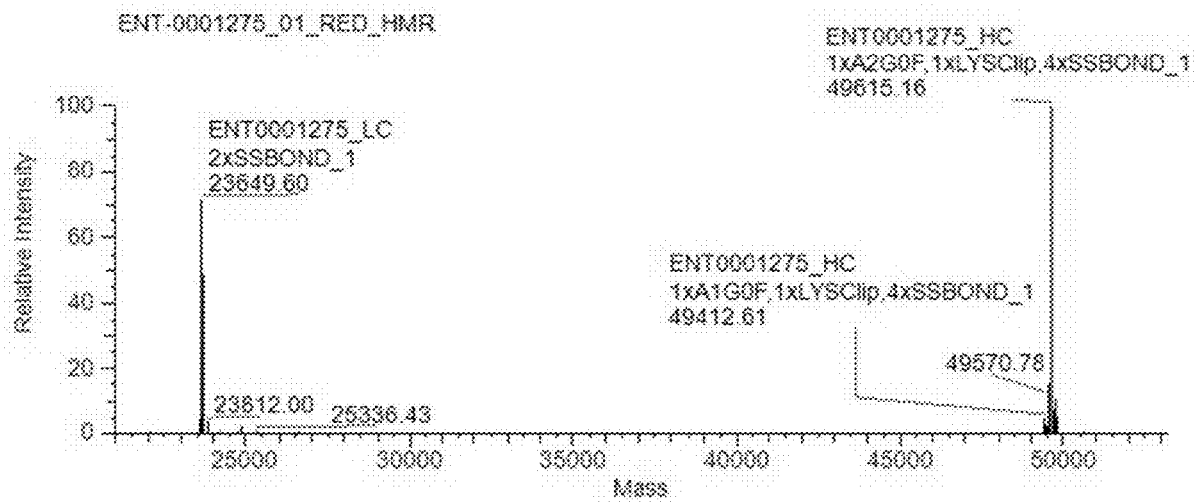
Fig. 30B

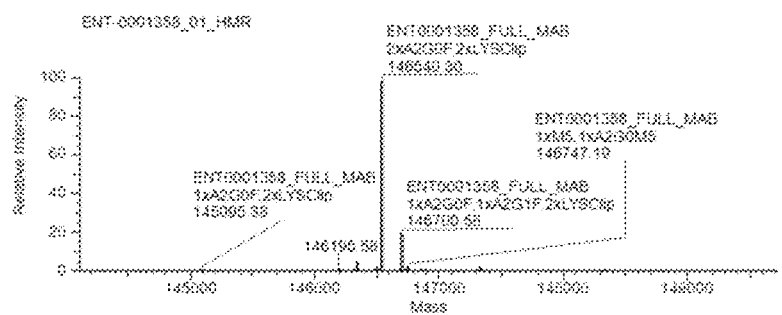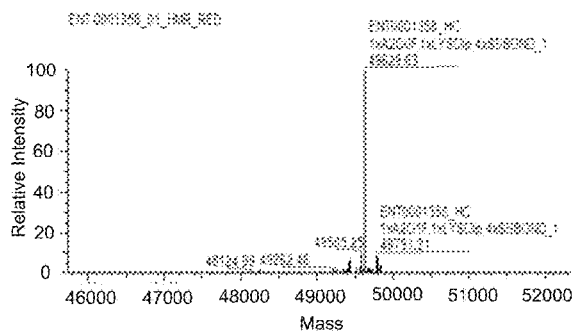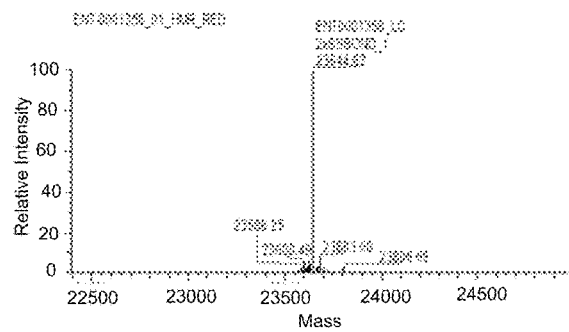
Fig. 30E

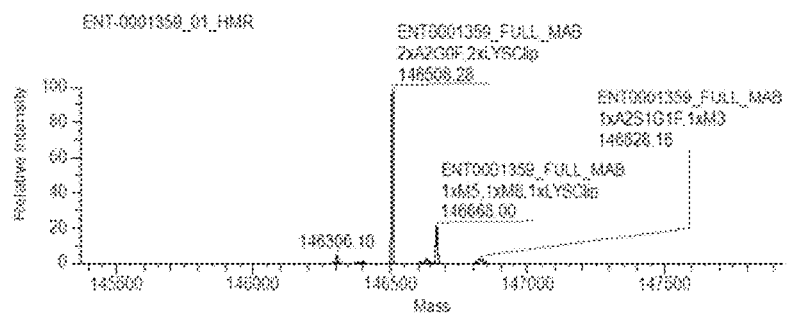
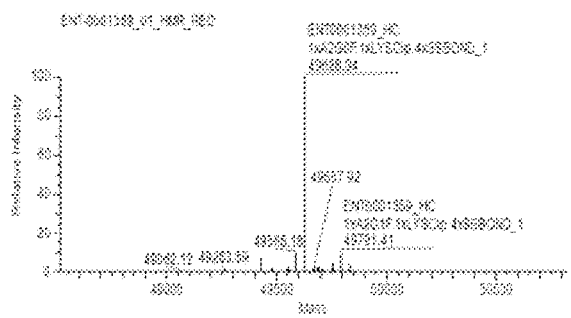
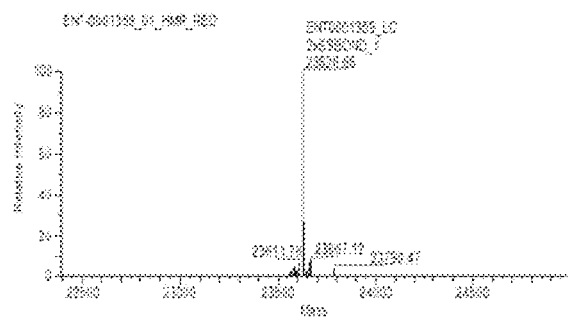
Fig. 30F

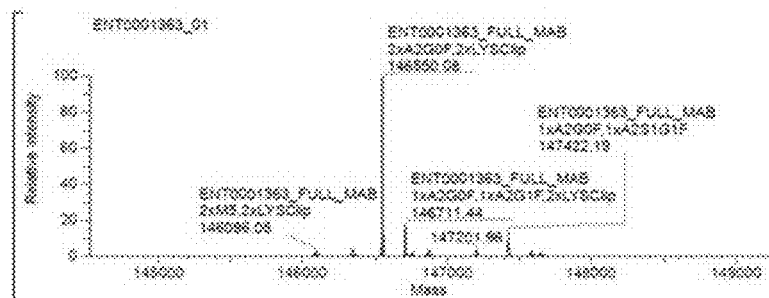
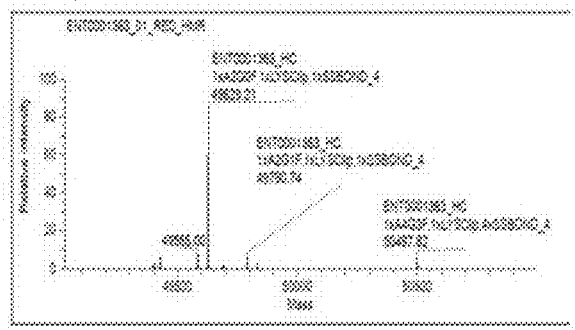
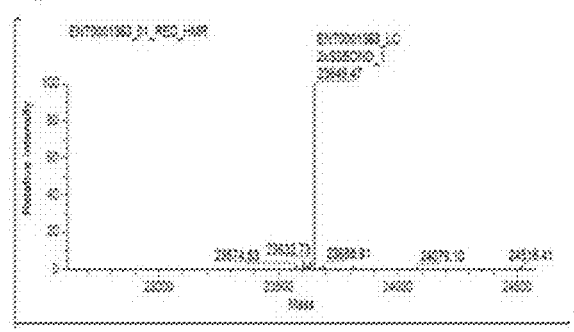
Fig. 30G

Figure 32. Thermal Shift Analysis of the humanized candidate antibodies
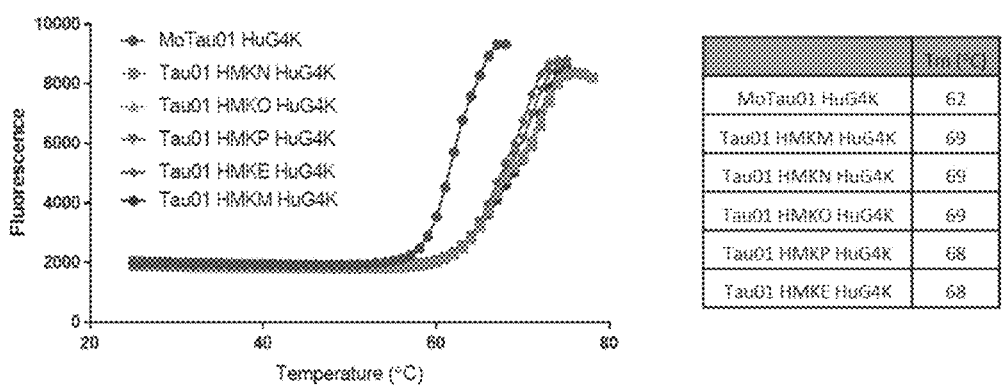

Figure 33. Non-specific protein-protein interactions (Cross-interaction chromatography) of the humanized candidate antibodies
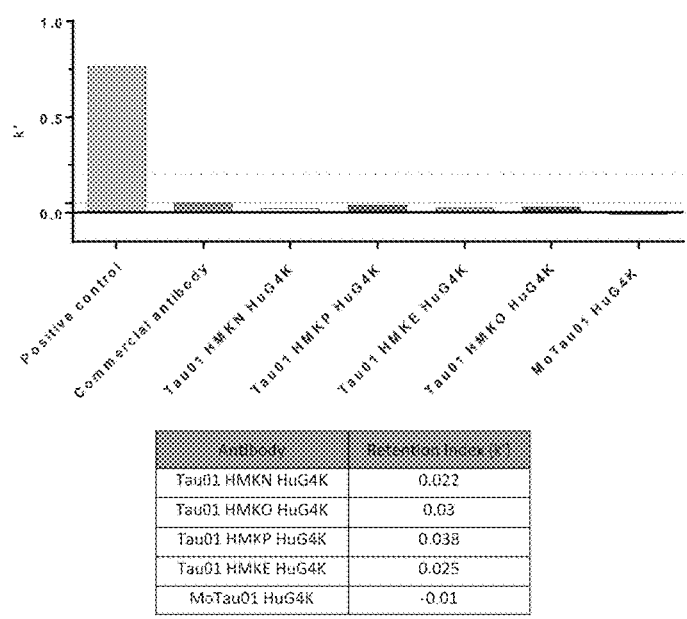
| Antibody | Retention Index |
|---|---|
| Tau01 HMKN HuG4K | 0.022 |
| Tau01 HMKO HuG4K | 0.03 |
| Tau01 HMKP HuG4K | 0.038 |
| Tau01 HMKE HuG4K | 0.025 |
| MoTau01 HuG4K | -0.01 |

Figure 34. Purified humanized antibody candidates assessed for solubility
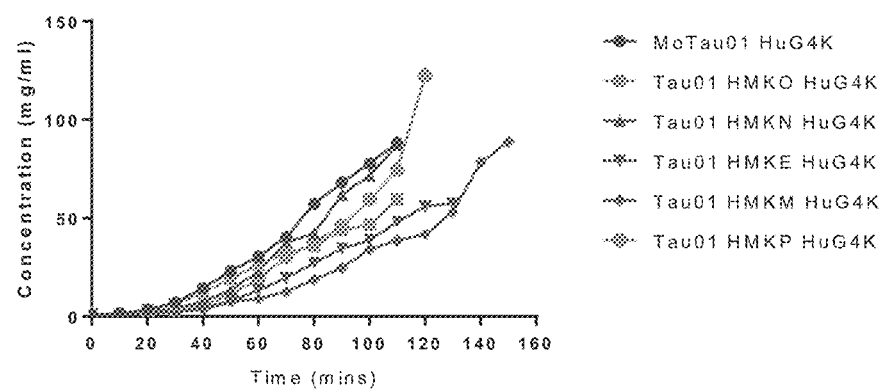

*Freeze/Thaw and heat stress analysis of the humanized candidate antibodies by Circular Dichroism*

*Capillary Isoelectric focusing to determine the isoeletric points of the humanized candidates*

Tau01 HMKN HuG4K

Tau01 HMKO HuG4K

Tau01 HMKP HuG4K

Tau01 HMKE HuG4K

*Serum stability assessment of the humanized candidate antibodies*

Tau01HMKOHuG4K

Tau01HMKPHuG4K

Tau01HMKEHuG4K

ANTI-TAUC3 ANTIBODIES AND USES THEREOF

This application claims the benefit of U.S. Provisional Application No. 62/829,774, filed on Apr. 5, 2019, hereby incorporated by reference.

BACKGROUND OF THE INVENTION

Tau protein is a microtubule associated protein that distributes mainly to axons and modulates the assembly, spatial organization and behavior of microtubules (MT) in neurons. Tau protein is encoded by a single gene located on chromosome 17.

There are six known isoforms of Tau protein. These isoforms differ from each other by the presence or absence of 29- or 58-amino acid inserts in the amino-terminal region and by the addition or deletion of tandem repeats (which can be repeated either 3 or 4 times) in a carboxy-terminal region of tau, which is referred to as microtubule binding domain. The microtubule binding domain region is composed of imperfect repeats of 31 or 32 amino acid residues. The longest tau protein isoform, (2N4R), is 441 amino acids in length and contains four repeats (R1, R2, R3 and R4) and two inserts. The smallest tau isoform contains 352 amino acid residues with three tandem repeats (R1, R3 and R4) in the microtubule binding domain and no amino terminal inserts. The amino acid sequences corresponding to the isoforms of the human tau protein are provided in SEQ ID NOs: 1-6.

SEQ ID NO: 1, the longest tau isoform, htau40, containing two N-terminal inserts and four microtubule binding (2N4R) domains, is as follows:

```
MAEPRQEFEV MEDHAGTYGL GDRKDQGGYT MHQDQEGDTD AGLKESPLQT PTEDGSEEPG  60
SETSDAKSTP TAEDVTAPLV DEGAPGKQAA AQPHTEIPEG TTAEEAGIGD TPSLEDEAAG 120
HVTQARMVSK SKDGTGSDDK KAKGADGKTK IATPRGAAPP GQKGQANATR IPAKTPPAPK 180
TPPSSGEPPK SGDRSGYSSP GSPGTPGSRS RTPSLPTPPT REPKKVAVVR TPPKSPSSAK 240
SRLQTAPVPM PDLKNVKSKI GSTENLKHQP GGGKVQIINK KLDLSNVQSK CGSKDNIKHV 300
PGGGSVQIVY KPVDLSKVTS KCGSLGNIHH KPGGGQVEVK SEKLDFKDRV QSKIGSLDNI 360
THVPGGGNKK IETHKLTFRE NAKAKTDHGA EIVYKSPVVS GDTSPRHLSN VSSTGSIDMV 420
DSPQLATLAD EVSASLAKQG L                                         441
```

SEQ ID NO: 2 contains two N-terminal inserts and three microtubule-binding domains (2N3R) as follows:

```
MAEPRQEFEV MEDHAGTYGL GDRKDQGGYT MHQDQEGDTD AGLKESPLQT PTEDGSEEPG  60
SETSDAKSTP TAEDVTAPLV DEGAPGKQAA AQPHTEIPEG TTAEEAGIGD TPSLEDEAAG 120
HVTQARMVSK SLDGTGSDDK KAKGADGKTK IATPRGAAPP GQKGQANATR IPAKTPPAPK 180
TPPSSGEPPK SGDRSGYSSP GSPGTPGSRS RTPSLPTPPT REPKKVAVVR TPPKSPSSAK 240
SRLQTAPVPM PDLKNVKSKI GSTENLKHQP GGGKVQIVYK PVDLSKVTSK CGSLGNIHHK 300
PGGGQVEVKS EKLDFKDRVQ SKIGSLDNIT HVPGGGNKKI ETHKLTFREN AKAKTDHGAE 360
IVYKSPVVSG DTSPAHLSNV SSTGSIDMVD SPQLATLADE VSASLAKQGL           410
```

SEQ ID NO:3 contains one N-terminal insert and four microtubule-binding domains (1N4R) as follows:

```
MAEPRQEFEV MEDHAGTYGL GDRKDQGGYT MHQDQEGDTD AGLKESPLQT PTGDGSEEPG  60
SETSDAKSTP TAEAEEAGIG DTPSLEDEAA GHVTQARMVS KSLDGTGSDD KKAKGADGKT 120
LIATPRGAAP PGQKGQANAT RIPAKTPPAP KTPPSSGEPP KSGDRSGYSS PGSPGTPGSR 180
SRTPSLPTPP TREPKKVAVV RTPPKSPSSA KSRLQTAPVP MPDLKNVKSK IGSTENLKHQ 240
PGGGKVQIIN KKLDLSNVQS KCGSLDNILH VPGGGSVQIV YKPVDLSKVT SKCGSLGNIH 300
HKPGGGQVEV KSEKLDFKDR VQSKIGSLDN ITHVPGGGNK KIETHKLTFR ENAKAKTDHG 360
AEIVYKSPVV SGDTSPRHLS NVSSTGSIDM VDSPQLATLA DEVSASLAKQ GL        412
```

SEQ ID NO: 4 contains zero N-terminal inserts and four microtubule-binding domains (0N4R) as follows:

```
MAEPRQEFEV MEDHAGTYGL GDRLDQGGYT MHQDQEGDTD AGLKAEEEAGI GDTPSLEDEA  60
AGHVTQARMV SKSKDGTGSD DKKAKGADGK TKIATPRGAA PPGQKGQANA TRIPAKTPPA 120
PKTPPSSGEP PKSGDRSGYS SPGSPGTPGS RSRTPSLPTP PTREPKKVAV VATPPKSPSS 180
AKSRLQTAPV PMPDLKNVKS LIGSTENLKH QPGGGKVQII NKKLDLSNVQ SKCGSKDNIK 240
HVPGGGSVQI VYKPVDLSKV TSKCGSLGNI HHKPGGGQVE VKSEKLDFKD RVQSKIGSLD 300
NITHVPGGGN KKIETHKLTF RENAKALTDH GAEIVYKSPV VSGDTSPRHL SNVSSTGSID 360
MVDSPQLATL ADEVSASLAK QGL                                      383
```

SEQ ID NO: 5 contains one N-terminal insert and three microtubule-binding domains (1N3R) as follows:

```
MAEPRQEFEV MEDHAGTYGL GDRKDQGGYT MHQDQEGDTD AGLKESPLQT PTEDGSEEPG  60
SETSDAKSTP TAEAEEAGIG DTPSLEDEAA GHVTQARMVS KSKDGTGSDD KKAKGADGKT 120
KIATPRGAAP PGQKGQANAT RIPAKTPPAP KTPPSSGEPP KSGDRSGYSS PGSPGTPGSR 180
SRTPSLPTPP TREPKKVAVV RTPPKSPSSA KSRLQTAPVP MPDLKNVKSK IGSTENLKHQ 240
PGGGKVQIVY KPVDLSKVTS KCGSLGNIHH KPGGGQVEVK SEKLDFKDRV QSKIGSLDNI 300
THVPGGGNKK IETHKLTFRE NAKAKTDHGA EIVYKSPVVS GDTSPRHLSN VSSTGSIDMV 360
DSPQLATLAD EVSASLAKQG L                                        381
```

SEQ ID NO: 6 contains zero N-terminal inserts and three microtubule-binding domains (0N3R) as follows:

```
MAEPRQEFEV MEDHAGTYGL GDRKDQGGYT MHQDQEGDTD AGLKAEEEAGI GDTPSLEDEA  60
AGHVTQARMV SKSKDGTGSD DKKAKGADGK TKIATPRGAA PPGQKGQANA TRIPAKTPPA 120
PKTPPSSGEP PKSGDRSGYS SPGSPGTPGS RSRTPSLPTP PTREPKKVAV VRTPPKSPSS 180
AKSRLQTAPV PMPDLKNVKS KIGSTENLKH QPGGGKVQIV YKPVDLSKVT SKCGSLGNIH 240
HKPGGGQVEV KSEKLDFKDR VQSKIGSLDN ITHVPGGGNK KIGTHKLTFR ENAKAKTDHG 300
AEIVYKSPVV SGDTSPRHLS NVSSTGSIDM VDSPQLATLA DEVSASLAKQ GL        352
```

TauC3 is an extremely noxious, nucleating, pre-tangle, intracellular and preferentially secreted, C-terminally truncated tau fragment ending at aspartate 421. TauC3 exists in low abundance compared to full-length Tau (FLT) (2N4R) but was shown to exert a disproportionately large pathological effect. TauC3 may contribute, e.g., to seeding and spreading of pathological tau aggregation.

Pathological aggregation of tau and spreading of pathological tau in the brain is associated with over 20 neurodegenerative disorders including, e.g., Alzheimer disease (AD), progressive supranuclear palsy (PSP), frontotemporal dementia (FTD), traumatic brain injury (TBI), Pick's disease (PiD), corticobasal degeneration (CBD), frontotemporal lobar degeneration (FTLD), etc. (collectively referred to as "tauopathies").

SUMMARY OF THE INVENTION

It is an object of the invention to provide a chimeric antibody that could be used in the diagnosis and treatment of neurodegenerative disorders associated with pathological activities of TauC3 in the brain.

It is also an object of the invention to provide a humanized antibody that could be used in the diagnosis and treatment of neurodegenerative disorders associated with pathological activities of TauC3 in the brain.

It is also an additional object of the invention to provide a human antibody that could be used in the diagnosis and treatment of neurodegenerative disorders associated with pathological activities of TauC3 in the brain.

It is a further object of the invention to provide a chimeric antibody that is specific for the C-terminus of TauC3.

It is a further object of the invention to provide a chimeric antibody that is specific for the C-terminus of TauC3 and has an off-rate ($K_d$) of $1 \times 10^{-3}$ $s^{-1}$ or less.

It is also an object of the invention to provide a humanized antibody that is specific for the C-terminus of TauC3.

It is also an object of the invention to provide a humanized antibody that is specific for the C-terminus of TauC3 and has an off-rate ($K_d$) of $1 \times 10^{-3}$ $s^{-1}$ or less.

In furtherance of the above objects and others, the invention is directed to chimeric, humanized and human antibodies that are specific for the C-terminus of TauC3 ("anti-TauC3 antibodies"). The anti-TauC3 antibodies have a binding affinity (KD) for TauC3 of from $1 \times 10^{-10}$ to $1 \times 10^{-12}$ and a binding affinity (KD) for full length tau ("FLT") (SEQ ID NO:1) of from $1 \times 10^{-4}$ to $1 \times 10^{-8}$ M. For example, the anti-TauC3 antibodies may have a binding affinity (KD) for TauC3 of about $5 \times 10^{-12}$ M to about $1.2 \times 10^{-10}$ M, from about $1 \times 10^{-11}$ M to about $1 \times 10^{-10}$ M, from about $1 \times 10^{-11}$ M to about $9\times10^{-11}$ M, from about $1\times10^{-11}$ M to about $8\times10^{-11}$ M, from about $1\times10^{-11}$ M to about $7\times10^{-11}$ M, from about $1\times10^{-11}$ M to about $6\times10^{-11}$ M, from about $1\times10^{-11}$ M to about $5\times10^{-11}$ M, or from about $1\times10^{-11}$ M to about $4\times10^{-11}$ M; and a binding affinity (KD) for FLT of from $1\times10^{-4}$ to $1\times10^{-8}$ M. In the preferred embodiments, the antibody retains its binding capability after being subjected to a temperature from about 40° C. to about 67° C. for 10 minutes and also retains its binding capability after incubation in serum (e.g., mouse) at 37° C. for 21 days. The high capability of the anti-TauC3 antibodies allows the antibodies to target TauC3 without compromising normal physiological functions of FLT. In some embodiments, the specificity of the antibody allows to target only the most noxious species of tau. This may allow one, e.g., to potentially reduce the effective therapeutic dose, as compared to an antibody which is not specific and does not discriminate between different species of tau. The anti-TauC3 antibodies, and their antigen binding fragments, could be used, e.g., in the diagnosis and treatment of neurodegenerative disorders associated with pathological activities of TauC3 in the brain, including, e.g., Alzheimer disease (AD), progressive supranuclear palsy (PSP), frontotemporal dementia (FTD), traumatic brain injury (TBI), Pick's disease (PiD), corticobasal degeneration (CBD), frontotemporal lobar degeneration (FTLD), etc. The anti-TauC3 antibody may have an aqueous solubility of 50 mg/ml or more (e.g., from about 50 mg/ml to about 200 mg/ml, from about 55 mg/ml to about 180 mg/ml, from about 55 mg/ml to about 170 mg/ml, from about 55 mg/ml to about 150 mg/ml, from about 55 mg/ml to about 140 mg/ml, from about 55 mg/ml to about 130 mg/ml; or from about 60 mg/ml to about 130 mg/ml.

The invention is further directed to chimeric, humanized and human anti-TauC3 antibodies that have a higher binding affinity (KD) for TauC3 than a murine anti-TauC3 antibody. In some embodiments, the chimeric, humanized and human anti-TauC3 antibodies have a binding affinity (KD) for TauC3 that is at least 2-fold higher, 3-fold higher or 4-fold higher than the binding affinity (KD) for TauC3 of the murine anti-TauC3 antibody. In some embodiments, the murine anti-TauC3 antibody has a binding affinity KD for TauC3 of about $4.9\times10^{-11}$ M, and the chimeric, humanized and human anti-TauC3 antibody has a binding affinity KD for TauC3 of from about $1\times10^{-11}$ M to about $2.5\times10^{-11}$ M. The chimeric, humanized and human anti-TauC3 antibody may have a binding affinity KD for TauC3 of, e.g., about $1.1\times10^{-11}$ M, about $1.3\times10^{-11}$ M, about $1.5\times10^{-11}$ M, about $1.7\times10^{-11}$ M, about $1.9\times10^{-11}$ M, about $2.1\times10^{-11}$ M, or about $2.3\times10^{-11}$ M. The anti-TauC3 antibody may have an aqueous solubility of 50 mg/ml or more (e.g., from about 50 mg/ml to about 200 mg/ml, from about 55 mg/ml to about 180 mg/ml, from about 55 mg/ml to about 170 mg/ml, from about 55 mg/ml to about 150 mg/ml, from about 55 mg/ml to about 140 mg/ml, from about 55 mg/ml to about 130 mg/ml; or from about 100 mg/ml to about 200 mg/ml, from about 100 mg/ml to about 180 mg/ml, from about 100 mg/ml to about 170 mg/ml, from about 100 mg/ml to about 150 mg/ml, from about 100 mg/ml to about 140 mg/ml, or from about 100 mg/ml to about 130 mg/ml).

The invention is also directed to chimeric, humanized and human anti-TauC3 antibodies that have a binding affinity (KD) for TauC3 of from $1\times10^{-10}$ to $1\times10^{-12}$, with an off-rate $(K_d)$ of $1\times10^{-3}$ s$^{-1}$ or less, and a binding affinity (KD) for FLT of from $1\times10^{-4}$ to $1\times10^{-8}$ M.

An anti-TauC3 antibody, or an antigen-binding fragment thereof, comprises (a) a heavy chain variable region comprising CDR1 represented by sequence GFTFNTYA (SEQ ID NO: 7), CDR2 represented by IRSKSNNYAT (SEQ ID NO: 8), and CDR3 represented by VGGGDF (SEQ ID NO: 9); and (b) a light chain variable region comprising CDR1 represented by sequence QEISVY (SEQ ID NO: 10), CDR2 represented by sequence GAF (SEQ ID NO: 11), and CDR3 represented by sequence LQYVRYPWT (SEQ ID NO: 12); and has a binding affinity (KD) for TauC3 of from $1\times10^{-10}$ and $1\times10^{-12}$ and an off-rate $(K_d)$ of $1\times10^{-3}$ or less, and a binding affinity (KD) for FLT (SEQ ID NO:1) of from $1\times10^{-4}$ to $1\times10^{-8}$ M, or no detectable binding with FLT (SEQ ID NO:1).

In certain embodiments, the anti-TauC3 antibody, or an antigen-binding fragment thereof, comprises (a) a heavy chain variable region comprising CDR1 homologous to sequence GFTFNTYA (SEQ ID NO: 7), CDR2 homologous to IRSKSNNYAT (SEQ ID NO: 8), and CDR3 homologous to VGGGDF (SEQ ID NO: 9); and (b) a light chain variable region comprising CDR1 homologous to sequence QEISVY (SEQ ID NO: 10), CDR2 homologous to sequence GAF (SEQ ID NO: 11), and CDR3 homologous to sequence LQYVRYPWT (SEQ ID NO: 12); and has a binding affinity (KD) for TauC3 of from $1\times10^{-10}$ and $1\times10^{-12}$ and an off-rate $(K_d)$ of $1\times10^{-3}$ or less, and a binding affinity (KD) for FLT (SEQ ID NO:1) of from $1\times10^{-4}$ to $1\times10^{-8}$ M, or no detectable binding with FLT (SEQ ID NO:1).

In certain embodiments, the anti-TauC3 antibody, or an antigen-binding fragment thereof, comprises (a) a heavy chain variable region comprising CDR1 identical to sequence GFTFNTYA (SEQ ID NO: 7), CDR2 identical to IRSKSNNYAT (SEQ ID NO: 8), and CDR3 identical to VGGGDF (SEQ ID NO: 9); and (b) a light chain variable region comprising CDR1 identical to sequence QEISVY (SEQ ID NO: 10), CDR2 identical to sequence GAF (SEQ ID NO: 11), and CDR3 identical to sequence LQYVRYPWT (SEQ ID NO: 12); and has a binding affinity (KD) for TauC3 of from $1\times10^{-10}$ and $1\times10^{-12}$ and an off-rate $(K_d)$ of $1\times10^{-3}$ or less, and a binding affinity (KD) for FLT (SEQ ID NO:1) of from $1\times10^{-4}$ to $1\times10^{-8}$ M, or no detectable binding with FLT (SEQ ID NO:1).

In certain embodiments, an anti-TauC3 antibody, or an antigen-binding fragment thereof, comprises (a) a heavy chain variable region comprising CDR1 of sequence GFTFNTYA (SEQ ID NO: 7), CDR2 of sequence IRSKSNNYAT (SEQ ID NO: 8), and CDR3 of sequence VGGGDF (SEQ ID NO: 9); and (b) a light chain variable region comprising CDR1 of sequence QEISVY (SEQ ID NO: 10), CDR2 of sequence GAF (SEQ ID NO: 11), and CDR3 of sequence LQYVRYPWT (SEQ ID NO: 12; and has a binding affinity (KD) for TauC3 of from $1\times10^{-10}$ and $1\times10^{-12}$ and an off-rate $(K_d)$ of $1\times10^{-3}$ or less, and a binding affinity (KD) for SEQ ID NO:1 of from $1\times10^{-4}$ to $1\times10^{-8}$ M, or no detectable binding with SEQ ID NO:1, and is used for treating Alzheimer disease (AD), progressive supranuclear palsy (PSP), frontotemporal dementia (FTD), traumatic brain injury (TBI), Pick's disease (PiD), corticobasal degeneration (CBD), frontotemporal lobar degeneration (FTLD). The antibody may also be used to diagnose a tauopathy, e.g., Alzheimer disease (AD), progressive supranuclear palsy (PSP), frontotemporal dementia (FTD), traumatic brain injury (TBI), Pick's disease (PiD), corticobasal degeneration (CBD), or frontotemporal lobar degeneration (FTLD).

In one aspect, the invention is directed to an anti-TauC3 antibody, which is a humanized antibody comprising (a) a heavy chain variable region comprising CDR1 represented by SEQ ID NO: 7, CDR2 represented by SEQ ID NO: 8, and CDR3 represented by SEQ ID NO: 9; and (b) a light chain variable region comprising CDR1 represented by SEQ ID NO: 10, CDR2 represented by SEQ ID NO: 11, and CDR3 represented by SEQ ID NO: 12; and has a binding affinity (KD) for TauC3 of from $1\times10^{-10}$ and $1\times10^{-12}$ and an off-rate ($K_d$) of $1\times10^{-3}$ s$^{-1}$ or less (e.g., from $1\times10^{-4}$ to $1\times10^{-3}$ s$^{-1}$), and a binding affinity (KD) for FLT (SEQ ID NO:1) of from $1\times10^{-4}$ to $1\times10^{-8}$ M, or no detectable binding with FLT. Thus, the humanized antibody may comprise (a) a heavy chain variable region comprising CDR1 of SEQ ID NO: 7, CDR2 of SEQ ID NO: 8, and CDR3 of SEQ ID NO: 9; and (b) a light chain variable region comprising CDR1 of SEQ ID NO: 10, CDR2 of SEQ ID NO: 11, and CDR3 of SEQ ID NO: 12; and has a binding affinity (KD) for TauC3 of from $1\times10^{-10}$ and $1\times10^{-12}$ and an off-rate ($K_d$) of $1\times10^{-3}$ or less (e.g., from $1\times10^{-4}$ to $1\times10^{-3}$ s$^{-1}$), and a binding affinity (KD) for SEQ ID NO:1 of from $1\times10^{-4}$ to $1\times10^{-8}$ M, or no detectable binding with FLT, and used in treating a tauopathy, e.g., Alzheimer disease (AD), progressive supranuclear palsy (PSP), frontotemporal dementia (FTD), traumatic brain injury (TBI), Pick's disease (PiD), corticobasal degeneration (CBD), frontotemporal lobar degeneration (FTLD), etc.

In one aspect, the invention is directed to an anti-TauC3 antibody, which is a humanized antibody comprising (a) a heavy chain variable region comprising CDR1 identical to SEQ ID NO: 7, CDR2 identical to SEQ ID NO: 8, and CDR3 identical to SEQ ID NO: 9; and (b) a light chain variable region comprising CDR1 identical to SEQ ID NO: 7, CDR2 identical to SEQ ID NO: 11, and CDR3 identical to SEQ ID NO: 12; and has a binding affinity (KD) for TauC3 of from $1\times10^{-10}$ and $1\times10^{-12}$ and an off-rate ($K_d$) of $1\times10^{-3}$ s$^{-1}$ or less (e.g., from $1\times10^{-4}$ to $1\times10^{-3}$ s$^{-1}$), and a binding affinity (KD) for FLT (SEQ ID NO:1) of from $1\times10^{-4}$ to $1\times10^{-8}$ M, or no detectable binding with FLT. Thus, the humanized antibody may comprise (a) a heavy chain variable region with CDR1 of SEQ ID NO: 7, CDR2 of SEQ ID NO: 8, and CDR3 of SEQ ID NO: 9; and (b) a light chain variable region with CDR1 of SEQ ID NO: 10, CDR2 of SEQ ID NO: 11, and CDR3 of SEQ ID NO: 12; and has a binding affinity (KD) for TauC3 of from $1\times10^{-10}$ and $1\times10^{-12}$ and an off-rate ($K_d$) of $1\times10^{-3}$ or less (e.g., from $1\times10^{-4}$ to $1\times10^{-3}$ s$^{-1}$), and a binding affinity (KD) for SEQ ID NO:1 of from $1\times10^{-4}$ to $1\times10^{-8}$M, or no detectable binding with FLT, and used in treating a tauopathy, e.g., Alzheimer disease (AD), progressive supranuclear palsy (PSP), frontotemporal dementia (FTD), traumatic brain injury (TBI), Pick's disease (PiD), corticobasal degeneration (CBD), frontotemporal lobar degeneration (FTLD), etc.

In one aspect, the invention is directed to an anti-TauC3 antibody, which is a humanized antibody comprising (a) a heavy chain variable region comprising CDR1 homologous to SEQ ID NO: 7, CDR2 homologous to SEQ ID NO: 8, and CDR3 homologous to SEQ ID NO: 9; and (b) a light chain variable region comprising CDR1 homologous to SEQ ID NO:, CDR2 homologous to SEQ ID NO: 11, and CDR3 homologous to SEQ ID NO: 12; and has a binding affinity (KD) for TauC3 of from $1\times10^{-10}$ and $1\times10^{-12}$ and an off-rate ($K_d$) of $1\times10^{-3}$ s$^{-1}$ or less (e.g., from $1\times10^{-4}$ to $1\times10^{-3}$ s$^{-1}$), and a binding affinity (KD) for FLT (SEQ ID NO:1) of from $1\times10^{-4}$ to $1\times10^{-8}$ M, or no detectable binding with FLT. Thus, the humanized antibody may comprise (a) a heavy chain variable region comprising CDR1 of SEQ ID NO: 7, CDR2 of SEQ ID NO: 8, and CDR3 of SEQ ID NO: 9; and (b) a light chain variable region comprising CDR1 of SEQ ID NO: 10, CDR2 of SEQ ID NO: 11, and CDR3 of SEQ ID NO: 12; and has a binding affinity (KD) for TauC3 of from $1\times10^{-10}$ and $1\times10^{-12}$ and an off-rate ($K_d$) of $1\times10^{-3}$ or less (e.g., from $1\times10^{-4}$ to $1\times10^{-3}$ s$^{-1}$), and a binding affinity (KD) for SEQ ID NO:1 of from $1\times10^{-4}$ to $1\times10^{-8}$ M, or no detectable binding with FLT, and used in treating a tauopathy, e.g., Alzheimer disease (AD), progressive supranuclear palsy (PSP), frontotemporal dementia (FTD), traumatic brain injury (TBI), Pick's disease (PiD), corticobasal degeneration (CBD), frontotemporal lobar degeneration (FTLD), etc.

The humanized antibody may, e.g., comprise:

(a) a variable heavy chain comprising sequence LVQLVESGGGLVQPGGSLKLSCAASGFTFN-TYAMNWVRQASGKGLEWVARIRSKS-NNYATYYAASVKGRFTISRDDSKSMAYLQMDSLKT-EDTAVYYCVGGGDFWGQGTLVT VSS (SEQ ID NO: 13) or a sequence homologous to SEQ ID NO: 13; and (b) the variable light chain comprising a sequence selected from the group consisting of DIQMTQSPSSL-SASVGDRVTIT-CRASQEISVYLGWFQQKPGKAPKRLIYGAFKLQS-GVPS RFSGSRSGTEFTLTISSLQPEDFATYY-CLQYVRYPWTFGGGTKVEIK (SEQ ID NO: 14) or a sequence homologous to SEQ ID NO: 14, DIQMTQSPSSLSASVGDRVTIT-CRASQEISVYLGWYQQKPGKAPKRLIYGAFTLQ SGVPSRFSGSRSGTEYTLTISSLQPEDFATYY-CLQYVRYPWTFGGGTKVEIK (SEQ ID NO: 15) or a sequence homologous to SEQ ID NO: 15, DIQMTQSPSSLSASVGDRVTIT-CRASQEISVYLGWYQQKPGKAPKRLIYGAFSLQ SGVPSRFSGSRSGTEYTLTISSLQPEDFATYY-CLQYVRYPWTFGGGTKVEIK (SEQ ID NO: 16) or a sequence homologous to SEQ ID NO: 16, DIQMTQSPSSLSASVGDRVTIT-CRASQEISVYLGWFQQKPGKAPKRLIYGAFKLQ SGVPSRFSGSRSGTEYTLTISSLQPEDFATYY-CLQYVRYPWTFGGGTKVEIK (SEQ ID NO: 17) or a sequence homologous to SEQ ID NO: 17, and DIQMTQSPSSLSASVGDRVTIT-CRASQEISVYLSWFQQKPGKAIKRLIYGAFSLQS GVPSRFSGSRSGTEYTLTISSLQPEDFATYY-CLQYVRYPWTFGGGTKVEIK (SEQ ID NO: 18) or a sequence homologous to SEQ ID NO: 18, and have a binding affinity (KD) for TauC3 of from $1\times10^{-10}$ and $9\times10^{-12}$, and a binding affinity (KD) for FLT (SEQ ID NO:1) of from $1\times10^{-4}$ to $1\times10^{-8}$ M, or no detectable binding with FLT.

In certain embodiments, the humanized antibody comprises a variable heavy chain ($V_H$) polypeptide of SEQ ID NO: 13 and the variable light chain ($V_L$) polypeptide of SEQ ID NO: 14, SEQ ID NO: 15, SEQ ID NO: 17, or SEQ ID NO: 18.

In certain embodiments, the humanized antibody comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, the variable heavy chain ($V_H$) polypeptide possessing at least 70% sequence identity to SEQ ID NO: 13; and (b) a variable light chain ($V_L$) polypeptide comprising CDR1 represented by SEQ ID NO: 10, CDR2 represented by SEQ ID NO: 11, and CDR3 represented by SEQ ID NO: 12, the variable light chain ($V_L$) polypeptide possessing at least 70% sequence identity to SEQ ID NO: 14, SEQ ID NO: 15, SEQ ID NO: 16, SEQ ID NO: 17, or SEQ ID NO: SEQ ID NO: 18.

In certain embodiments, the humanized antibody comprises a $V_L$ chain polypeptide possessing at least 75% sequence identity to SEQ ID NO: 13, and a $V_H$ chain polypeptide possessing at least 75% sequence identity to SEQ ID NO: 14, SEQ ID NO: 15, SEQ ID NO: 16, SEQ ID NO: 17, or SEQ ID NO: 18.

In certain embodiments, the humanized antibody comprises a $V_L$ chain polypeptide possessing at least 80% sequence identity to SEQ ID NO: 13, and a $V_H$ chain polypeptide possessing at least 80% sequence identity to SEQ ID NO: 14, SEQ ID NO: 15, SEQ ID NO: 16, SEQ ID NO: 17, or SEQ ID NO: 18.

In certain embodiments, the humanized antibody comprises a $V_L$ chain polypeptide possessing at least 85% sequence identity to SEQ ID NO: 13, and a $V_H$ chain polypeptide possessing at least 85% sequence identity to SEQ ID NO: 14, SEQ ID NO: 15, SEQ ID NO: 16, SEQ ID NO: 17, or SEQ ID NO: 18.

In certain embodiments, the humanized antibody comprises a $V_L$ chain polypeptide possessing at least 90% sequence identity to SEQ ID NO: 13, and a $V_H$ chain polypeptide possessing at least 90% sequence identity to SEQ ID NO: 14, SEQ ID NO: 15, SEQ ID NO: 16, SEQ ID NO: 17, or SEQ ID NO: 18.

In certain embodiments, the humanized antibody comprises a $V_L$ chain polypeptide possessing at least 95% sequence identity to SEQ ID NO: 13, and a $V_H$ chain polypeptide possessing at least 95% sequence identity to SEQ ID NO: 14, SEQ ID NO: 15, SEQ ID NO: 16, SEQ ID NO: 17, or SEQ ID NO: 18.

In certain embodiments, the anti-TauC3 antibody comprises a variable heavy chain ($V_H$) polypeptide comprising SEQ ID NO: 13; and the variable light chain ($V_L$) polypeptide comprising a sequence selected from the group consisting of SEQ ID NO: 14, SEQ ID NO: 15, SEQ ID NO: 16, SEQ ID NO: 17, and SEQ ID NO: 18.

In certain embodiments, the anti-TauC3 antibody comprises (i) a variable heavy chain ($V_H$) polypeptide comprising CDR1, CDR2 and CDR 3, wherein CDR1 is a polypeptide of SEQ ID NO: 7, CDR2 is a polypeptide of SEQ ID NO: 8, and CDR3 is a polypeptide of SEQ ID NO: 9; and (ii) a light chain ($V_L$) polypeptide comprising CDR1, CDR2 and CDR3, wherein CDR1 is a polypeptide of SEQ ID NO: 10, CDR2 is a polypeptide of SEQ ID NO: 11, and CDR3 is a polypeptide of SEQ ID NO: 12.

In certain embodiments, anti-TauC3 antibody comprises (i) a variable heavy chain ($V_H$) polypeptide; and (ii) a light chain ($V_L$) polypeptide, wherein the variable heavy chain ($V_H$) polypeptide is a polypeptide of SEQ ID NO: 13 and the variable light chain ($V_L$) polypeptide is a polypeptide of SEQ ID NO: 14, SEQ ID NO: 15, SEQ ID NO: 16, SEQ ID NO: 17, or SEQ ID NO: 18.

The anti-TauC3 antibody could also be a chimeric antibody comprising (a) a heavy chain variable region comprising CDR1 represented by SEQ ID NO: 7 or a sequence homologous to SEQ ID NO: 7, CDR2 represented by SEQ ID NO: 8 or a sequence homologous to SEQ ID NO: 8, and CDR3 represented by SEQ ID NO: 9 or a sequence homologous to SEQ ID NO:9; and (b) a light chain variable region comprising CDR1 represented by SEQ ID NO: 10 or a sequence homologous to SEQ ID NO: 10, CDR2 represented by SEQ ID NO: 11 or a sequence homologous to SEQ ID NO: 11, and CDR3 represented by SEQ ID NO: 12 or a sequence homologous to SEQ ID NO: 12; and having a binding affinity (KD) for TauC3 of from $1\times10^{-10}$ and $1\times10^{-12}$ and an off-rate ($K_d$) of $1\times10^{-3}$ s$^{-1}$ or less (e.g., from $1\times10^{-4}$ to $1\times10^{-3}$ s$^{-1}$), and a binding affinity (KD) for FLT (SEQ ID NO:1) of from $1\times10^{-4}$ to $1\times10^{-8}$ M, or no detectable binding with FLT (SEQ ID NO:1).

The invention is also directed to an antigen-binding fragment of an antibody comprising (a) a heavy chain variable region comprising CDR1 represented by SEQ ID NO: 7, CDR2 represented by SEQ ID NO: 8, and CDR3 represented by SEQ ID NO: 9; and (b) a light chain variable region comprising CDR1 represented by SEQ ID NO: 10, CDR2 represented by SEQ ID NO: 11, and CDR3 represented by SEQ ID NO: 12; and having a binding affinity (KD) for TauC3 of from $1\times10^{-10}$ and $1\times10^{-12}$ and an off-rate ($K_d$) of $1\times10^{-3}$ s$^{-1}$ or less (e.g., from $1\times10^{-4}$ to $1\times10^{-3}$ s$^{-1}$), and a binding affinity (KD) for FLT (SEQ ID NO:1) of from $1\times10^{-4}$ to $1\times10^{-8}$ M, or no detectable binding with FLT (SEQ ID NO:1). The antigen binding fragment of the antibody could, e.g., be a Fab fragment, a Fab' fragment, a F(ab')2 fragment, or a scFv fragment.

The invention is also directed to an antigen-binding fragment of an antibody comprising (a) a heavy chain variable region comprising CDR1 homologous to SEQ ID NO: 7, CDR2 homologous to SEQ ID NO: 8, and CDR3 homologous to SEQ ID NO: 9; and (b) a light chain variable region comprising CDR1 homologous to SEQ ID NO: 10, CDR2 homologous to SEQ ID NO: 11, and CDR3 homologous to SEQ ID NO: 12; and having a binding affinity (KD) for TauC3 of from $1\times10^{-10}$ and $1\times10^{-12}$ and an off-rate ($K_d$) of $1\times10$'s$^{-1}$ or less (e.g., from $1\times10^{-4}$ to $1\times10^{-3}$ s$^{-1}$), and a binding affinity (KD) for FLT (SEQ ID NO:1) of from $1\times10^{-4}$ to $1\times10^{-8}$ M, or no detectable binding with FLT (SEQ ID NO:1). The antigen binding fragment of the antibody could, e.g., be a Fab fragment, a Fab' fragment, a F(ab')2 fragment, or a scFv fragment.

The invention is also directed to an antigen-binding fragment of an antibody comprising (a) a heavy chain variable region comprising CDR1 identical to SEQ ID NO: 7, CDR2 identical to SEQ ID NO: 8, and CDR3 identical to SEQ ID NO: 9; and (b) a light chain variable region comprising CDR1 identical to SEQ ID NO: 10, CDR2 identical to SEQ ID NO: 11, and CDR3 identical to SEQ ID NO: 12; and having a binding affinity (KD) for TauC3 of from $1\times10^{-10}$ and $1\times10^{-12}$ and an off-rate ($K_d$) of $1\times10^{-3}$ s$^{-1}$ or less (e.g., from $1\times10^{-4}$ to $1\times10^{-3}$ s$^{-1}$), and a binding affinity (KD) for FLT (SEQ ID NO:1) of from $1\times10^{-4}$ to $1\times10^{-8}$ M, or no detectable binding with FLT (SEQ ID NO:1). The antigen binding fragment of the antibody could, e.g., be a Fab fragment, a Fab' fragment, a F(ab')2 fragment, or a scFv fragment.

The invention is also directed to methods of blocking uptake of pathological tau, methods of blocking pathological tau seeding activities, methods of inhibiting pathological tau aggregation, and methods of blocking spreading of pathological tau, tau fibrils and tau aggregates from one neuron to another or from one part of the brain to another. The methods comprise administering an effective amount of anti-TauC3 antibodies to a subject in need thereof. In some of these embodiments, the anti-TauC3 comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, and (b) a variable light chain ($V_L$) polypeptide comprising CDR1 represented by SEQ ID NO: 10, CDR2 represented by SEQ ID NO: 11, and CDR3 represented by SEQ ID NO: 12.

Once administered, the anti-TauC3 antibodies may block or slow spreading of pathological tau from one neuron to another or from one part of the brain to another by, e.g., blocking or slowing down TauC3 seeding activities, e.g., by essentially blocking or slowing down intracellular uptake of TauC3. This mechanism takes place extracellularly and does not require for the anti-TauC3 antibodies to be present inside the neurons. The anti-TauC3 antibodies are able to block or slow down spreading of TauC3 tau, fibrils comprising TauC3 and aggregates comprising TauC3 from one neuron to another and from one part of the brain to another. The aggregates may comprise a heterogeneous population of full-length tau (e.g., 2N4R), tau oligomers and/or post-translationally modified tau (truncated or hyperphosphorylated). In addition to blocking intracellular uptake of TauC3 and fibrils comprising TauC3, the anti-TauC3 antibodies may also block or slow down pathological tau aggregation inside the cells (e.g., neurons). Because the antibodies have substantially no affinity for full length tau (e.g., 2N4R), the antibodies should not interfere with normal non-pathological functions of full length tau. In some embodiments, the anti-TauC3 antibody comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, and (b) a variable light chain ($V_L$) polypeptide comprising CDR1 represented by SEQ ID NO: 10, CDR2 represented by SEQ ID NO: 11, and CDR3 represented by SEQ ID NO: 12.

The anti-TauC3 antibodies may also slow the spreading of fibrils and aggregates comprising TauC3 by binding extracellular TauC3 and aggregates comprising TauC3 released from cells, thereby preventing entry of TauC3 and aggregates comprising TauC3 into neighboring cells and slowing spread of tau aggregation from one neuron to another and from one part of the brain to another. Therefore, the anti-TauC3 antibodies may serve as means for preventing entry of TauC3 or aggregates comprising TauC3 into a cell (e.g., a neuron). In some embodiments, the anti-TauC3 antibody comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, and (b) a variable light chain ($V_L$) polypeptide comprising CDR1 represented by SEQ ID NO: 10, CDR2 represented by SEQ ID NO: 11, and CDR3 represented by SEQ ID NO: 12.

The anti-TauC3 antibodies may also be used to slow and/or reduce neuron-to-neuron spreading of tau aggregation. For example, the anti-TauC3 antibodies may promote the disaggregation of protein fibrils comprising TauC3, block the intracellular conversion of monomeric TauC3 into fibrils and/or aggregates comprising TauC3, and promote intracellular degradation of fibrils comprising TauC3 and/or aggregates comprising TauC3. In addition to TauC3, the fibrils and aggregates may comprise a heterogeneous population of full-length tau (e.g., 2N4R), tau oligomers and/or post-translationally modified tau (truncated or hyperphosphorylated). In some embodiments, the anti-TauC3 antibody comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, and (b) a variable light chain ($V_L$) polypeptide comprising CDR1 represented by SEQ ID NO: 10, CDR2 represented by SEQ ID NO: 11, and CDR3 represented by SEQ ID NO: 12.

The anti-TauC3 antibodies may decrease brain atrophy in a subject with a tauopathy. In some embodiments, the anti-TauC3 antibody comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, and (b) a variable light chain ($V_L$) polypeptide comprising CDR1 represented by SEQ ID NO: 10, CDR2 represented by SEQ ID NO: 11, and CDR3 represented by SEQ ID NO: 12.

The anti-TauC3 antibodies may also inhibit formation of insoluble aggregates comprising a heterogeneous population of full-length tau (e.g., 2N4R), tau oligomers and/or post-translationally modified tau (truncated or hyperphosphorylated), e.g., reducing the amount of pathological tau in the brain (e.g., TauC3, fibrils comprising TauC3 and aggregates comprising TauC3). In some embodiments, the anti-TauC3 antibody comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, and (b) a variable light chain ($V_L$) polypeptide comprising CDR1 represented by SEQ ID NO: 10, CDR2 represented by SEQ ID NO: 11, and CDR3 represented by SEQ ID NO: 12.

In certain embodiments, the anti-TauC3 antibodies inhibit pathological aggregation of full-length Tau (e.g., 2N4R). In some of embodiments, the anti-TauC3 comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, and (b) a variable light chain ($V_L$) polypeptide comprising CDR1 represented by SEQ ID NO: 10, CDR2 represented by SEQ ID NO: 11, and CDR3 represented by SEQ ID NO: 12.

In certain embodiments, the administration of the anti-TauC3 antibodies may immunize the subject from developing a tauopathy. In some of embodiments, the anti-TauC3 comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, and (b) a variable light chain ($V_L$) polypeptide comprising CDR1 represented by SEQ ID NO: 10, CDR2 represented by SEQ ID NO: 11, and CDR3 represented by SEQ ID NO: 12.

The administration of the anti-TauC3 antibodies may reduce symptom(s) of a tauopathy in a subject and/or slow down the progress of tauopathy in the subject. For example, in certain embodiments, the administration of the anti-TauC3 antibodies may improve cognitive function of and/or motor/sensorimotor function in a subject with a tauopathy. In some embodiments, the anti-TauC3 antibody comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, and (b) a variable light chain ($V_L$) polypeptide comprising CDR1 represented by SEQ ID NO: 10, CDR2 represented by SEQ ID NO: 11, and CDR3 represented by SEQ ID NO: 12.

The anti-TauC3 antibodies of the invention may be used to treat a tauopathy in a human subject. Administrations of the anti-TauC3 antibodies for the treatments of Alzheimer disease (AD), progressive supranuclear palsy (PSP), frontotemporal dementia (FTD), traumatic brain injury (TBI), Pick's disease (PiD), corticobasal degeneration (CBD), frontotemporal lobar degeneration (FTLD) are specifically contemplated. In some embodiments, the anti-TauC3 comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, and (b) a variable light chain ($V_L$) polypeptide comprising CDR1 represented by SEQ ID NO: 10, CDR2 represented by SEQ ID NO: 11, and CDR3 represented by SEQ ID NO: 12.

In certain embodiments, the invention is directed to a method of reducing the spread of tau aggregation in the brain of a subject comprises administering a therapeutically effective amount of anti-TauC3 antibody to the subject, wherein the antibody binds TauC3, but not full length Tau. In some embodiments, the anti-TauC3 antibody comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, and (b) a variable light chain ($V_L$) polypeptide comprising CDR1 represented by SEQ ID NO: 10, CDR2 represented by SEQ ID NO: 11, and CDR3 represented by SEQ ID NO: 12.

The invention is further directed to a method of treating a tauopathy in a subject comprising administering a therapeutically effective amount of anti-TauC3 antibody sufficient to block TauC3 seeding activity to the subject, wherein the anti-TauC3 antibody is a humanized antibody. In some embodiments, the humanized anti-TauC3 comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, and (b) a variable light chain ($V_L$) polypeptide comprising CDR1 represented by SEQ ID NO: 10, CDR2 represented by SEQ ID NO: 11, and CDR3 represented by SEQ ID NO: 12.

The invention is also directed to a method of treating a tauopathy in a subject comprising administering a therapeutically effective amount of TauC3 antibody sufficient to block reuptake of TauC3 by neurons to the subject, wherein the anti-TauC3 antibody is a chimeric antibody. In some embodiments, the anti-TauC3 comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, and (b) a variable light chain ($V_L$) polypeptide comprising CDR1 represented by SEQ ID NO: 10, CDR2 represented by SEQ ID NO: 11, and CDR3 represented by SEQ ID NO: 12.

The invention is also directed to a method of treating Alzheimer disease in a subject comprising administering a therapeutically effective amount of anti-TauC3 antibody to the subject, wherein the anti-TauC3 antibody is a humanized or chimeric antibody having a binding affinity (KD) for TauC3 of from $1\times10^{-10}$ and $1\times10^{-12}$, with an off-rate ($K_d$) of $1\times10's^{-1}$ or less, and a binding affinity (KD) for FLT of from $1\times10^{-4}$ to $1\times10^{-8}$ M. In some of these embodiments, the anti-TauC3 comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, and (b) a variable light chain ($V_L$) polypeptide comprising CDR1 represented by SEQ ID NO: 10, CDR2 represented by SEQ ID NO: 11, and CDR3 represented by SEQ ID NO: 12.

The invention is also directed to a method of treating progressive supranuclear palsy (PSP) in a subject comprising administering a therapeutically effective amount of anti-TauC3 antibody to the subject, wherein the anti-TauC3 antibody is a humanized or chimeric antibody having a binding affinity (KD) for TauC3 of from $1\times10^{-10}$ and $1\times10^{-12}$, with an off-rate ($K_d$) of $1\times10^{-3}$ s$^{-1}$ or less, and a binding affinity (KD) for FLT (SEQ ID NO:1) of from $1\times10^{-4}$ to $1\times10^{-8}$ M. In some of these embodiments, the anti-TauC3 comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, and (b) a variable light chain ($V_L$) polypeptide comprising CDR1 represented by SEQ ID NO: 10, CDR2 represented by SEQ ID NO: 11, and CDR3 represented by SEQ ID NO: 12.

The invention is also directed to a method of treating frontotemporal dementia (FTD) in a subject comprising administering a therapeutically effective amount of anti-TauC3 antibody to the subject, wherein the anti-TauC3 antibody is a humanized or chimeric antibody having a binding affinity (KD) for TauC3 of from $1\times10^{-10}$ and $1\times10^{-12}$, with an off-rate ($K_d$) of $1\times10^{-3}$ s$^{-1}$ or less, and a binding affinity (KD) for FLT (SEQ ID NO:1) of from $1\times10^{-4}$ to $1\times10^{-8}$ M. In some of these embodiments, the anti-TauC3 comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, and (b) a variable light chain ($V_L$) polypeptide comprising CDR1 represented by SEQ ID NO: 10, CDR2 represented by SEQ ID NO 11, and CDR3 represented by SEQ ID NO: 12.

The invention is also directed to a method of treating traumatic brain injury (TBI) in a subject comprising administering a therapeutically effective amount of anti-TauC3 antibody to the subject, wherein the anti-TauC3 antibody is a humanized or chimeric antibody having a binding affinity (KD) for TauC3 of from $1\times10^{-10}$ and $1\times10^{-12}$, with an off-rate ($K_d$) of $1\times10^{-3}$ s$^{-1}$ or less, and a binding affinity (KD) for FLT (SEQ ID NO:1) of from $1\times10^{-4}$ to $1\times10^{-8}$ M. In some of these embodiments, the anti-TauC3 comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, and (b) a variable light chain ($V_L$) polypeptide comprising CDR1 represented by SEQ ID NO: 10, CDR2 represented by SEQ ID NO: 11, and CDR3 represented by SEQ ID NO: 12.

The invention is also directed to a method of treating Pick's disease (PiD) in a subject comprising administering a therapeutically effective amount of anti-TauC3 antibody to the subject, wherein the anti-TauC3 antibody is a humanized or chimeric antibody having a binding affinity (KD) for TauC3 of from $1\times10^{-10}$ and $1\times10^{-12}$, with an off-rate ($K_d$) of $1\times10's^{-1}$ or less, and a binding affinity (KD) for FLT (SEQ ID NO:1) of from $1\times10^{-4}$ to $1\times10^{-8}$ M. In some of these embodiments, the anti-TauC3 comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, and (b) a variable light chain ($V_L$) polypeptide comprising CDR1 represented by SEQ ID NO: 10, CDR2 represented by SEQ ID NO: 11, and CDR3 represented by SEQ ID NO: 12.

The invention is also directed to a method of treating corticobasal degeneration (CBD) in a subject comprising administering a therapeutically effective amount of anti-TauC3 antibody to the subject, wherein the anti-TauC3 antibody is a humanized or chimeric antibody having a binding affinity (KD) for TauC3 of from $1\times10^{-10}$ and $1\times10^{-12}$, with an off-rate ($K_d$) of $1\times10^{-3}$ s$^{-1}$ or less, and a binding affinity (KD) for FLT (SEQ ID NO:1) of from $1\times10^{-4}$ to $1\times10^{-8}$ M. In some of these embodiments, the anti-TauC3 comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, and (b) a variable light chain ($V_L$) polypeptide comprising CDR1 represented by SEQ ID NO: 10, CDR2 represented by SEQ ID NO: 11, and CDR3 represented by SEQ ID NO: 12.

The invention is also directed to a method of treating frontotemporal lobar degeneration (FTLD) in a subject comprising administering a therapeutically effective amount of anti-TauC3 antibody to the subject, wherein the anti-TauC3 antibody is a humanized or chimeric antibody having a binding affinity (KD) for TauC3 of from $1\times10^{-10}$ and $1\times10^{-12}$, with an off-rate ($K_d$) of $1\times10^{-3}$ s$^{-1}$ or less, and a binding affinity (KD) for FLT of from $1\times10^{-4}$ to $1\times10^{-8}$ M. In some of these embodiments, the anti-TauC3 comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, and (b) a variable light chain (V$_L$) polypeptide comprising CDR1 represented by SEQ ID NO: 10, CDR2 represented by SEQ ID NO: 11, and CDR3 represented by SEQ ID NO: 12.

The invention is also directed to therapeutic agents and compositions for blocking intracellular uptake of pathological tau; therapeutic agents and compositions for blocking tau seeding activities; therapeutic agents and compositions for blocking tau aggregation; and therapeutic agents and compositions for blocking pathological spreading of tau, tau fibrils, tau aggregates, and fragments of any of the foregoing, from one part of the brain to another, the pathological spreading induced or modulated by TauC3. The therapeutic agents and compositions comprise the anti-TauC3 antibodies described above and below. In addition to the anti-TauC3 antibodies, the compositions of the invention may comprise one or more pharmaceutically acceptable excipient(s). The therapeutic agents or compositions may also be used for passive immunization from and treatment of tauopathies, e.g., Alzheimer disease (AD), progressive supranuclear palsy (PSP), frontotemporal dementia (FTD), traumatic brain injury (TBI), Pick's disease (PiD), corticobasal degeneration (CBD), frontotemporal lobar degeneration (FTLD), etc. In certain embodiments, the composition may further include agent(s) that prevents TauC3 production (e.g., caspase inhibitors) or promotes clearance (e.g., small molecule TauC3 aggregation inhibitor(s)).

The invention is further directed to compositions comprising an anti-TauC3 antibody and one or more pharmaceutically acceptable excipient(s), wherein the anti-TauC3 antibody is a humanized or chimeric antibody having a binding affinity (KD) for TauC3 of from $1 \times 10^{-10}$ and $1 \times 10^{-12}$, with an off-rate (K$_d$) of $1 \times 10^{-3}$ s$^{-1}$ or less, and a binding affinity (KD) for FLT (SEQ ID NO:1) of from $1 \times 10^{-4}$ to $1 \times 10^{-8}$ M. In some of these embodiments, the anti-TauC3 comprises (a) a variable heavy chain (V$_H$) polypeptide comprising CDR1 represented by SEQ ID NO: 7, CDR2 represented by SEQ ID NO: 8, and CDR3 represented by SEQ ID NO: 9, and (b) a variable light chain (V$_L$) polypeptide comprising CDR1 represented by SEQ ID NO: 10, CDR2 represented by SEQ ID NO 11, and CDR3 represented by SEQ ID NO: 12. The composition may, e.g., be a liquid composition. The composition comprises an effective amount of the anti-TauC3 antibody to treat a tauopathy, including, e.g., Alzheimer disease (AD), progressive supranuclear palsy (PSP), frontotemporal dementia (FTD), traumatic brain injury (TBI), Pick's disease (PiD), corticobasal degeneration (CBD), frontotemporal lobar degeneration (FTLD), etc. In certain preferred embodiments, the compositions are stable (i.e., at least 90% of the anti-TauC3 antibodies in the composition retain their binding capability after storage of the composition at 37° C. for 21 days).

BRIEF DESCRIPTION OF THE DRAWINGS

FIG. 1. Protein (SEQ ID NO: 122) and DNA (SEQ ID NO: 142) sequence of MoTau01 Kappa Light Chain Variable Region.

FIG. 2. Protein (SEQ ID NO: 105) and DNA (SEQ ID NO: 143) Sequence of MoTau01 Heavy Chain Variable Region.

FIG. 3. pHuK LIC vector.

FIG. 4. pHuG4 LIC vector.

FIG. 5. Protein (SEQ ID NO: 145) and DNA (SEQ ID NO: 144) Sequence of chimeric MoTau01 VK.

FIG. 6. Protein (SEQ ID NO: 147) and DNA (SEQ ID NO: 146) Sequence of chimeric MoTau01 V$_H$.

FIG. 9. Protein (SEQ ID NO: 107) and DNA (SEQ ID NO:148) Sequence of Tau01 HA.

FIG. 10. Protein (SEQ ID NO: 108) and DNA (SEQ ID NO: 149) Sequence of Tau01 HB.

FIG. 11. Protein (SEQ ID NO: 109) and DNA (SEQ ID NO: 150) Sequence of Tau01 HC.

FIG. 12. Protein (SEQ ID NO: 124) and DNA (SEQ ID NO: 151) Sequence of Tau01 KA.

Figure 13:
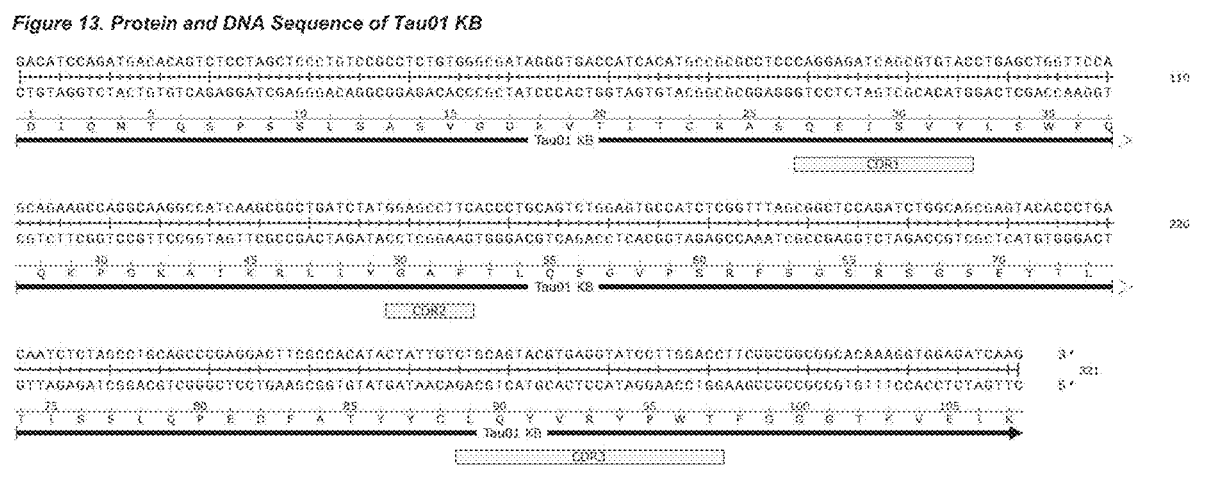

FIG. 13. Protein (SEQ ID NO: 125) and DNA (SEQ ID NO: 152) Sequence of Tau01 KB.

Figure 14:
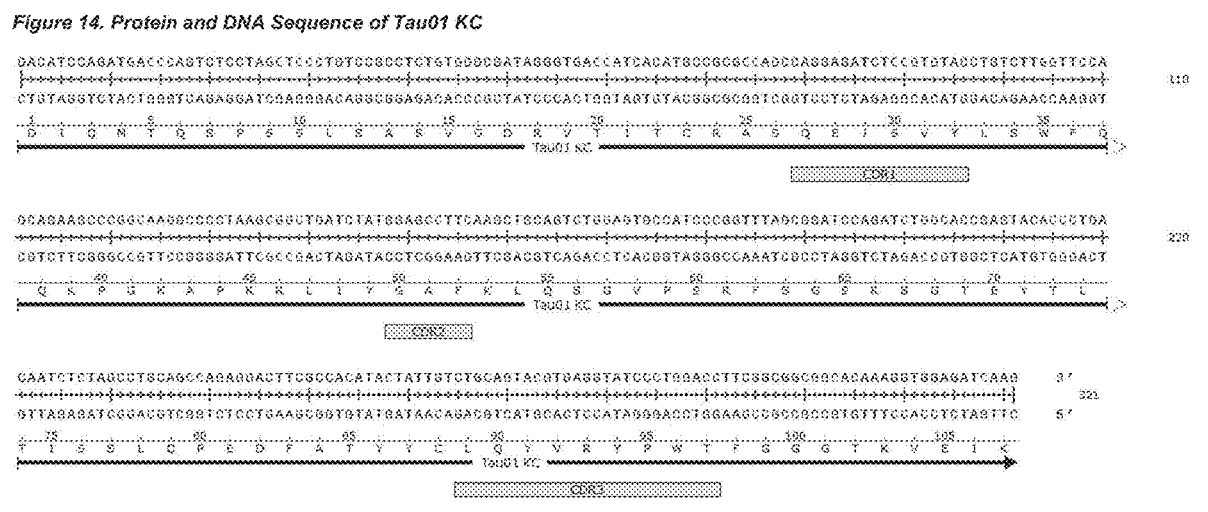

FIG. 14. Protein (SEQ ID NO: 126) and DNA (SEQ ID NO:154) Sequence of Tau01 KC.

FIG. 15. Binding of humanized and chimeric Tau01 to TauC3: A and B versions.

FIGS. 16A and 16B. Binding ELISA of humanized and chimeric Tau01 to TauC3: HA to HL variants.

FIG. 17. Octet screening of humanized Tau01 antibodies to TauC3: HB, HC and HF with KA-KC.

FIGS. 18A and 18B. Binding ELISA of the humanized Tau01 antibodies to TauC3: KA to KJ variants.

FIG. 21. Octet screening of the second round of humanized Tau01 antibodies to TauC3: HM, HN and HO variants.

FIG. 22. Binding ELISA of HC and HM containing humanized antibodies to TauC3.

FIG. 23. Octet screening of the second round of humanized Tau01 antibodies to TauC3: HM variants.

FIG. 27. Thermal stability of the chimeric and humanized candidate antibodies.

FIGS. 30A to 30G. Mass spectrometry of purified chimeric and humanized candidate antibodies.

FIG. 32. Thermal Shift Analysis of the humanized candidate antibodies.

FIG. 33. Non-specific protein-protein interactions (Cross-interaction chromatography) of the humanized candidate antibodies.

FIG. 34. Purified humanized antibody candidates assessed for solubility.

DEFINITIONS

Figure 7A:
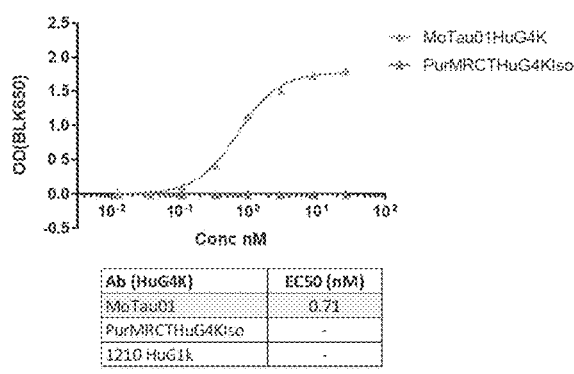
FIGS. 7A and 7B. Binding test of chimeric Tau01 to TauC3 and FL Tau using binding ELISA.

"Antibody" as used herein is meant to include intact molecules (i.e., a full length antibody (IgM, IgG, IgA, IgE)) and fragments thereof, as well as synthetic and biological derivatives thereof, such as for example Fab, F(ab'$_2$ an Fv fragments-free or expressed, e.g., on the surface of filamentous phage on pIII or pVIII or other surface proteins, or on the surface of bacteria, which are capable of binding an antigen. Fab, F(ab'$_2$ and Fv fragments lack the F$_C$ fragments of intact antibody, clear more rapidly from the circulation and may have less non-specific tissue binding of antibody. The antibody may be a monoclonal antibody. Recombinant antibodies are encompassed by the term "antibody." The term "antibody" encompasses chimeric and humanized antibodies. The antibody may also be a fully human antibody (e.g., from a transgenic mice or phage).

The term "humanized antibody" as used herein refers to an antibody in which the complementary-determining regions (CDRs) of a mouse or other non-human antibody are grafted onto a human antibody framework. By human antibody framework is meant the entire human antibody excluding the CDRs.

The term "human antibody" as used herein refers to an antibody in which the entire sequence derived from human genetic repertoire (e.g., from a transgenic mice or phage).

The term "homologous" as used herein means that that the sequence is at least 80% identical to the sequence it is homologous to, and the polymeric peptide (e.g., an antibody) comprising the homologous sequence(s) has substantially same biological activity as the polymeric peptide comprising the sequence(s) it is homologous to. For example, a humanized antibody comprising (a) a heavy chain variable region comprising CDR1 represented by sequence GFTFNTYA (SEQ ID NO: 7), CDR2 represented by IRSKSNNYAT (SEQ ID NO: 8), and CDR3 represented by VGGGDF (SEQ ID NO: 9); and (b) a light chain variable region comprising CDR1 represented by sequence QEISVY (SEQ ID NO: 10), CDR2 represented by sequence GAF (SEQ ID NO: 11), and CDR3 represented by sequence LQYVRYPWT (SEQ ID NO: 12); and an antibody in which one more of CDR sequences are replaced by a homologous sequence(s) both have a binding affinity (KD) for TauC3 of from $1\times10^{-10}$ and $1\times10^{-12}$ and a binding affinity (KD) for FLT of from $1\times10^{-4}$ to $1\times10^{-8}$ M, or no detectable binding with FLT. By definition, homologous antibodies have substantially similar three dimensional shape.

As used herein, "CDR" means "complementary determining region." CDRs may also be referred to as hypervariable regions. Unless otherwise specified, the CDR sequences disclosed herein are defined by IMGT numbering system.

As used herein, "represented by SEQ ID NO:" with reference to the CDR sequence means that the sequence of the CDR is identical or homologous to the recited SEQ ID NO.

The term "chimeric antibody" as used herein refers to an antibody in which the whole of the variable regions of a mouse or rat antibody are expressed along with human constant regions.

The term "murine anti-TauC3 antibody" as used herein refers to the "TauC3 antibody" characterized in Nicholls, S. B., S. L. DeVos, C. Commins, C. Nobuhara, R. E. Bennett, D. L. Corjuc, E. Maury, et al. 2017. "Characterization of TauC3 antibody and demonstration of its potential to block tau propagation." PLoS ONE 12 (5): e0177914. doi: 10.1371/journal.pone.0177914.

As used herein, "light chain" is the small polypeptide subunit of the antibody. A typical antibody comprises two light chains and two heavy chains.

As used herein, the "heavy chain" is the large polypeptide subunit of the antibody. The heavy chain of an antibody contains a series of immunoglobulin domains, with at least one variable domain and at least one constant domain.

The term "affinity" as used herein refers to the strength with which an antibody molecule binds its epitope. The affinity is determined by surface plasmon resonance (SPR) using Biacore kinetics.

The term "KD" as used herein refers to the equilibrium dissociation constant (KD=Kd/Ka, wherein Kd is a dissociation rate constant, and Ka is an association rate constant).

The term "immunodepletion" as used herein refers to the removal of proteins by the use of antibodies. The term "immunodepletion" is used interchangeably with the term "immunoprecipitation." The term refers to the ability of an antibody to pull-down or immunoprecipitate (IP) the antigen of interest from a specimen (which would lead to immunodepletion).

As used herein, the terms "therapeutically effective amount" and "effective amount" means an amount of a therapeutic agent (e.g., an anti-TauC3 antibody) or composition that leads to a measurable clinical effect in a subject. The effective amount of the therapeutic agent is determined by the circumstances surrounding the case, including the compound administered, the route of administration, the status of the symptoms being treated and similar subjects and administration situation considerations among other considerations. An "effective amount" generally comprises from about 0.0001 mg/kg to about 100 mg/kg, preferably from 0.5 mg/kg to 20 mg/kg of the anti-TauC3 antibodies described herein. In certain embodiments, an amount of 1 mg/kg, 3 mg/kg, 4 mg/kg, 6 mg/kg, 8 mg/kg or 10 mg/kg is used.

The term "pathological tau" encompasses TauC3, fibrils comprising TauC3, and aggregates comprising TauC3 (e.g., a heterogeneous population comprising full-length tau, tau oligomers and/or post-translational modified tau (truncated or phosphorylated). In addition to TauC3, pathological tau may comprise heterogeneous population of full-length tau (e.g., 2N4R), tau oligomers and/or post-translationally modified tau (truncated or hyperphosphorylated).

The term "TauC3" means C-terminally truncated tau fragment ending at aspartate 421 of htau40 (SEQ ID NO: 1).

As used herein, "FLT" is an abbreviation for full length Tau (e.g., htau40 (SEQ ID NO: 1)).

The terms "treating" or "treatment" include attenuation, reversal, or improvement in at least one symptom or sign of symptoms associated with a tauopathy.

The term "seeding" refers to extracellular activities that precede intracellular aggregation of TauC3, fibrils comprising TauC3 and/or aggregates comprising TauC3 as part of a heterogeneous population of full-length tau (e.g., 2N4R), tau oligomers and/or post-translationally modified tau (truncated or hyperphosphorylated).

The term "aggregation" refers to the activities that take place intracellularly after TauC3 and/or fibrils comprising TauC3 and/or aggregates comprising TauC3 are taken up by the cell.

"ExpiCHO" is an abbreviation for Chinese Hamster Ovary (CHO High density/serum free) cells.

"A" is an abbreviation for Adenine.

"bp" is an abbreviation for base pairs.

"° C." is an abbreviation for Centigrade.

"C" is an abbreviation for Cytosine.

"MEM" is an abbreviation for Minimal Essential Medium.

"DNA" is an abbreviation for Deoxyribonucleic acid.

"ELISA" is an abbreviation for Enzyme linked immunoadsorbent assay.

"EC50" is an abbreviation for Concentration of antibody providing half-maximal response.

"EC80" is an abbreviation for Concentration of antibody providing 80% of maximal response.

"ECD" is an abbreviation for extracellular domain.

"g" is an abbreviation for grams.

"G" is an abbreviation for Guanine.

"HRP" is an abbreviation for Horseradish peroxidase.

"IgG" is an abbreviation for Immunoglobulin-G.

"K" is an abbreviation for G or T (IUPAC convention).

"LIC" is an abbreviation for Ligase independent cloning.

"min" is an abbreviation for minute.

"M" is an abbreviation for A or C (IUPAC convention).

"nm" is an abbreviation for nanometre.

"OD" is an abbreviation for optical density.

"PBS" is an abbreviation for Phosphate Buffered Saline.

"PCR" is an abbreviation for Polymerase chain reaction.

"R" is an abbreviation for A or G (IUPAC convention).

"RT" is an abbreviation for Room Temperature.

"s" is an abbreviation for second.

"S" is an abbreviation for C or G (IUPAC convention).

"T" is an abbreviation for Thymine.

"TBS" is an abbreviation for Tris Buffered Saline.

"UV" is an abbreviation for Ultra Violet.

"V" is an abbreviation for A or C or G (IUPAC convention).

"VCI" is an abbreviation for vernier, canonical and interface residues.

"VH" is an abbreviation for Immunoglobulin heavy chain variable region.

"VK" is an abbreviation for Immunoglobulin kappa light chain variable region

"W" is an abbreviation for A or T (IUPAC convention).

"Y" is an abbreviation for C or T (IUPAC convention).

DETAILED DESCRIPTION

TauC3 is one of many species present in the high molecular weight species responsible for tau aggregation and seeding activity. In addition to TauC3, tau aggregates may comprise a heterogeneous population of full-length (normal tau), tau oligomers, and/or post-translationally modified tau (truncated or hyperphosphorylated). It has been shown that other neurodegenerative diseases other than sporadic AD also have increased levels of TauC3.

TauC3 is neurotoxic and may cause microtubule dysfunction. TauC3 may also be responsible for spreading of Tau fibrils from one part of the brain to another.

Anti-TauC3 Antibodies

The anti-TauC3 antibodies of the invention recognize an aggregated, extracellular form of pathological TauC3. The anti-TauC3 antibody of the invention may be, e.g., a chimeric, humanized or a human anti-TauC3 antibody.

The anti-TauC3 antibodies show a very tight binding specificity for the target caspase-cleaved Tau protein when tested against the recombinant TauC3 protein. In certain embodiments, the anti-TauC3 antibody blocks seeding in the biosensor assay, and is effective for blocking entry into the neurons of the species responsible for inducing intracellular tau aggregation (i.e., effective for blocking TauC3 and TauC3 fibrils entry into the cells).

The anti-TauC3 antibodies generally have a sub-nanomolar specificity for TauC3 and as is at least 100 times more specific for TauC3 than for full length Tau (2N4R) (e.g., 100-fold or more specific for TauC3 than for full length Tau). For example, the anti-TauC3 antibodies may be from 150 to 5000 times more specific for TauC3 than for full length Tau (2N4R). In certain embodiments, the anti-TauC3 antibodies are from 500 to 2500 times more specific for TauC3 than for full length Tau (2N4R). In certain embodiments, the anti-TauC3 antibodies are from 750 to 2000 times more specific for TauC3 than for full length Tau (2N4R). In certain embodiments, the anti-TauC3 antibodies are from 1000 to 1500 times more specific for TauC3 than for full length Tau (2N4R). In all of these embodiments, the anti-TauC3 antibodies may have no detectable binding with full length Tau (2N4R).

In certain embodiments, the antibody of the invention is a chimeric, humanized or a human anti-TauC3 antibody that has a higher binding affinity (KD) for TauC3 than a murine anti-TauC3 antibody. In some embodiments, chimeric, humanized and human anti-TauC3 antibodies have a binding affinity (KD) for TauC3 that is at least 2-fold higher, 3-fold higher or 4-fold higher than the binding affinity (KD) for TauC3 of a murine anti-TauC3 antibody. In some embodiments, the murine anti-TauC3 antibody has a binding affinity KD for TauC3 of about $4.9 \times 10^{-11}$ M, and the chimeric, humanized and human anti-TauC3 antibody has a binding affinity KD for TauC3 of from about $1 \times 10^{-11}$ M to about $2.5 \times 10^{-11}$ M. The chimeric, humanized and human anti-TauC3 antibody of the invention may have a binding affinity KD for TauC3 of, e.g., about $1.1 \times 10^{-11}$ M, about $1.3 \times 10^{-11}$ M, about $1.5 \times 10^{-11}$ M, about $1.7 \times 10^{-11}$ M, about $1.9 \times 10^{-11}$ M, about $2.1 \times 10^{-11}$ M, or about $2.3 \times 10^{-11}$ M. In some embodiments, the murine anti-TauC3 antibody has a binding affinity KD for TauC3 of about $3.9 \times 10^{-11}$ M, and the chimeric, humanized and human anti-TauC3 antibody has a binding affinity KD for TauC3 of from about $1 \times 10^{-11}$ M to about $2.5 \times 10^{-11}$ M. The chimeric, humanized and human anti-TauC3 antibody of the invention may have a binding affinity KD for TauC3 of, e.g., about $1.1 \times 10^{-11}$ M, about $1.3 \times 10^{-11}$ M, about $1.5 \times 10^{-11}$ M, about $1.7 \times 10^{-11}$ M, about $1.9 \times 10^{-11}$ M, about $2.1 \times 10^{-11}$ M, or about $2.3 \times 10^{-11}$ M.

In certain embodiments, the antibodies bind TauC3 with equilibrium constant KD of from $1 \times 10^{-10}$ M to $1 \times 10^{-11}$ M; and have an equilibrium constant KD with 2N4R which is from $1 \times 10^{-4}$ M to $1 \times 10^{-8}$ M or show no detectible binding with full length Tau (e.g., 2N4R). In the preferred embodiments, the anti-TauC3 antibodies bind TauC3 with an equilibrium constant KD of from $1 \times 10^{-9}$ M to $1 \times 10^{-12}$ M, and bind full length (e.g., 2N4R) with an equilibrium constant KD of from $1 \times 10^{-8}$ M to $9 \times 10^{-8}$ M or show no detectable binding with 2N4R. In some of these embodiments, the antibodies have a very slow off rate from TauC3 (i.e., an off-rate ($K_d$) of from $1 \times 10^{-4}$ to $1 \times 10^{-3}$ s$^{-1}$) and substantially no affinity to 2N4R (i.e., ka of less than 100,000 1/MS).

In certain embodiments, the anti-TauC3 antibody is a chimeric or humanized antibody that has a KD for TauC3 of from about 5 pM to about 90 pM, from about 10 pM to about 90 pM, from about 10 pM to about 80 pM, from about 10 pM to about 70 pM, from about 10 pM to about 60 pM, from about 10 pM to about 50 pM, from about 10 to about 40 pM, or from about 10 pM to about 35 pM.

In certain embodiments, the anti-TauC3 antibody is a chimeric or humanized antibody that has a KD of from about 10 to about 90 pM and a very slow off rate from TauC3, as indicated by $K_d$ of less than $2\times10^{-3}$ s$^{-1}$. In other words, the antibodies have a high degree of specificity to TauC3, the target protein that would be produced in the diseased state, and a slow off rate, both of which are ideal for an antibody to be used in an immunization strategy.

The anti-TauC3 antibodies include but are not limited to monoclonal, chimeric, humanized, single chain, Fab fragments and a Fab expression library. The anti-TauC3 antibodies may be native or recombinant, immobilized, free in solution or displayed on the surface of various molecules or bacteria, viruses, or other surfaces.

In certain embodiments, the anti-TauC3 antibodies recognize sequence SSTGSIDMVD (SEQ ID. No. 23) at the C-terminus of TauC3, but do not recognize the same sequence when it is present internally in FLT.

Anti-TauC3 antibodies useful in accordance with the present invention (e.g. humanized antibodies) may be administered to a subject who may be susceptible to or who is suffering from a tauopathy in order to block seeding and/or aggregation of TauC3 and therefore treat one more symptoms of a tauopathy.

In yet another embodiment of the invention, the anti-TauC3 antibodies of the present invention may be conjugated to a cytoprotective agent or an agent which will facilitate and/or improve antibody's ability to cross the blood-brain barrier ("BBB"). The cytoprotective agent may be an antioxidant (e.g., melatonin); and the agent which facilitates or improves antibody's ability to cross the BBB is a hydrophobic substance which is capable of crossing the BBB, and is generally recognized as sage (GRAS) by the United States Food and Drug Administration ("FDA"). The cytoprotective agent or the agent which facilitates or improves antibody's ability to cross the BBB may be conjugated to the antibody directly or through a linker. The linker may be selected from the group comprising or consisting of a hydrazine linker, a disulfite linker, a thioether linker, a peptide linker. In certain embodiments, the antibody is has equilibrium constant KD to TauC3 that is 2-3 orders of magnitude higher than the antibodies equilibrium constant KD to 2N4R, and the cytoprotective agent is melatonin.

Method of Use

In an aspect, the present invention provides anti-TauC3 antibodies for use in a living human with a tauopathy or at risk of developing a tauopathy. Tauopathies include, e.g., Alzheimer disease (AD), progressive supranuclear palsy (PSP), frontotemporal dementia (FTD), traumatic brain injury (TBI), Pick's disease (PiD), corticobasal degeneration (CBD), frontotemporal lobar degeneration (FTLD), etc.

Methods of Blocking Propagation of Pathological Tau Aggregation

In one aspect, the invention is directed to a method of blocking spreading of pathological tau from one neuron to another or from one part of the brain to another.

In one aspect, the invention is directed to a method of blocking TauC3 seeding activity in the brain of a subject.

In an additional aspect, the invention is directed to a method of reducing the spread of pathological Tau aggregation in the brain of a subject.

The invention is further directed to a method of reducing the spread of aggregates comprising TauC3 in the brain of a subject.

The invention is further directed to a method of reducing the spread of fibrils comprising TauC3 in the brain of a subject.

In a further aspect the invention, the invention is directed to a method of reducing intracellular aggregation of tau induced by intracellular uptake of TauC3 and TauC3 fibrils.

In each aspect, the method comprises administering a therapeutically effective amount of anti-TauC3 antibodies to a human. The anti-TauC3 antibodies are capable of uniquely recognizing an aggregated, extracellular form of pathological tau without binding physiological tau. In a preferred embodiment, an essential part of the epitope of the anti-TauC3 antibodies is the carboxy group forming a neoepitope at the C-terminus residue in a peptide corresponding to the last ten C-terminal residues of TauC3 (e.g., TauC3 or SEQ ID NO: 23). The anti-TauC3 antibodies have equilibrium constant KD to TauC3 that is 2-3 orders of magnitude higher than the antibodies equilibrium constant KD to 2N4R and one or more pharmaceutically acceptable excipient(s). The anti-TauC3 antibodies bind TauC3 with equilibrium constant KD of from $1\times10^{-10}$ M to $1\times10^{-11}$ M, but have an equilibrium constant KD with full length tau (e.g, 2N4R) which is from $1\times10^{-4}$ M to $1\times10^{-8}$ M or show no detectable binding with full length tau (e.g., 2N4R). In the preferred embodiments, the anti-TauC3 antibodies bind TauC3 with an equilibrium constant KD of from $1\times10^{-11}$ M to $9\times10^{-11}$ M, and bind 2N4R with an equilibrium constant KD of from $1\times10^{-8}$ M to $9\times10^{-8}$ M or show no detectable binding with 2N4R. The anti-TauC3 antibodies preferably have a very slow off rate from TauC3 and substantially no affinity to 2N4R (i.e., ka of less than 100,000 1/MS). The antibodies may, e.g., be selected from the humanized antibody, a chimeric antibody or an immunological fragment of any of the foregoing. In the preferred embodiments, the antibody is an antibody selected from the humanized anti-TauC3 antibodies described herein.

A human may or may not be having a symptom associated with tau aggregation prior to administration of a therapeutically effective amount of the anti-TauC3 antibodies. In other words, a human may or may not be experiencing a symptom associated with tau seeding and/or aggregation. One of the ordinary skill in the art will appreciate that pathological tau seeding and aggregation likely commences prior to diagnosis or the onset of symptoms associated with tau aggregation. In some embodiments, a human is having a symptom associated with tau seeding and/or aggregation. In other embodiments, a human is not having a symptom associated with tau seeding and/or aggregation. In still other embodiments, a human has detectable tau pathology but is not having any other symptom associated with tau symptoms and/or aggregation. Reducing the spread of tau aggregation in the brain of a human by administering the therapeutic agents and pharmaceutical compositions according to the invention may reduce the development and/or progression of symptoms associated with the pathological seeding and/or aggregation of tau.

Preventing, inhibiting or slowing down spreading of pathological tau aggregation may therefore be used in the treatment of pathologies associated with generation and spread of tau aggregates. One definition of symptoms associated with tau seeding and/or aggregation refers to any symptom caused by the formation of tau aggregates being composed of, in part, tau fibrils. Exemplary disorders that have symptoms associated with tau aggregation include, but are not limited to, progressive supranuclear palsy, dementia pugilistica (chronic traumatic encephalopathy), frontotemporal dementia and parkinsonism linked to chromosome 17, Lytico-Bodig disease (Parkinson-dementia complex of Guam), tangle-predominant dementia, ganglioglioma and gangliocytoma, meningioangiomatosis, subacute sclerosing panencephalitis, lead encephalopathy, tuberous sclerosis, Hallervorden-Spatz disease, lipofuscinosis, Pick's disease, corticobasal degeneration, argyrophilic grain disease (AGD), Frontotemporal lobar degeneration, Alzheimer's Disease, and frontotemporal dementia. Methods for diagnosing these disorders are known in the art.

Exemplary symptoms associated with tau seeding or aggregation may include, e.g., impaired cognitive function, altered behavior, emotional dysregulation, seizures, and impaired nervous system structure or function. Impaired cognitive function includes but is not limited to difficulties with memory, attention, concentration, language, abstract thought, creativity, executive function, planning, and organization. Altered behavior includes but is not limited to physical or verbal aggression, impulsivity, decreased inhibition, apathy, decreased initiation, changes in personality, abuse of alcohol, tobacco or drugs, and other addiction-related behaviors. Emotional dysregulation includes but is not limited to depression, anxiety, mania, irritability, and emotional incontinence. Seizures include but are not limited to generalized tonic-clonic seizures, complex partial seizures, and non-epileptic, psychogenic seizures. Impaired nervous system structure or function includes but is not limited to hydrocephalus, Parkinsonism, sleep disorders, psychosis, impairment of balance and coordination. This includes motor impairments such as monoparesis, hemiparesis, tetraparesis, ataxia, ballismus and tremor. This also includes sensory loss or dysfunction including olfactory, tactile, gustatory, visual and auditory sensation. Furthermore, this includes autonomic nervous system impairments such as bowel and bladder dysfunction, sexual dysfunction, blood pressure and temperature dysregulation. Finally, this includes hormonal impairments attributable to dysfunction of the hypothalamus and pituitary gland such as deficiencies and dysregulation of growth hormone, thyroid stimulating hormone, lutenizing hormone, follicle stimulating hormone, gonadotropin releasing hormone, prolactin, and numerous other hormones and modulators. Methods for detecting and evaluating symptoms associated with tau aggregation are known in the art.

In some embodiments, a symptom associated with tau aggregation refers to dementia. Dementia is not itself a specific disease, but is an overall term that describes a wide range of symptoms associated with a decline in memory or other thinking skills severe enough to reduce a person's ability to perform everyday activities. Dementia is also a shared clinical feature of many diseases associated with tau aggregation. A skilled practitioner will be familiar with the numerous methods available to diagnose the severity of dementia. For example, several cognitive tests and screening questionnaires for dementia are known in the art, all with varying degrees of sensitivity and specificity. Non-limiting examples include the mini mental state examination (MMSE), the abbreviated mental test may score (AMTS), the modified mini mental state exam (3MS), the cognitive abilities screening instrument (CASI), the Trail-making test, the clock drawing test, the Informant Questionnaire on cognitive decline in the elderly, the General practitioner assessment of cognition, the Clinical Dementia Rating (CDR), Eight-item informant interview to differentiate aging and dementia (AD8).

In some embodiments, the severity of the symptoms of dementia are quantified using the Clinical Dementia Rating. Using the Clinical Dementia Rating, a score of 0 indicates no symptoms, a score of 0.5 indicates very mild symptoms, a score of 1 indicates mild symptoms, a score of 2 indicates moderate symptoms and a score of 3 indicates severe symptoms. Thus, any increase in a Clinical Dementia Rating score for a human indicates a worsening in cognition and an increase in dementia. Moreover, change in Clinical Dementia Rating from 0 to greater than 0, indicates the development or onset of dementia.

In some embodiments, a symptom associated with tau seeding or aggregation refers to tau pathology or a tauopathy. The term "tau pathology" or "tauopathy" refers to the pathological seeding or aggregation of tau. In some embodiments, tau pathology refers to neurofibrially tangles. In other embodiments, tau pathology refers to hyperphosphorylated tau. In still other embodiments, tau pathology refers to a high level of tau aggregates detectable in blood, plasma, serum, CSF, or ISF, anywhere from 2 to approximately 40-fold higher than that detected in individuals without disease.

Administration

Administration of the anti-TauC3 antibodies described herein can be used as a therapy to treat or immunize from tauopathies.

The antibodies in a therapeutically effective amount preferred in pharmaceutical grade, including immunologically reactive fragments, may be administered to a human. Administration is performed using standard effective techniques, include peripherally (i.e. not by administration into the central nervous system) or locally to the central nervous system. Peripheral administration includes but is not limited to intravenous, intraperitoneal, subcutaneous, pulmonary, transdermal, intramuscular, intranasal, buccal, sublingual, or suppository administration. Local administration, including directly into the central nervous system (CNS) includes, but is not limited to, via a lumbar, intraventricular or intraparenchymal catheter or using a surgically implanted controlled release formulation.

Humans amenable to treatment include individuals at risk of disease but not showing symptoms, as well as subjects presently showing symptoms. In the case of Alzheimer's disease, virtually anyone is at risk of suffering from Alzheimer's disease. Therefore, the present methods can be administered prophylactically to the general population without the need for any assessment of the risk of the subject. Such prophylactic administration can begin at, e.g., age 50 or greater. The present methods are especially useful for individuals who do have a known genetic risk of a tauopathy (e.g., Alzheimer's disease). Such individuals include those having relatives who have experienced this disease and those whose risk is determined by analysis of genetic or biochemical markers. For example, genetic markers of risk toward Alzheimer's disease include mutations in the APP gene, particularly mutations, at position 717 and positions 670 and 671 referred to as the Hardy and Swedish mutations respectively. Other markers of risk are mutations in the presenilin genes, PS1 and PS2, and ApoE4, family history of AD, hypercholesterolemia or atherosclerosis. Individuals presently suffering from Alzheimer's disease can be recognized from characteristic dementia by the presence of risk factors described above. In addition, a number of diagnostic tests are available for identifying individuals who have AD. These include imaging, and/or measurement of CSF tau and Aβ42 levels. Elevated tau and decreased Aβ42 levels signify the presence of AD. Individuals suffering from Alzheimer's disease can also be diagnosed by Alzheimer's disease and Related Disorders Association criteria.

In asymptomatic subjects, treatment can begin at any age (e.g., 10, 20, 30, 40, 50, or 60). Usually, however, it is not necessary to begin treatment until a subject reaches 40, 50, 60, 70, 75 or 80. Treatment typically entails multiple dosages over a period of time. Treatment can be monitored by assaying antibody, or activated T-cell or B-cell responses to the therapeutic agent over time. If the response falls, a booster dosage is indicated. In the case of potential Down's syndrome subjects, treatment can begin antenatally by administering therapeutic agent to the mother or shortly after birth.

In prophylactic applications, pharmaceutical compositions or medicaments are administered to a subject susceptible to, or otherwise at risk of a tauopathy in an amount sufficient to eliminate or reduce the risk, lessen the severity, or delay the outset of the disease, including biochemical, histologic and/or behavioral symptoms of the disease, its complications and intermediate pathological phenotypes presented during development of the disease. In therapeutic applications, compositions or medicaments are administered to a subject suspected of, or already suffering from, such a disease in an amount sufficient to cure, or at least partially arrest, the symptoms of the disease biochemical, histologic and/or behavioral), including its complications and intermediate pathological phenotypes in development of the disease. In some methods, administration of agent reduces or eliminates mild cognitive impairment. An amount adequate to accomplish therapeutic or prophylactic treatment is defined as a therapeutically- or prophylactically-effective dose or amount. In both prophylactic and therapeutic regimes, agents are usually administered in several dosages until a sufficient immune response has been achieved. Typically, the immune response is monitored and repeated dosages are given if the immune response starts to wane.

Effective doses of the compositions of the present invention, for the treatment of the above described conditions vary depending upon many different factors, including means of administration, target site, physiological state of the subject, other medications administered, and whether treatment is prophylactic or therapeutic. Treatment dosages need be tested on a case by case basis in clinical trials and often titrated to optimize safety and efficacy. An additional advantage of the anti-TauC3 antibodies of the present invention in certain embodiments may be that, for equal mass dosages, dosages of the anti-TauC3 of the present invention contain a higher molar dosage of the antibodies effective in clearing and/or "inactivating," than a composition comprising antibodies that are less specific for TauC3 than the anti-TauC3 antibodies according to the present invention. Typically, anti-TauC3 antibodies of the present invention would be administered by intravenous infusion or sub cutaneous injection. The amount of the anti-TauC3 antibodies for administration by intravenous infusion may vary from 0.5 to 10 mg per subject. Subcutaneous injections generally require higher doses to reach the brain in sufficient quantity. The antibodies (i.e., whole IgG molecules) may be administered once a month.

In some methods, two or more antibodies (e.g., recombinant, monoclonal, chimeric and/or humanized) with the same or different binding specificities are administered simultaneously, in which case the dosage of each antibody administered falls within the ranges indicated. In such circumstances, the two or more antibodies may both be directed at, e.g., truncated tau. Alternatively, one or more of the antibodies may be directed at, e.g., truncated tau, and one or more additional antibodies may be directed at amyloid-β (AB) peptides associated with Alzheimer's disease. Antibodies are usually administered on multiple occasions. Intervals between single dosages can be hourly, daily, weekly, monthly, or yearly. In some methods, dosage is adjusted to achieve a plasma antibody concentration of 1-1000 μg/ml and in some methods 25-300 μg ml. Alternatively, antibody can be administered as a sustained release formulation, in which case less frequent administration is required.

Dosage and frequency vary depending on the half-life of the antibody in the subject. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some subjects continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the patent can be administered a prophylactic regime.

The dose of the anti-TauC3 antibodies to block TauC3 seeding is not necessarily the same as the dose of the anti-TauC3 antibodies to inhibit TauC3 aggregation. In view of the information provided in the present specification, the specific doses can be determined by routine experimentation.

The efficacy of the administration/treatment may be accessed by measuring levels of pathogenic tau or phospho tau in plasma and/or CSF. Based on this assessment, the dose and/or frequency of administration may be adjusted accordingly.

In certain embodiments, effect on cognition may also be accessed.

The efficacy may also be accessed by a degree of brain atrophy, as determined by MRI.

The safety of the administration/treatment may be accessed by number of participants experiencing adverse events (AEs), serious AEs, and abnormalities in clinical laboratory tests, vital signs, ECGs, MRI, and physical and neurological exams as well as worsening of cognition. Based on this assessment, the dose and/or frequency of administration may be adjusted accordingly.

The anti-TauC3 antibodies and immunogens may be administered intranasally, by a subcutaneous injection, intramuscular injection, IV infusion, transcutaneously, buccally, etc., or as described in more detail below.

Pharmaceutical Compositions

Pharmaceutical compositions in accordance with the invention comprise the anti-TauC3 antibodies described herein, or fragments thereof, and one or more pharmaceutically acceptable excipients. The anti-TauC3 antibodies bind TauC3 with equilibrium constant KD of from $1 \times 10^{-10}$ M to $1 \times 10^{-11}$ M, but have an equilibrium constant KD with full length tau (e.g., 2N4R) which is from $1 \times 10^{-4}$ M to $1 \times 10^{-8}$ M or show no detectible binding with full length tau (e.g., 2N4R). In the preferred embodiments, the anti-TauC3 antibodies bind TauC3 with an equilibrium constant KD of from $1 \times 10^{-11}$ M to $9 \times 10^{-11}$ M, and bind 2N4R with an equilibrium constant KD of from $1 \times 10^{-8}$ M to $9 \times 10^{-8}$ M or show no detectable binding with 4RTau. The anti-TauC3 antibodies preferably have a very slow off rate from TauC3 (i.e., an off-rate from $1 \times 10^{-4}$ to $1 \times 10^{-3}$ $s^{-1}$) and substantially no affinity to 4RTau (i.e., ka of less than 100,000 1/MS). The antibodies may, e.g., be humanized, chimeric or human (e.g., from tg mice) antibodies.

The pharmaceutical compositions are designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate.

Effective peripheral systemic delivery by intravenous or subcutaneous injection is a preferred method of administration to a living subject. Suitable vehicles for such injections are straightforward.

The concentration of humanized antibody in formulations to be administered is an effective amount and ranges from as low as about 0.1% by weight to as much as about 95 or about 99.9% by weight and will be selected primarily based on fluid volumes, viscosities, and so forth, in accordance with the particular mode of administration selected if desired. In certain embodiments, the antibodies may comprise from about 15 or about 20% by weight of the composition.

A composition for injection to a subject could be made up to contain from 1-250 ml sterile buffered water of phosphate buffered saline and about 1-5000 mg of any one of or a combination of the anti-TauC3 antibodies of the present invention. The formulation could be sterile filtered after making the formulation, or otherwise made microbiologically acceptable. A typical composition for intravenous infusion could have volumes between 1-250 ml of fluid, such as sterile Ringer's solution, and 1-100 mg per ml, or more in anti-tau antibody concentration. Therapeutic agents of the discovery can be frozen or lyophilized for storage and reconstituted in a suitable sterile carrier prior to use. Lyophilization and reconstitution may lead to varying degrees of antibody activity loss (e.g. with conventional immune globulins, IgM antibodies tend to have greater activity loss than IgG antibodies).

Dosages administered are effective amounts for the purposes indicated and may have to be adjusted to compensate. The pH of the formulations that are generally of pharmaceutical grade quality will be selected to balance antibody stability (chemical and physical) and comfort to the subject when administered. Generally, a pH between 4 and 8 is tolerated. Doses will vary from individual to individual based on size, weight, and other physiobiological characteristics of the individual receiving the successful administration.

In an aspect, a typical dose contains from about 0.1 mg to about 10 mg anti-TauC3 antibodies described herein. In certain embodiments, the typical dose contains from about 0.5 mg to about 10 mg of the anti-TauC3 antibodies. Doses can range from about 0.55 mg/kg to about 10 mg/kg. The frequency of dosing with whole IgG antibodies is usually per month whereas antibody fragments need to be dosed more often in view of their shorter half-life, as needed as to effectively treat the symptoms.

The timing of administration of the treatment relative to the disease itself and duration of treatment will be determined by the circumstances surrounding the case. Treatment could begin after diagnosis of a disease associated with tau aggregation. Alternatively, treatment could begin after clinical confirmation of a symptom associated with tau aggregation. Further still, treatment could begin after detection of tau pathology. Treatment could begin immediately in a hospital or clinic, or at a later time after discharge from the hospital or after being seen in an outpatient clinic. Duration of treatment could range from a single dose administered on a one-time basis to a life-long course of therapeutic treatments.

Although the foregoing methods appear the most convenient and most appropriate and effective for administration of proteins such as humanized antibodies, by suitable adaptation, other effective techniques for administration, such as intraventricular administration, transdermal administration and oral administration may be employed provided proper formulation is utilized herein.

Typical effective amounts or doses can be determined and optimized using standard clinical techniques and will be dependent on the mode of administration in view of the information provided herein and knowledge available in the art.

Example 1 (Sequence Determination of Mouse MoTau01 Antibody)

Sequence Determination of the MoTau01 Antibody

RNA Preparation from Hybridoma Cells.

Frozen pellets of mouse hybridoma cells (MoTau01), which were stored at −80° C., were supplied by Genscript on behalf of Tau-Biologic and processed using the Qiagen RNeasy Kit to isolate RNA following the manufacturer's protocol.

$1^{st}$ Strand cDNA Synthesis

MoTau01 RNA (~21 µg) was reverse-transcribed to produce cDNA using the GE Life Sciences $1^{st}$ strand cDNA synthesis kit following the manufacturer's protocol and purified as described in Example 5. This was repeated twice to generate 3 independent cDNA products (rounds 1, 2 and 3) in order to detect and avoid cDNA mutations induced by the Reverse Transcriptase.

cDNA Sequence Determination

The MoTau01 cDNA was amplified by PCR as described in Example 5.

Immunoglobulin cDNA was PCR-amplified with kappa light chain primers plus MKC (Table 1) or heavy chain primers (1-12 and 14) plus MHC mix (Table 2) using the Phusion Flash High-Fidelity PCR Master Mix. The MoTau01 VH PCR primer sets failed to produce any products.

Therefore, additional primers were designed based on the known sequence in the leader and terminal regions, in order to facilitate cloning the VH domain from the hybridoma cells. The additional primer sequences are included in the primer table as MHV13 and in the 'additional primers' section (Table 2).

TABLE 1

| PCR primers for amplifying mouse VK | |
|---|---|
| Name | Sequence (5' → 3') |
| MKV1 | TGTAAAACGACGGCCAGTATGAAGTTGCCTGTTAGGCTGTTGG TGCTG (SEQ ID NO: 20) |
| MKV2 | TGTAAAACGACGGCCAGTATGGAGWCAGACACACTCCTGYTAT GGGTG (SEQ ID NO: 21) |

TABLE 1-continued

PCR primers for amplifying mouse VK

| Name | Sequence (5' → 3') |
|---|---|
| MKV3 | TGTAAAACGACGGCCAGTATGAGTGTGCTCACTCAGGTCCTGG SGTTG (SEQ ID NO: 22) |
| MKV4 | TGTAAAACGACGGCCAGTATGAGGTCCCCTGCTCAGWTTYTTG GMWTCTTG (SEQ ID NO: 23) |
| MKV5 | TGTAAAACGACGGCCAGTATGGATTTWAGGTGCAGATTWTCAG CTTC (SEQ ID NO: 24) |
| MKV6 | TGTAAAACGACGGCCAGTATGAGGTKCKKTGKTSAGSTSCTGR GG (SEQ ID NO: 25) |
| MKV7 | TGTAAAACGACGGCCAGTATGGGCWTCAAGATGGAGTCACAKW YYCWGG (SEQ ID NO: 26) |
| MKV8 | TGTAAAACGACGGCCAGTATGTGGGGAYCTKTTTYCMMTTTTT CAATTG (SEQ ID NO: 27) |
| MKV9 | TGTAAAACGACGGCCAGTATGGTRTCCWCASCTCAGTTCCTTG (SEQ ID NO: 28) |
| MKV10 | TGTAAAACGACGGCCAGTATGTATATATGTTTGTTGTCTATTT CT (SEQ ID NO: 29) |
| MKV11 | TGTAAAACGACGGCCAGTATGGAAGCCCCAGCTCAGCTTCTCT TCC (SEQ ID NO: 30) |
| CL12A | TGTAAAACGACGGCCAGTATGRAGTYWCAGACCCAGGTCTTYR T (SEQ ID NO: 31) |
| CL12B | TGTAAAACGACGGCCAGTATGGAGACACATTCTCAGGTCTTTG T (SEQ ID NO: 32) |
| CL13 | TGTAAAACGACGGCCAGTATGGATTCACAGGCCCAGGTTCTTA T (SEQ ID NO: 33) |
| CL14 | TGTAAAACGACGGCCAGTATGATGAGTCCTGCCCAGTTCCTGT T (SEQ ID NO: 34) |
| CL15 | TGTAAAACGACGGCCAGTATGAATTTGCCTGTTCATCTCTTGG TGCT (SEQ ID NO: 35) |
| CL16 | TGTAAAACGACGGCCAGTATGGATTTTCAATTGGTCCTCATCT CCTT (SEQ ID NO: 36) |
| CL17A | TGTAAAACGACGGCCAGTATGAGGTGCCTARCTSAGTTCCTGR G (SEQ ID NO: 37) |
| CL17B | TGTAAAACGACGGCCAGTATGAAGTACTCTGCTCAGTTTCTAG G (SEQ ID NO: 38) |
| CL17C | TGTAAAACGACGGCCAGTATGAGGCATTCTCTTCAATTCTTGG G (SEQ ID NO: 39) |
| MKC | CAGGAAACAGCTATGACCACTGGATGGTGGGAAGATGG (SEQ ID NO: 40) |

Ambiguity codes: W = A or T; Y = C or T; K = G or T

MKV indicates primer that hybridizes to leader sequences of the mouse kappa light chain variable region genes; MKC indicates the primer that hybridizes to the mouse kappa constant region gene. Bold underlined section indicates the M13 Forward or the M13 Reverse Sequencing Primer. Wobble bases are defined in the Definitions section.

TABLE 2

PCR primers for amplifying mouse VH

| Name | Sequence (5' → 3') |
|---|---|
| MHV1 | TGTAAAACGACGGCCAGTATGAAATGCAGCTGGGGCA TSTTCTTC (SEQ ID NO: 41) |
| MHV2 | TGTAAAACGACGGCCAGTATGGGATGGAGCTRTATCA TSYTCTT (SEQ ID NO: 42) |
| MHV3 | TGTAAAACGACGGCCAGTATGAAGWTGTGGTTAAACT GGGTTTTT (SEQ ID NO: 43) |
| MHV4 | TGTAAAACGACGGCCAGTATGRACTTTGGGYTCAGCT TGRTTT (SEQ ID NO: 44) |
| MHV5 | TGTAAAACGACGGCCAGTATGGACTCCAGGCTCAATT TAGTTTTCCTT (SEQ ID NO: 45) |
| MHV6 | TGTAAAACGACGGCCAGTATGGCTGTCYTRGSGCTRC TCTTCTGC (SEQ ID NO: 46) |
| MHV7 | TGTAAAACGACGGCCAGTATGGRATGGAGCKGGRTCT TTMTCTT (SEQ ID NO: 47) |
| MHV8 | TGTAAAACGACGGCCAGTATGAGAGTGCTGATTCTTT TGTG (SEQ ID NO: 48) |
| MHV9 | TGTAAAACGACGGCCAGTATGGMTTGGGTGTGGAMCT TGCTATTCCTG (SEQ ID NO: 49) |
| MHV10 | TGTAAAACGACGGCCAGTATGGGCAGACTTACATTCT CATTCCTG (SEQ ID NO: 50) |
| MHV11 | TGTAAAACGACGGCCAGTATGGATTTTGGGCTGATTT TTTTTATTG (SEQ ID NO: 51) |
| MHV12 | TGTAAAACGACGGCCAGTATGATGGTGTTAAGTCTTC TGTACCTG (SEQ ID NO: 52) |
| MHV13 | TGTAAAACGACGGCCAGTATGACATTGAACATGCTGT TGGGGC (SEQ ID NO: 140) |
| MHV14 | TGTAAAACGACGGCCAGTATGAACAGGCTTACTTCCT CATTGCTGCTGC (SEQ ID NO: 53) |
| MHCG1 | CAGGAAACAGCTATGACCCAGTGGATAGACAGATGGG GG (SEQ ID NO: 54) |
| MHCG2a | CAGGAAACAGCTATGACCCAGTGGATAGACCGATGGG GC (SEQ ID NO: 55) |
| MHCG2b | CAGGAAACAGCTATGACCCAGTGGATAGACTGATGGG GG (SEQ ID NO: 56) |
| MHCG3 | CAGGAAACAGCTATGACCCAAGGGATAGACAGATGGG GC (SEQ ID NO: 57) |
| Additional Primers | |
| M13T100VHFor | TGTAAAACGACGGCCAGTGAGGTGCAGGTTGTTGAGT CTGG (SEQ ID NO: 58) |
| M13T100VHRev | TGTAAAACGACGGCCAGTGAGGTGCAGGTTGTTGAGT CTGG (SEQ ID NO: 139) |

Ambiguity codes: R = A or G; K = G or T; M = A or C.

MHV indicates primers that hybridize to the leader sequences of mouse heavy chain variable region genes.

MHCG indicates primers that hybridize to the mouse constant region genes. Bold underlined section indicates the M13 Forward or the M13 Reverse Sequencing Primer. Primer MHC mix consists of an equimolar mix of primers MHCG1, MHCG2a, MHCG2b and MHCG3. 'Wobble' bases are defined in the Definitions section.

The result of each PCR reaction was a single amplification product that was purified using the QIAquick PCR purification kit and sequenced (by Eurofins/GATC Genomics) in both directions using the M13-Forward and M13-Reverse primers (Table 3) to obtain three independent sets of sequence information for each immunoglobulin chain.

TABLE 3

General PCR and Sequencing primers

| Name | Sequence (5' → 3') |
|---|---|
| HCMVi promoter | TGTTCCTTTCCATGGGTCTT (SEQ ID NO: 59) |
| HuG4_LIC_Rev | CTCTCGGAGGTGCTCCTGGAG (SEQ ID NO: 60) |
| HuK_LIC_Rev | GCAGTTCCAGATTTCAACTG (SEQ ID NO: 61) |
| M13-Forward | TGTAAAACGACGGCCAGT (SEQ ID NO: 62) |
| M13-Reverse | CAGGAAACAGCTATGACC (SEQ ID NO: 63) |

VK and VH MoTau01 DNA Sequence

Figure 1:
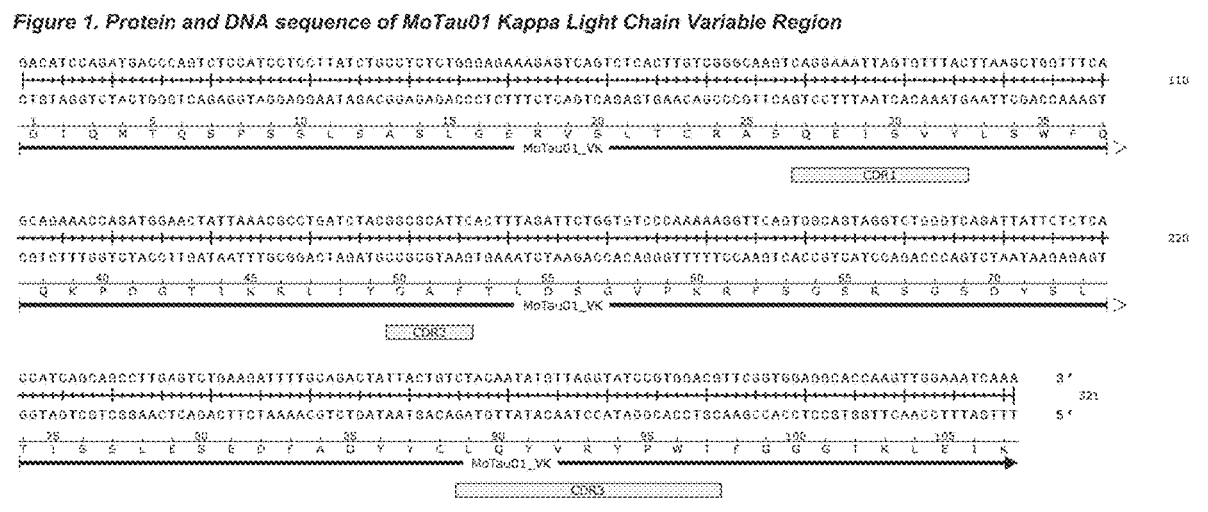

The consensus DNA sequence of the MoTau01 VK PCR product and the MoTau01 $V_H$ PCR product are shown in FIGS. 1 and 2 respectively. The variable region DNA sequences obtained were identical to the sequences determined by Genscript. Germ Line Analysis of the MoTau01 sequences show that the Kappa Light Chain is a Murine VK1 IGKV9-124*01 and the Heavy Chain is a Murine VH1 IGHV10-1*02.

Example 2 (Generation of a Chimeric MoTau01 Antibody)

Construction of the Chimeric MoTau01 Expression Vectors

The genes for MoTau01 VH and VK were synthesized by GenScript. Using software algorithms proprietary to GenScript, the sequences for MoTau01 $V_H$ and VK were optimized by silent mutagenesis to use codons preferentially utilized by human cells and synthesized.

Construction of chimeric expression vectors entails cloning the synthesized variable regions into IgG/kappa vectors (pHuK and pHuG4—FIGS. 3 and 4 respectively), using ligase-independent cloning (LIC). The vectors (pCMV modified) are digested with BfuA1 (BspM1) and then compatible overhangs are generated with T4 DNA polymerase 3'-5' exonuclease activity (+dATP).

Figure 5:
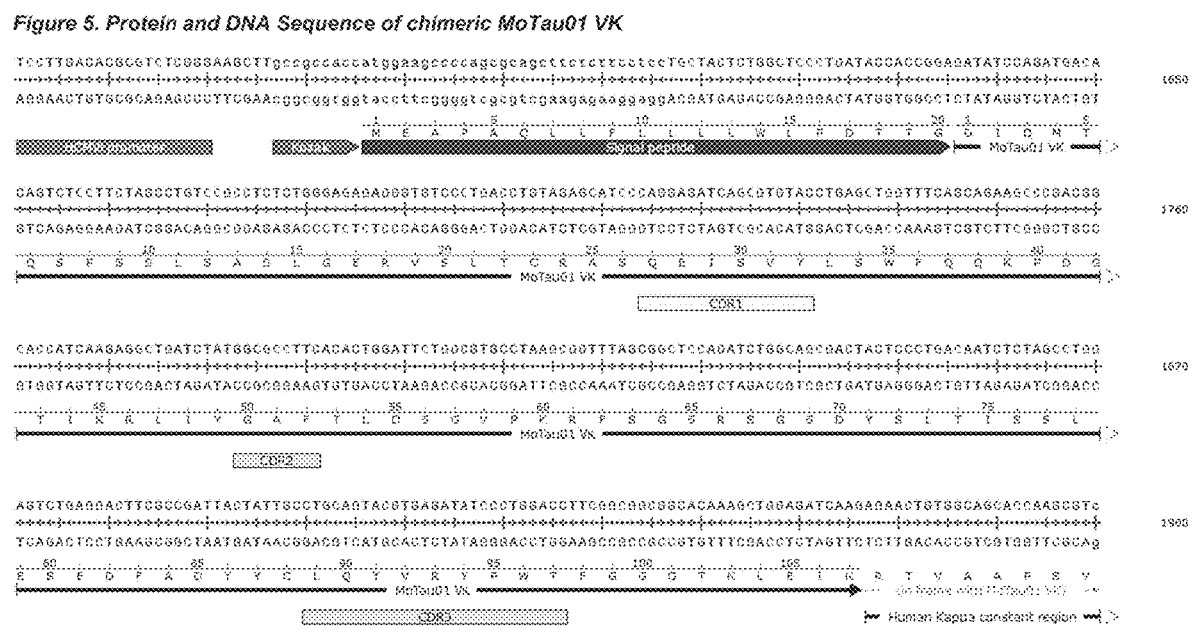
Figure 6:
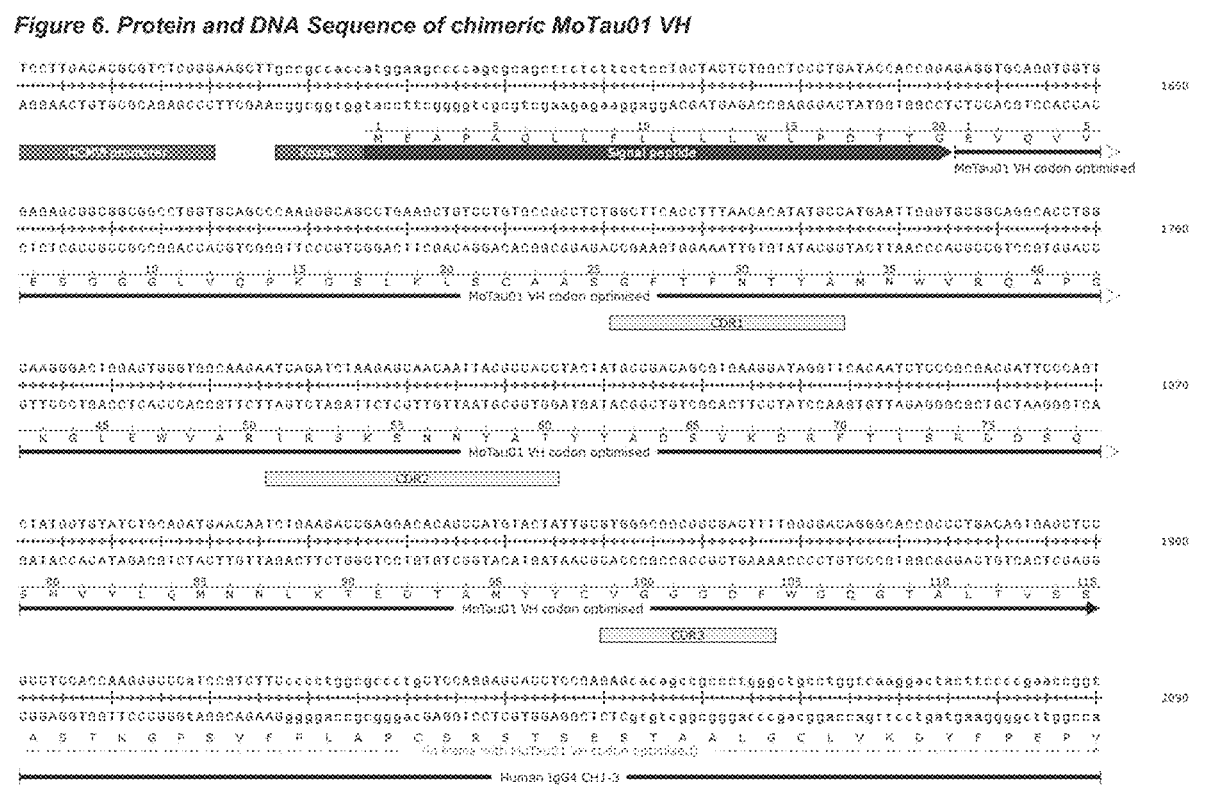

The antibody sequences (FIGS. 5 and 6) are generated by firstly amplifying the synthesized variable regions by PCR with primers containing the 3' end of the leader sequence (most of the sequence is present in the vector)—forward primer—or the beginning of the constant region (IgG4 or kappa)—reverse primer—, followed by the beginning of the variable region (in each direction), Table 4.

TABLE 4

Cloning and mutagenesis primers

| Name | Sequence (5' → 3') |
|---|---|
| MoTau01 VH LIC For | CTCTGGCTCCCTGATACCACCGGAGAGGTGCAGGTGGTG GAGAGC (SEQ ID NO: 64) |
| MoTau01 VK LIC For | CTCTGGCTCCCTGATACCACCGGAGATATCCAGATGACA CAGTCT (SEQ ID NO: 65) |
| MoTau01 VH LIC HuG4 Rev | GGGCCCTTGGTGGAGGCGGAGCTCACTGTCAGGGCGGT (SEQ ID NO: 66) |
| MoTau01 VK LIC Huk Rev | CGCTTGGTGCTGCCACAGTTCTCTTGATCTCCAGCTTTG TGCCG (SEQ ID NO: 67) |
| Tau01 HA/HC LIC For | CTCTGGCTCCCTGATACCACCGGACTGGTGCAGCTGGTG GAAAGCG (SEQ ID NO: 68) |
| Tau01 HB LIC For | CTCTGGCTCCCTGATACCACCGGAGAGGTGCAGGTGGTG GAAAGCG (SEQ ID NO: 69) |
| Tau01 HA-HC_HuG 4 Rev | GGGCCCTTGGTGGAGGCGGAGCTCACTGTCACCAGGGTG (SEQ ID NO: 70) |
| Tau01 HD mutation L-E For | cctgatacCACCGGAGAGGTGCAGCTGGTG (SEQ ID NO: 71) |
| Tau01 HD mutation L-E Rev | CACCAGCTGCACCTCTCCGGTGgtatcagg (SEQ ID NO: 72) |
| Tau01 HE mutation L-V For | CGGACTGGTGCAGGTGGTGGAAAGCGG (SEQ ID NO: 73) |
| Tau01 HE mutation L-V Rev | CCGCTTTCCACCACCTGCACCAGTCCG (SEQ ID NO: 74) |
| Tau01 HF mutation H-N For | TTTAACACATATGCAATGAACTGGGTGCGGCAGG (SEQ ID NO: 75) |
| Tau01 HF mutation H-N Rev | CCTGCCGCACCCAGTTCATTGCATATGTGTTAAA (SEQ ID NO: 76) |
| Tau01 HG mutation G-A For | CTGGAGTGGGTGGCCCGGATCAGATCT (SEQ ID NO: 77) |
| Tau01 HG mutation G-A Rev | AGATCTGATCCGGGCCACCCACTCCAG (SEQ ID NO: 78) |
| Tau01 HH | CTAAGAGCAACAATTATGCAACATATTATGCAGCATCTG TGAAGGGCAG |

TABLE 4-continued

Cloning and mutagenesis primers

| Name | Sequence (5' → 3') |
|---|---|
| mutation A-Y For | (SEQ ID NO: 79) |
| Tau01 HH mutation A-Y Rev | CTGCCCTTCACAGATGCTGCATAATATGTTGCATAATTG TTGCTCTTAG (SEQ ID NO: 80) |
| Tau01 HI mutation A-D For | TATGCAACAGCATATGCAGATTCTGTGAAGGGCAGGTTC A (SEQ ID NO: 81) |
| Tau01 HI mutation A-D Rev | TGAACCTGCCCTTCACAGAATCTGCATATGCTGTTGCAT A (SEQ ID NO: 82) |
| Tau01 HJ mutation N-S For | CCGCGACGATTCTAAGAGTACAGCCTATCTGCAGA (SEQ ID NO: 83) |
| Tau01 HJ mutation N-S Rev | TCTGCAGATAGGCTGTACTCTTAGAATCGTCGCGG (SEQ ID NO: 84) |
| Tau01 HK mutation T-M For | TCTCCCGCGACGATTCTAAGAATATGGCCTATCTGCAGA T (SEQ ID NO: 85) |
| Tau01 HK mutation T-M Rev | ATCTGCAGATAGGCCATATTCTTAGAATCGTCGCGGGAG A (SEQ ID NO: 86) |
| Tau01 HL mutation A-V For | GACGATTCTAAGAATACAGTCTATCTGCAGATGGACTCC (SEQ ID NO: 87) |
| Tau01 HL mutation A-V Rev | GGAGTCCATCTGCAGATAGACTGTATTCTTAGAATCGTC (SEQ ID NO: 88) |
| Tau01 KA/KC LIC For | CTCTGGCTCCCTGATACCACCGGAGACATCCAGATGACC CAGTCTC (SEQ ID NO: 89) |
| Tau01 LB LIC For | CTCTGGCTCCCTGATACCACCGGAGACATCCAGATGACA CAGTCTC (SEQ ID NO: 90) |
| Tau01 KA-KC LIC Huk Rev | CGCTTGGTGCTGCCACAGTTCTCTTGATCTCCACCTTTG TGCCG (SEQ ID NO: 91) |
| Tau01 KD mutation G-S For | GATCTCCGTGTACCTGAGCTGGTATCAGCAGAA (SEQ ID NO: 141) |
| Tau01 KD mutation G-S Rev | TTCTGCTGATACCAGCTCAGGTACACGGAGATC (SEQ ID NO: 92) |
| Tau01 KE mutation Y-F For | TGTACCTGGGCTGGTTTCAGCAGAAGCCC (SEQ ID NO: 93) |
| Tau01 KE mutation Y-F Rev | GGGCTTCTGCTGAAACCAGCCCAGGTACA (SEQ ID NO: 94) |
| Tau01 KF mutation P-I For | GAAGCCCGGCAAGGCCATTAAGCGGCTGATCTAC (SEQ ID NO: 95) |
| Tau01 KF mutation P-I Rev | GTAGATCAGCCGCTTAATGGCCTTGCCGGGCTTC (SEQ ID NO: 96) |
| Tau01 KG mutation K-T For | ATCTACGGCGCCTTCACGCTGCAGTCCG (SEQ ID NO: 97) |
| Tau01 KG mutation K-T Rev | CGGACTGCAGCGTGAAGGCGCCGTAGAT (SEQ ID NO: 98) |
| Tau01 KH mutation T-S For | GGATCCAGATCTGGCAGCGAGTTTACCCTGA (SEQ ID NO: 99) |
| Tau01 KH mutation T-S Rev | TCAGGGTAAACTCGCTGCCAGATCTGGATCC (SEQ ID NO: 100) |
| Tau01 KI mutation F-Y For | CAGATCTGGCACCGAGTATACCCTGACAATCTCTA (SEQ ID NO: 101) |
| Tau01 KI mutation F-Y Rev | TAGAGATTGTCAGGGTATACTCGGTGCCAGATCTG (SEQ ID NO: 102) |
| Tau01 KJ mutation K-S For | CTACGGCGCCTTCAGCCTGCAGTCCGGAGT (SEQ ID NO: 103) |
| Tau01 KJ mutation K-S Rev | ACTCCGGACTGCAGGCTGAAGGCGCCGTAG (SEQ ID NO: 104) |

The complementary overhangs were generated in the PCR products by T4 DNA polymerase+dTTP treatment (the protocol is provided in Example 5). Vector and inserts were incubated at RT, transformed into chemically-competent TOP10 bacteria and plated on Kanamycin plates. Several clones were isolated and colonies screened by PCR using primers HCMVi promotor forward and HuG4 LIC Rev for VH or HuK LIC Rev for VK (Table 3).

The clones generating the correct sized PCR products were selected, miniprepped using the QIAGEN kit and sequenced using the same primers.

Generation of the Chimeric Antibodies

ExpiCHO suspension cells growing in ExpiCHO transfection medium and antibiotics were co-transfected with MoTau01_VH.pHuG4 and MoTau01_VK.pHuK (1 µg DNA each) using ExpiFectamine CHO Reagent. The cells were grown in 1 mL growth medium for 7 days. Up to 160 µg/mL (Table 14 A) of MoTau01 HuG4k antibody was measured in the conditioned medium by Octet quantitation.

TauC3 Binding Activity of Chimeric Antibodies

Figure 7B:
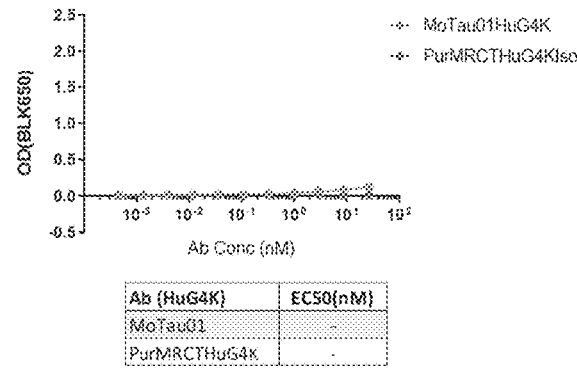
Figure 8A:
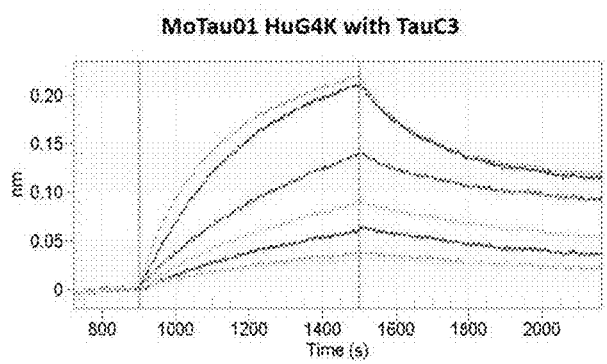
FIGS. 8A to 8D. Binding test of murine and chimeric Tau01 antibodies to TauC3 and FL Tau using the Octet.
Figure 8B:
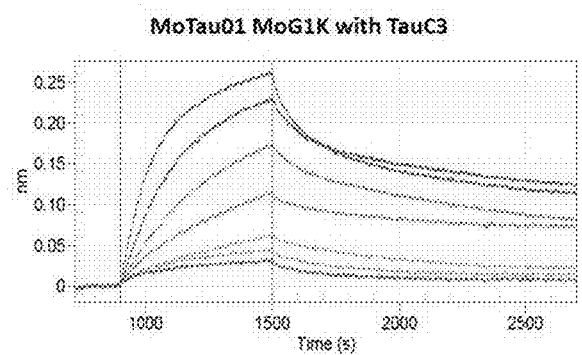
Figure 8C:
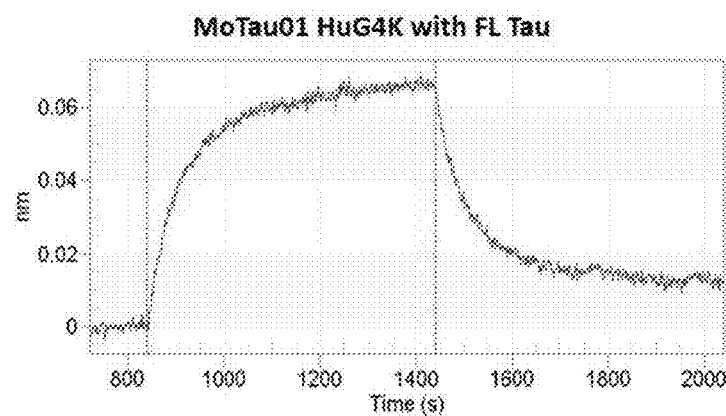
Figure 8D:
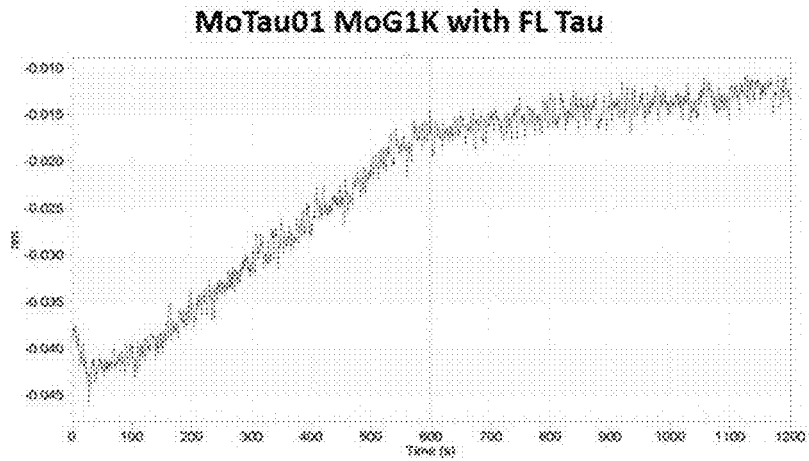

The TauC3 and FL Tau antigens were generated and purified by Genscript and supplied at a concentration of 2.54 mg/ml or 0.24 mg/ml respectively. Binding of the chimeric antibody to TauC3 and FL Tau was assayed by binding ELISA. The chimeric antibody was able to bind to TauC3 with an EC50 of 0.7 nM (FIG. 7 A) but no binding could be observed to FL Tau (FIG. 7 B). No non-specific binding to either antigen could be observed with an isotype confirming the binding observed is specific. Binding of the mouse and chimeric Tau01 antibodies to purified TauC3, was measured using Bio-Layer Interferometry (OctetRed96, ForteBio Section 8.12). The mouse and chimeric antibodies were assayed against a concentration series from 20 nM-0.31 nM TauC3 (FIGS. 8 A and B). Both the mouse and chimeric antibodies were capable of binding to TauC3 in a concentration-dependent manner. The binding of the mouse and chimeric antibodies was also tested against FL Tau but low signals or no binding was observed (FIGS. 8 C and D) confirming the binding of the antibodies is specific to TauC3.

Example 3 Design of Tau01 Humanized Antibody Variants

Human VH and VK cDNA Databases

The protein sequences of human and mouse immunoglobulins from the International Immunogenetics Database 2009 (Lefranc, 2015) and the Kabat Database Release 5 of Sequences of Proteins of Immunological Interest (last update 17 Nov. 1999)(Kabat et al. 1991) were used to compile a database of aligned human immunoglobulin sequences. The database contains 10,406 VH and 2,894 VK sequences.

Molecular Model of MoTau01

The MoTau01 VH and VK sequences were used to design the humanized version of MoTau01 antibody. A homology model of MoTau01 antibody variable regions has been generated using the antibody prediction panel in Maestro 11.5. The chosen human framework was used to generate 10 loop models, which were prepared using the one-step protein preparation wizard. Protein reliability reports were generated for all 10 models and no major differences could be identified in model quality. All 10 models were used to determine a consensus of residues which were within 4 Å of the CDR loops, in order to capture different orientations of the CDRs.

Human Framework Selection

Humanization requires the identification of suitable human V regions. The sequence analysis program, Gibbs, was used to interrogate the human VH and VK databases with MoTau01 VH and VK protein sequences using various selection criteria. Using the Maestro 11.5 (Schrödinger) software, FW residues within 4 Å of the CDR residues (IMGT definition) in the structures of mouse Tau01 antibody were identified, and designated as the "4 Å Proximity Residues". Human VH sequence alignments with highest identity to MoTau01 VH in the 4 Å Proximity Residues are shown in Table 5. Table 6 lists these envelope residues and VCIs, and the number of residues in either the FW, VCI or 4 Å Proximity Residues which are identical to the mouse equivalent position for the sequences in Table 5.

Humanized sequences and incomplete sequences were removed from the analysis. The sequence DQ840895.1 was chosen as the human heavy chain donor candidate. This sequence scores high in sequence identity and similarity, and has only 2 somatic mutations from its IGHV3-73*01 VH germline. It has eight 4 Å proximity and one VCI residue change but this was the minimal number of changes obtainable (Table 8).

TABLE 8

Tau01 Heavy Chain Humanization Strategy

```
Sequence
         1         2         3         4         5
         7         8         9        10
                            11
1234567890123456789012345678901 2345ABCD67890123456789012ABCD3
4567890123456789012345678901 2ABC3456789012 34567890
Name     ABCDEFGHIJKLMNOPQRSTUV1234567890123

MoTau01 VH   EVQVVESGGGLVQPKGSLKLSCAASGFTFNT----YAMNWVRQAPGKGLEWVARIRSKS-
             NNYATYYADSVKDRFTISRDDSQSMVYLQMNNLKTEDTAMYYCVGGG-------------
             --------------DFWGQGTALTVSS (SEQ ID NO: 105)

DQ840895.1   LVQLVESGGGLVQPGGSLKLSCAASGFTF----
             SGSAMHWVRQASGKGLEWVGRIRSKA-
             NSYATAYAASVKGRFTISRDDSKNTAYLQMDSLKTEDTAVYYCTTY----
             ---------------------EGWGQGTLVTVSS (SEQ ID NO: 106)

Tau01 HA     LVQLVESGGGLVQPGGSLKLSCAASGFTFNT----
             YAMHWVRQASGKGLEWVGRIRSKS-
             NNYATAYAASVKGRFTISRDDSKNTAYLQMDSLKTEDTAVYYCVGGG----
             ---------------------DFWGQGTLVTVSS (SEQ ID NO: 107)
```

TABLE 8-continued

Tau01 Heavy Chain Humanization Strategy

```
           Sequence
                  1         2         3         4         5
                       7         8         9        10
                                          11
           1234567890123456789012345678901234ABCD67890123456789012ABC
           D3
           4567890123456789012345678901 2ABC345678901234567890
Name       ABCDEFGHIJKLMNOPQRSTUV1234567890123
```

| Name | Sequence |
|---|---|
| Tau01 HB | EVQVVESGGGLVQPGGSLKLSCAASGFTFNT---- YAMNWVRQASGKGLEWVARIRSKS- NNYATYYA*DS*VKGRFTISRDDSK*SMV*YLQMNDSLKTEDTAVYYCVGGG---- ---------------------DFWGQGTLVTVSS (SEQ ID NO: 108) |
| Tau01 HC | LVQLVESGGGLVQPGGSLKLSCAASGFTFNT---- YAMNWVRQASGKGLEWVGRIRSKS- NNYATYYAASVKGRFTISRDDSK*SM*AYLQMDSLKTEDTAVYYCVGGG---- ---------------------DFWGQGTLVTVSS (SEQ ID NO: 109) |
| Tau01 HD | *E*VQLVESGGGLVQPGGSLKLSCAASGFTFNT---- YAMHWVRQASGKGLEWVGRIRSKS- NNYATAYAASVKGRFTISRDDSKNTAYLQMDSLKTEDTAVYYCVGGG---- ---------------------DFWGQGTLVTVSS (SEQ ID NO: 110) |
| Tau01 HE | LVQ*V*VESGGGLVQPGGSLKLSCAASGFTFNT---- YAMHWVRQASGKGLEWVGRIRSKS- NNYATAYAASVKGRFTISRDDSKNTAYLQMDSLKTEDTAVYYCVGGG---- ---------------------DFWGQGTLVTVSS (SEQ ID NO: 111) |
| Tau01 HF | LVQLVESGGGLVQPGGSLKLSCAASGFTFNT---- YAM*N*WVRW*A*SGKGLEWVGRIRSKS- NNYATAYAASVKGRFTISRDDSKNTAYLQMDSLKTEDTAVYYCVGGG---- ---------------------DFWGQGTLVTVSS (SEQ ID NO: 112) |
| Tau01 HG | LVQLVESGGGLVQPGGSLKLSCAASGFTFNT---- YAMHWVRQASGKGLEWVARIRSKS NNYATAYAASVKGRFTISRDDSKNTAYLQMDSLKTEDTAVYYCVGGG---- ---------------------DFWGQGTLVTVSS (SEQ ID NO: 113) |
| Tau01 HH | LVQLVESGGGLVQPGGSLKLSCAASGFTFNT---- YAMHWVRQASGKGLEWVGRIRSKS- NNYATYYAASVKGRFTISRDDSKNTAYLQMDSLKTEDTAVYYCVGGG---- ---------------------DFWGQGTLVTVSS (SEQ ID NO: 114) |
| Tau01 HI | LVQLVESGGGLVQPGGSLKLSCAASGFTFNT---- YAMHWVRQASGKGLEWVGRIRSKS- NNYATAYA*DS*VKGRFTISRDDSKNTAYLQMDSLKTEDTAVYYCVGGG---- ---------------------DFWGQGTLVTVSS (SEQ ID NO: 115) |
| Tau01 HJ | LVQLVESGGGLVQPGGSLKLSCAASGFTFNT---- YAMHWVRQASGKGLEWVGRIRSKS- NNYATAYAASVKGRFTISRDDSK*S*TAYLQMDSLKTEDTAVYYCVGGG---- ---------------------*S*FWGQGTLVTVSS (SEQ ID NO: 116) |
| Tau01 HK | LVQLVESGGGLVQPGGSLKLSCAASGFTFNT---- YAMHWVRQASGKGLEWVGRIRSKS- NNYATAYAASVKGRFTISRDDSKN*M*AYLQMDSLKTEDTAVYYCVGGG---- ---------------------DFWGQGTLVTVSS (SEQ ID NO: 117) |
| Tau01 HL | LVQLVESGGGLVQPGGSLKLSCAASGFTFNT---- YAMHWVRQASGKGLEWVGRIRSKS- NNYATAYAASVKGRFTISRDDSKNT*V*YLQMDSLKTEDTAVYYCVGGG---- ---------------------DFWGQGTLVTVSS (SEQ ID NO: 118) |
| Tau01 HM | LVQLVESGGGLVQPGGSLKLSCAASGFTFNT---- YAM*N*WVRQASGKGLEWVARIRSKS- NNYATYYAASVKGRFTISRDDSK*SM*AYLQMDSLKTEDTAVYYCVGGG---- ---------------------DFWGQGTLVTVSS (SEQ ID NO: 119) |
| Tau01 HN | LVQ*V*VESGGGLVQPGGSLKLSCAASGFTFNT---- *A*YMNWVRQASGKGLEWVGRIRSKS- NNYATYYAASVKGRFTISRDDSK*SM*AYLQMDSLKTEDTAVYYCVGGG---- ---------------------DFWGQGTLVTVSS (SEQ ID NO: 120) |

TABLE 8-continued

Tau01 Heavy Chain Humanization Strategy

| Name | Sequence<br>1234567890123456789012345678901234 5ABCD67890123456789012ABCD3<br>4567890123456789012345 6789012ABC345678901234567890<br>ABCDEFGHIJKLMNOPQRSTUV1234567890123 |
|---|---|
| Tau01 H0 | LVQ*VV*ESGGGLVQPGGSLKL*S*CAASGFTFNT----YAMNWVRQASGKGLEWVARIRSKS-NNYATYYAASVKGRFTISRDDSK*SM*AYLQMDSLKTEDTAVYYCVGGG-------------------------DFWGQGTLVTVSS (SEQ ID NO: 121) |

Residues in Italics indicate back-mutations to the Mouse Residue

Likewise, the sequence L33034 was chosen as the human kappa light chain donor candidate. This sequence scores high in sequence identity and similarity to Tau01 VK and has only 1 somatic mutation from the IGKV1-17*01 germline. It has five potential 4 Å proximity residues and one VCI residue change.

The sequences for Kappa Light Chain Humanization Strategy are shown in Table 12.

TABLE 12

Tau01 Kappa Light Chain Humanization Strategy

| Name | Sequence<br>1234567890123456789012345 67ABCDEF89012345678901234567890123456789012345 6<br>7890123456789012345678901 2345ABCDEF678901234567 |
|---|---|
| MoTau01 VK | DIQMTQSPSSLSASLGERVSLTCRASQEIS------VYLSWFQQKPDGTIKRLIYGAFTLDSGVPKRFSGSRSGSDYSLTISSLESEDFADYYCLQYVR-----YPWTFGGGTKLEIK (SEQ ID NO: 122) |
| L33034 | DIQMTQSPSSLSASVGDRVTITCRASQEIS------VYLGWYQQKPGKAPKRLIYGAFKLQSGVPSRFSGSRSGTEFTLTISSLQPEDFATYYCLQYVR-----YPWTFGGGTKVEIK (SEQ ID NO: 123) |
| Tau01 KA | DIQMTQSPSSLSASVGDRVTITCRASQEIS------VYLGWYQQKPGKAPKRLIYGAFKLQSGVPSRFSGSRSGTEFTLTISSLQPEDFATYYCLQYVR-----YPWTFGGGTKVEIK (SEQ ID NO: 124) |
| Tau01 KB | DIQMTQSPSSLSASVGDRVTITCRASQEIS------VYL*SW*FQQKPGKA*I*KRLIYGAF*T*LQSGVPSRFSGSRSG*SE*YTLTISSLQPEDFATYYCLQYVR-----YPWTFGGGTKVEIK (SEQ ID NO: 125) |
| Tau01 KC | DIQMTQSPSSLSASVGDRVTITCRASQEIS------VYL*SW*FQQKPGKAPKRLIYGAFKLQSGVPSRFSGSRSGTE*Y*TLTISSLQPEDFATYYCLQYVR-----YPWTFGGGTKVEIK (SEQ ID NO: 126) |
| Tau01 KD | DIQMTQSPSSLSASVGDRVTITCRASQEIS------VYL*SW*YQQKPGKAPKRLIYGAFKLQSGVPSRFSGSRSGTEFTLTISSLQPEDFATYYCLQYVR-----YPWTFGGGTKVEIK (SEQ ID NO: 127) |
| Tau01 KE | DIQMTQSPSSLSASVGDRVTITCRASQEIS------VYLGW*F*QQKPGKAPKRLIYGAFKLQSGVPSRFSGSRSGTEFTLTISSLQPEDFATYYCLQYVR-----YPWTFGGGTKVEIK (SEQ ID NO: 128) |
| Tau01 KF | DIQMTQSPSSLSASVGDRVTITCRASQEIS------VYLGWYQQKPGKA*I*KRLIYGAFKLQSGVPSRFSGSRSGTEFTLTISSLQPEDFATYYCLQYVR-----YPWTFGGGTKVEIK (SEQ ID NO: 129) |
| Tau01 KG | DIQMTQSPSSLSASVGDRVTITCRASQEIS------VYLGWYQQKPGKAPKRLIYGAF*T*LQSGVPSRFSGSRSGTEFTLTISSLQPEDFATYYCLQYVR-----YPWTFGGGTKVEIK (SEQ ID NO: 130) |
| Tau01 KH | DIQMTQSPSSLSASVGDRVTITCRASQEIS------VYLGWYQQKPGKAPKRLIYGAFKLQSGVPSRFSGSRSG*SE*FTLTISSLQPEDFATYYCLQYVR-----YPWTFGGGTKVEIK (SEQ ID NO: 131) |
| Tau01 KI | DIQMTQSPSSLSASVGDRVTITCRASQEIS------VYLGWYQQKPGKAPKRLIYGAFKLQSGVPSRFSGSRSGTE*Y*TLTISSLQPEDFATYYCLQYVR-----YPWTFGGGTKVEIK (SEQ ID NO: 132) |

TABLE 12-continued

Tau01 Kappa Light Chain Humanization Strategy

```
                       Sequence
                 1         2         3         4         5         6
         7         8         9         10
         1234567890123456789012345 67ABCDEF8901234567890123456789012345 67890123456
Name     7890123456789012345678901 2345ABCDEF678901234567
```

Tau01 KJ    DIQMTQSPSSLSASVGDRVTITCRASQEIS------
            VYLGWYQQKPGKAPKRLIYGAF*S*LQSGVPSRFSGSRSGTEFTLTISSLQPEDFATYYCLQYVR-----
            YPWTFGGGTKVEIK (SEQ ID NO: 133)

Tau01 KL    DIQMTQSPSSLSASVGDRVTITCRASQEIS------
            VYL*SWF*QQKPGKA*I*KRLIYGAFKLQSGVPSRFSGSRSGTEYTLTISSLQPEDFATYYCLQYVR-----
            YPWTFGGGTKVEIK (SEQ ID NO: 134)

Tau01 KM    DIQMTQSPSSLSASVGDRVTITCRASQEIS------
            VYL*SWF*QQKPGKA*I*KRLIYGAF*S*LQSGVPSRFSGSRSGTEYTLTISSLQPEDFATYYCLQYVR-----
            YPWTFGGGTKVEIK (SEQ ID NO: 135)

Tau01 KN    DIQMTQSPSSLSASVGDRVTITCRASQEIS------
            VYLGWYQQKPGKAPKRLIYGAF*T*LQSGVPSRFSGSRSGTEYTLTISSLQPEDFATYYCLQYVR-----
            YPWTFGGGTKVEIK (SEQ ID NO: 136)

Tau01 KO    DIQMTQSPSSLSASVGDRVTITCRASQEIS------
            VYLGWYQQKPGKAPKRLIYGAF*S*LQSGVPSRFSGSRSGTEYTLTISSLQPEDFATYYCLQYVR-----
            YPWTFGGGTKVEIK (SEQ ID NO: 137)

Tau01 KP    DIQMTQSPSSLSASVGDRVTITCRASQEIS------
            VYLGW*F*QQKPGKAPKRLIYGAFKLQSGVPSRFSGSRSGTEYTLTISSLQPEDFATYYCLQYVR-----
            YPWTFGGGTKVEIK (SEQ ID NO: 138)

Residues in Italics indicate back-mutations to the Mouse Residue.

Design of Tau01 Humanized Heavy Chain Variants

Once a suitable human framework has been identified, the synthetic protein and DNA sequence can be designed. The initial design of the humanized version of Tau01 is the grafting of CDR 1, 2 and 3 from MoTau01 VH into the acceptor FW of DQ840895.1, thereby creating variant Tau01 HA. The eight 4 Å proximity residues and one VCI residue, at positions 1, 4, 35, 49, 58, 61, and 76-78 are then back mutated to the mouse equivalent residue, in the humanized version Tau01 HB, and mutated one at a time in the following variants: sequences were assembled in silico and designated Tau01 HD to Tau01 HL. Table 8 compares the murine and the humanized versions of Tau01 VH protein sequences.

Design of Tau01 Humanized Light Chain Variants

The framework from L33034 was used to design the DNA and protein for the humanized constructs. CDR 1, 2 and 3 from Tau01 VK are shown grafted into the acceptor FW of L33034 to generate the initial version of humanized Tau01. There are five unmatched 4 Å Proximity residues and one VCI residue, at positions 34, 36, 44, 53, 69 and 71, in Tau01 KA that were back-mutated to the equivalent mouse residue in the variant Tau01 KB (Table 12).

These residues were mutated one at a time in the following variants: sequences were assembled in silico and designated Tau01 KD to Tau01 KI. In version Tau01 KG, the residue K, back-mutated to the mouse residue T, was also mutated to the Human germline residue S. This additional variant was named Tau01 KJ.

Design of the Heavy and Light Chain C Versions

Following on from the design of the initial humanized variants, a homology model of Tau01 HAKA was built and evaluated. The latter model was superimposed with the model of the mouse antibody. Each position identified for back-mutation and the 3 Å residues surrounding those positions were highlighted and examined in the models. Based on this data, predictions were made as to which residues were the most important to back-mutate and these were incorporated to form the HC version for the heavy chain (Table 8) and the KC version for the light chain (Table 12).

Example 4 (Generation and Properties of a Humanized Antibodies)

Generation of Tau01 Humanized Antibodies

The sequences for Tau01 HA/B/C and KA/B/C were codon optimized to use codons preferentially utilized by human cells and synthesized by Genscript. KA/B/C and HA/B/C constructs were PCR amplified and cloned into pHuK and pHuG4, respectively in ligase independent cloning reactions and used to transform TOP10 bacteria. Version HA or KA was subsequently modified by PCR mutagenesis to obtain the other humanized variants annotated in the Table 8 or 12 respectively, using the primers in Table 4.

Clones were sequenced and plasmid DNA was prepared using the QIAGEN Plasmid Miniprep Kit or Qiagen Plasmid Maxiprep kit. The expression construct sequences (HA, HB, HC, KA, KB and KC) are shown in FIGS. 9 to 14.

Antibody Expression

Expression plasmid preparations encoding (humanized or chimeric) VH and VK were used to transfect ExpiCHO cells, cultured for 7 days in serum free media, whereupon the conditioned medium containing secreted antibody was harvested. The concentrations of IgG4κ antibodies in ExpiCHO cell conditioned media were measured by octet and are shown in Tables 14 A-C. Most antibodies were produced at good expression levels.

TABLE 14

IgG levels in transfected ExpiCHO cell conditioned medium

| | IgG Concentration (μg/ml) |
|---|---|
| A | |
| MoTau01 HuG4K | 181.4 |
| Tau01 HAKA | 357.1 |
| Tau01 HAKB | 353.7 |
| Tau01 HAKC | 68* |
| Tau01 HBKA | 397.9 |
| Tau01 HBKB | 562.2 |
| Tau01 HBKC | 67* |
| Tau01 HCKA | 695.4 |
| Tau01 HCKB | 490.4 |
| Tau01 HCKC | 624.4 |
| B | |
| Tau01 HDKA | 75.5 |
| Tau01 HDKB | 67.4 |
| Tau01 HDKC | 49 |
| Tau01 HEKA | 8.24* |
| Tau01 HEKB | 65.3 |
| Tau01 HEKC | 51.9 |
| Tau01 HFKA | 54.75 |
| Tau01 HFKB | 115.15 |
| Tau01 HFKC | 118.15 |
| Tau01 HGKA | 66.4 |
| Tau01 HGKB | 56.3 |
| Tau01 HGKC | 7.14* |
| Tau01 HHKA | 57.1 |
| Tau01 HHKB | 53.6 |
| Tau01 HHKC | 61.5 |
| Tau01 HIKA | 65.8 |
| Tau01 HIKB | 47.4 |
| Tau01 HIKC | 58.5 |
| Tau01 HJKA | 52.4 |
| Tau01 HJKB | 49.8 |
| Tau01 HJKC | 52.1 |
| Tau01 HKKA | 48 |
| Tau01 HKKB | 39.5 |
| Tau01 HKKC | 48.8 |
| Tau01 HLKA | 42.3 |
| Tau01 HLKB | 42.2 |
| Tau01 HLKC | 53.7 |
| C | |
| Tau01 HBKD | 20.9* |
| Tau01 HBKE | 61.9 |
| Tau01 HBKF | 74 |
| Tau01 HBKG | 84.1 |
| Tau01 HBKH | 60.4 |
| Tau01 HBKI | 49.6 |
| Tau01 HBKJ | 83.3 |
| Tau01 HCKD | 16.3* |
| Tau01 HCKE | 60.1 |
| Tau01 HCKF | 50 |
| Tau01 HCKG | 61 |
| Tau01 HCKH | 55.8 |
| Tau01 HCKI | 19.2* |
| Tau01 HCKJ | 48.6 |

*Expression of transfection control, Hu1210 HuG1K was also reduced (expected level ~100 μg/ml).

Antigen Binding by Initial Versions of the Humanized Antibodies

The binding of the humanized variants to the TauC3 antigen provided was tested by binding ELISA as described in Example 5. The data shown in FIG. 15 displays the binding ELISA of TauC3 with humanized antibodies consisting of the HA/HB heavy chains in combination with KA/KB light chains. The HAKA and HAKB humanized antibodies do not bind to TauC3. The MoTau01HuG4K chimeric binds to TauC3 with an EC50 value of 0.65 nM and the HBKA and HBKB variants bind with similar EC50 values with the HBKB version being the closest (0.78 nM).

Figures 16A, 16B:
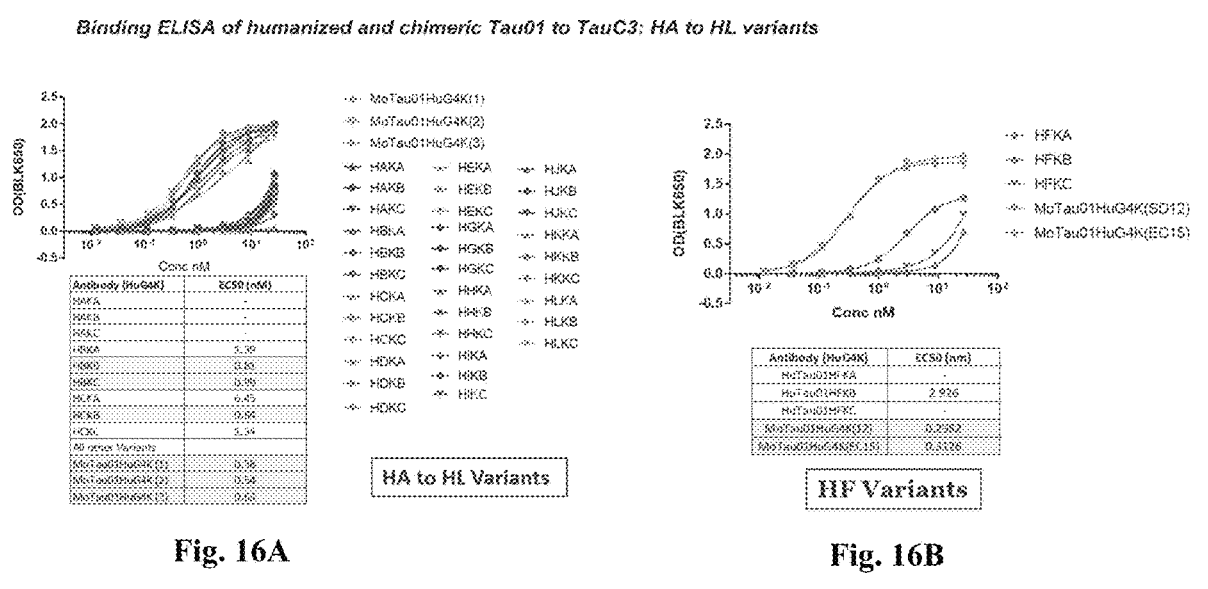

Considering this data, further versions of the humanized heavy and light chains were expressed, each with a single back-mutation (Tables 8 and 12). FIG. 16 shows the results of the heavy chain single mutants and the HC version in combination with KA-KC, tested for binding to TauC3 by ELISA. The data shows the heavy chain single mutants were unable to bind as well as the chimeric antibody to TauC3. The HB and HC versions in combination with KA-KC bound to TauC3 with the highest EC50 values with HBKB and HBKC displaying the closest value to the chimeric antibody (0.81 nM and 0.84 nM respectively). These results were confirmed using a screening assay on the Octet instrument with one concentration of TauC3 as described in section 8.12 (FIG. 17). The Octet data is not optimal as two-phase association and dissociation events can be observed which is likely due to the nature of the TauC3 protein. However, the octet data is sufficient for screening and ranking the humanized candidates.

Figure 19A:
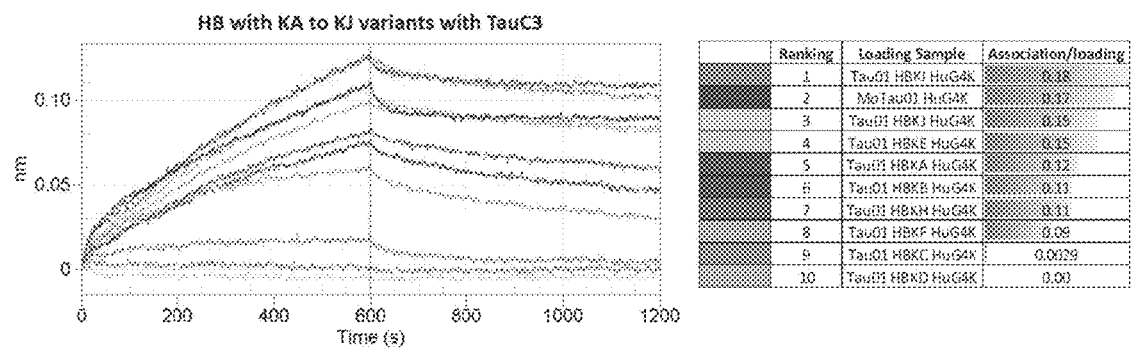
FIGS. 19A and 19B. Octet screening of the humanized Tau01 antibodies to TauC3: HB with KA to KJ variants.
Figure 19B:
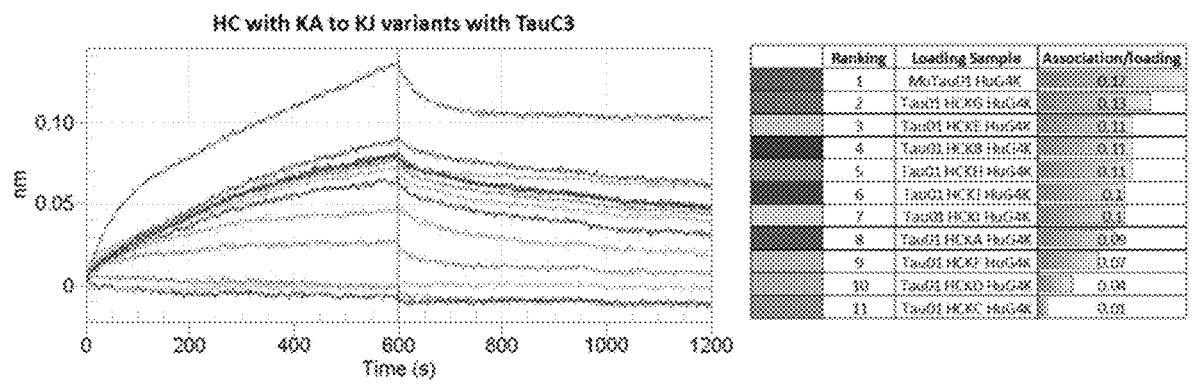

Since HB/HC are the best heavy chains versions, their binding to TauC3 in combination with all the light chain versions (KA-KJ) was tested by binding ELISA (FIG. 18) and the Octet screening assay (FIGS. 19 A and B). Many of the light chain single mutants are capable of retaining binding to TauC3 but the light chain versions KE, KG, KI and KJ rank the highest in both assays.

Design and Generation of the Second Round of the Humanized Antibodies

Based on the sub-optimal binding results for the initial humanized variants, a second round of variants were designed by incorporating additional back-mutations into the HC and KC versions (HM-HO and KL and KM respectively) or combining two back-mutations in the KA version (KN-KP) (Tables 8 and 12). The mutagenesis, DNA preparation, expression and quantitation were conducted. The expression levels obtained are shown in Tables 14 D and E. Most antibodies were produced at good expression levels.

TABLE 14

IgG levels in transfected ExpiCHO cell conditioned medium

|  | IgG Concentration (µg/ml) |
| --- | --- |
| D | |
| Tau01 HMKA | 377.95 |
| Tau01 HMKB | 329.85 |
| Tau01 HMKC | 552.3 |
| Tau01 HMKG | 399.5 |
| Tau01 HMKJ | 417.9 |
| Tau01 HMKI | 419.2 |
| Tau01 HNKA | 441.4 |
| Tau01 HNKB | 557.8 |
| Tau01 HNKC | 50.45 |
| Tau01 HNKG | 487 |
| Tau01 HNKJ | 662.8 |
| Tau01 HNKI | 370.5 |
| Tau01 HOKA | 354.85 |
| Tau01 HOKB | 352.75 |
| Tau01 HOKC | 92.85 |
| Tau01 HOKG | 321.8 |
| Tau01 HOKJ | 333.6 |
| Tau01 HOKI | 262.15 |
| E | |
| Tau01 HCKL | 353.7 |
| Tau01 HCKM | 261.75 |
| Tau01 HCKN | 406.7 |

TABLE 14-continued

IgG levels in transfected ExpiCHO cell conditioned medium

|  | IgG Concentration (µg/ml) |
| --- | --- |
| Tau01 HCKO | 710.4 |
| Tau01 HCKP | 677.5 |
| Tau01 HMKE | 535.6 |
| Tau01 HMKL | 449.8 |
| Tau01 HMKM | 164.43 |
| Tau01 HMKN | 443.7 |
| Tau01 HMKO | 431.7 |
| Tau01 HMKP | 352.1 |

Antigen Binding by the Second Round of the Humanized Tau01 Antibodies

Figure 20A:
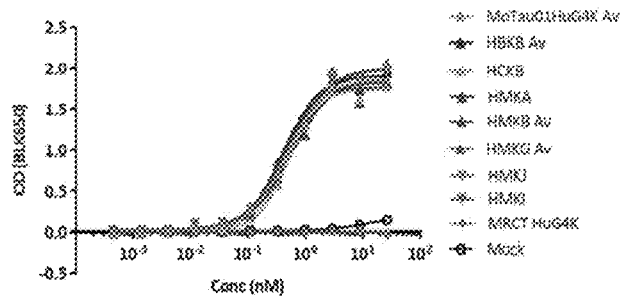
FIGS. 20A to 20C. Binding ELISA of the second round of humanized Tau01 antibodies to TauC3: HM, HN and HO variants.
Figure 20B:
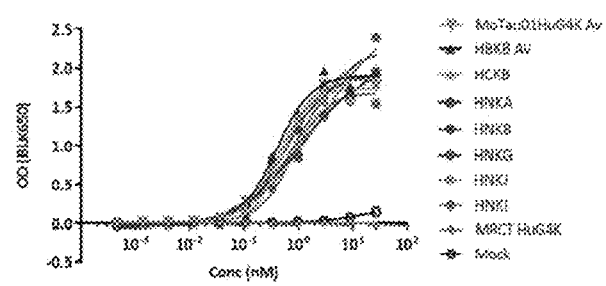
Figure 20C:
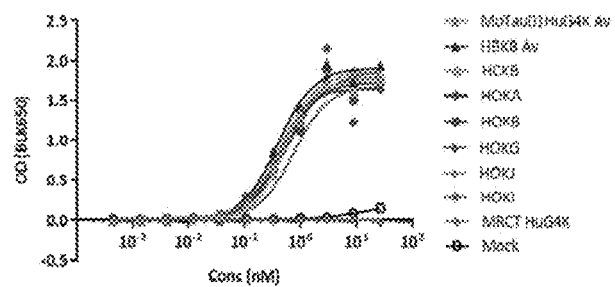

In order to evaluate the heavy chain, the binding activity of antibody variants containing HM, HN and HO combined with light chains KA, KB, KG, KI, KJ were tested by ELISA (FIG. 20) and Octet (FIG. 21) against TauC3. The HM and HO variants ranked the highest in both assays. The only difference between the HO and HM variant is an additional back-mutation of L-V in position 4 which is also present in the HN variant. Since the HN versions did not bind as well as HM versions, the L-V back-mutation was not deemed to be necessary so HM was chosen as the top heavy chain from the second round of designs.

Figure 24A:
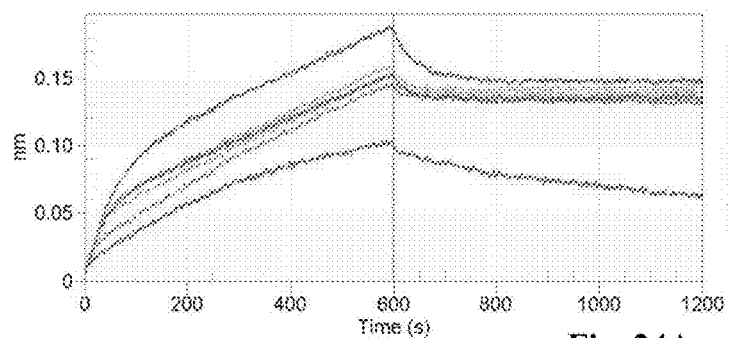
FIGS. 24A and 24B. Octet screening of the second round of humanized Tau01 antibodies to TauC3 and FL Tau: Lead variants.
Figure 24B:
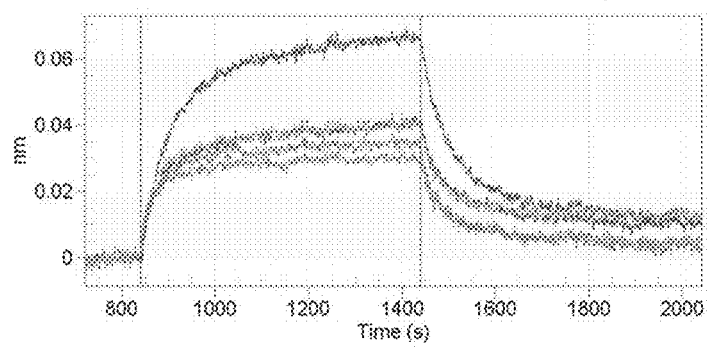

The lead heavy chain HM was expressed with several light chains; KA-KC, the selected single-mutants previously highlighted (KE, KG, KI, KJ) and the second round of designs, KL, KN, KO, KP. These lights chains were also expressed in combination with the earlier favored heavy chain, HC, for comparison. The binding of these humanized antibody variants was tested by binding ELISA (FIG. 22) against TauC3. Overall, the HM variants bound with higher EC50s than the HC variants so the former variants were evaluated in the Octet screening assay (FIG. 23). The antibody variants HMKE, HMKN, HMKO and HMKP ranked the highest in both assays. The KM light chain was also screened in combination with HC/HM and compared to the leading antibody variants by Octet (FIG. 24 A). The HMKM version ranked very highly in the Octet screening assay whereas HCKM ranked the lowest. The binding of the humanized leads was also tested against FL Tau using Octet to determine how much selectivity had been retained (FIG. 24 B). The signals obtained with 500 nM FL Tau were very low (0.03-0.07 nm) which is in the non-specific binding range.

Figure 25A:
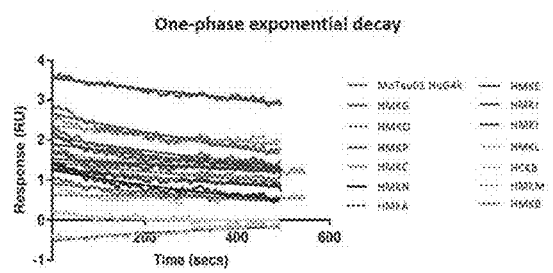
FIGS. 25A and 25B. Off-rate ranking of the lead humanized candidates with TauC3 using Biacore.
Figure 25B:
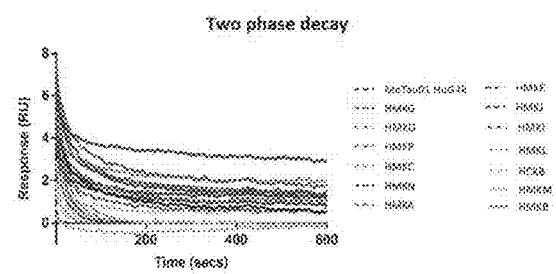
Figure 26A:
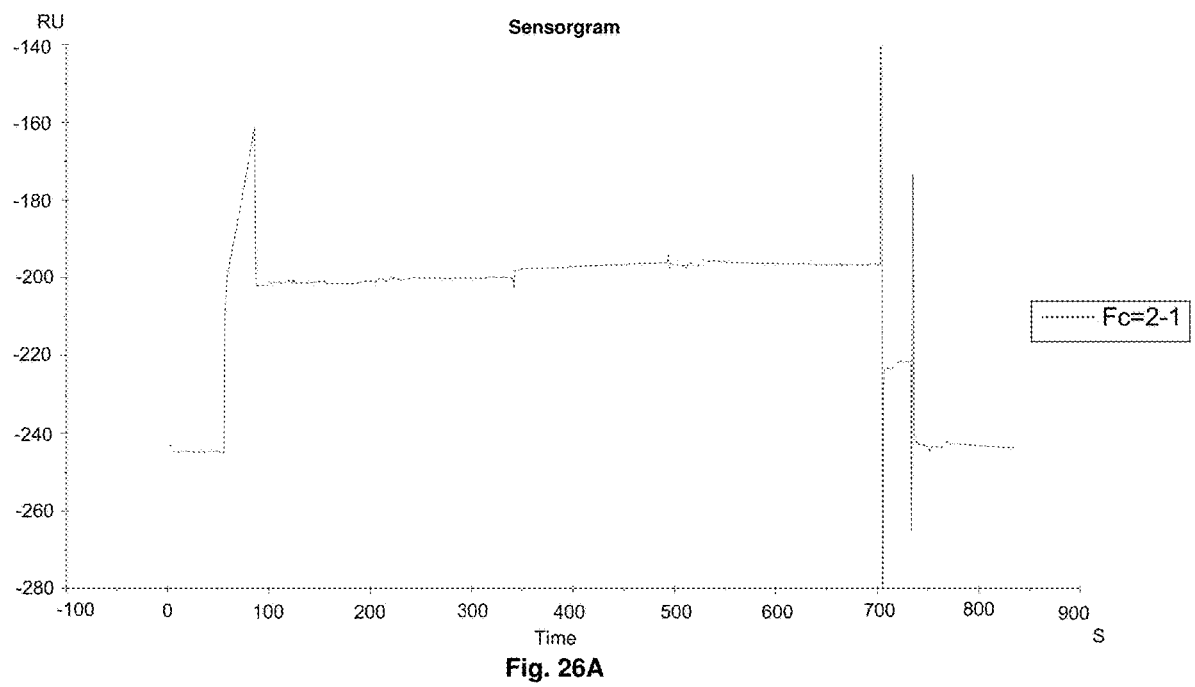
FIGS. 26A and 26B. Binding test to FL Tau by Biacore.
Figure 26B:
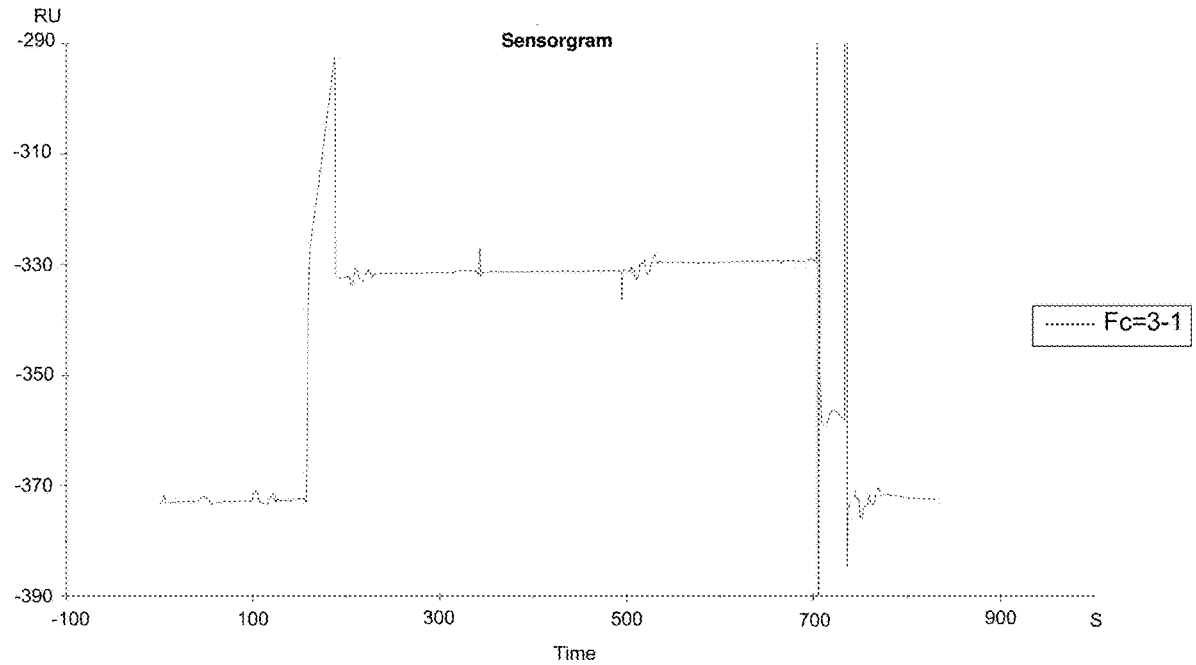

To further evaluate the binding data observed on the Octet, an off-rate ranking experiment was performed on the Biacore 200 instrument. Biacore offers greater selectivity than the Octet and facilitated the immobilization of TauC3 onto a CM5 chip via amine coupling which stabilizes the antigen. This produces higher quality data with stable baselines and good reproducible responses. Once TauC3 is immobilized, one concentration (5 nM) of antibody is added, followed by a dissociation and regeneration step (Section 8.20). The off-rates were fitted using a two-phase decay model (FIG. 25 B) or a one phase decay fitting only the second off-rate (FIG. 25 A). The candidates were then ranked based on the off-rates obtained using the fits and compared. The data agreed with the Octet results (albeit with a different ranking order), highlighting Tau01 HMKM, HMKO, HMKP, HMKN and HMKE as the humanized variants with the slowest off-rates. The lack of binding of FL Tau to chimeric and a humanized candidate was also confirmed by Biacore by loading the antibody onto a Protein G chip and adding 250 nM FL Tau. FIG. 26 shows no binding could be observed for either MoTau01 HuG4k or Tau01 HCKB.

Thermal Stability of the Humanized Tau01 Candidate Antibodies

The aim of this experiment was to test the thermal stability of the chimeric antibody and some of the humanized antibodies (Tau01 HCKG, HCKN, HMKE, HMKN, HMKO, HMKP) when subjected to higher temperatures, varying from 35° C. to 95° C. for 10 minutes, cooled to 4° C. and used in a binding ELISA at the EC80 concentration of each candidate (Section 8.15). All humanized candidate antibodies were more stable than the chimeric antibody, retaining binding ability to TauC3 until 67-68° C. following which binding to TauC3 decreased (FIG. 27). The humanized variants exhibit increased thermal stability compared to the chimeric antibody MoTau01 HuG4k which only retained binding up to ~55° C. The variants containing the HM heavy chain retained binding to slightly higher temperatures than the HC heavy chain variants tested.

Selection of Lead Humanized Tau01 Candidate Antibodies

Taking all of these results together, the lead humanized antibody variants Tau01 HMKE, HMKM, HMKN, HMKO and HMKP were selected to scale-up and purify using affinity and size-exclusion chromatography, as described in Section 8.16. The purified antibodies were further characterized in a series of biophysical assays. The HCKB humanized candidate with weaker binding to TauC3 was also scaled up for expression and purification in order to be used as a comparator antibody for ranking in the seeding assay. This would allow us to further test the correlation between antibody affinity in vitro and potency in the cell assay.

Aggregation of Humanized Tau01 Candidate Antibodies

Figure 28A:
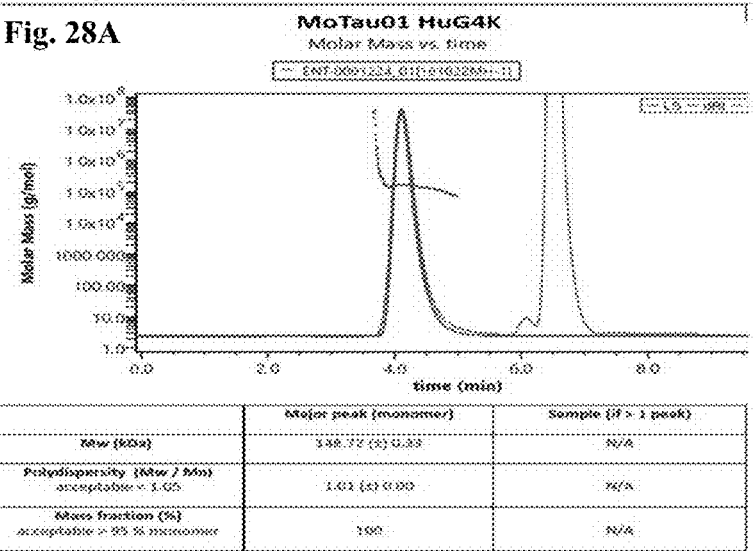
FIGS. 28A to 28C. SEC-MALS aggregation analysis of purified MoTau01 HuG4K and Tau01 HCKB HuG4K antibodies.
Figure 28B:
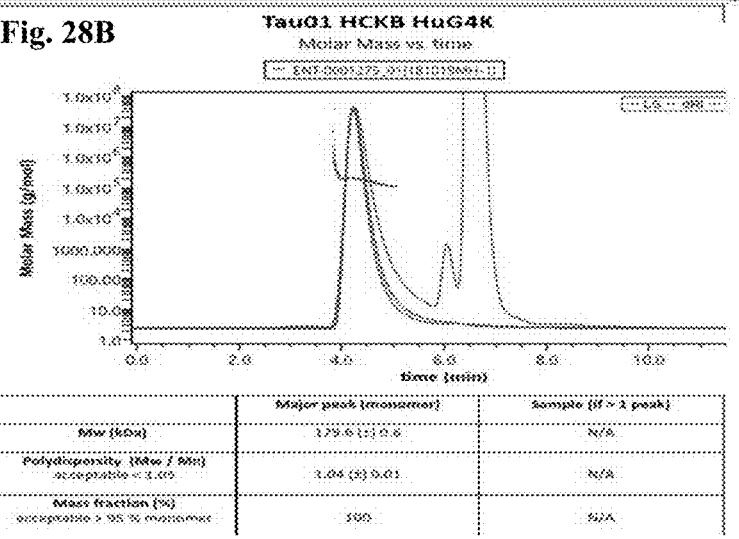
Figure 28C:
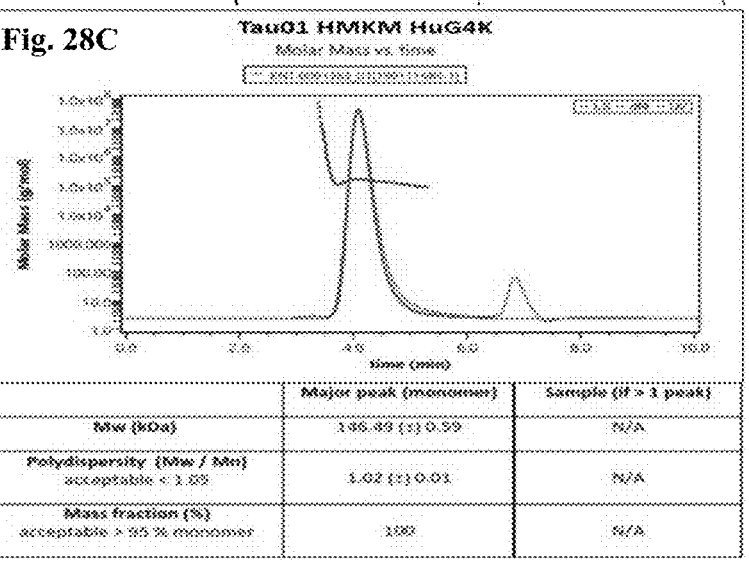
Figure 29A:
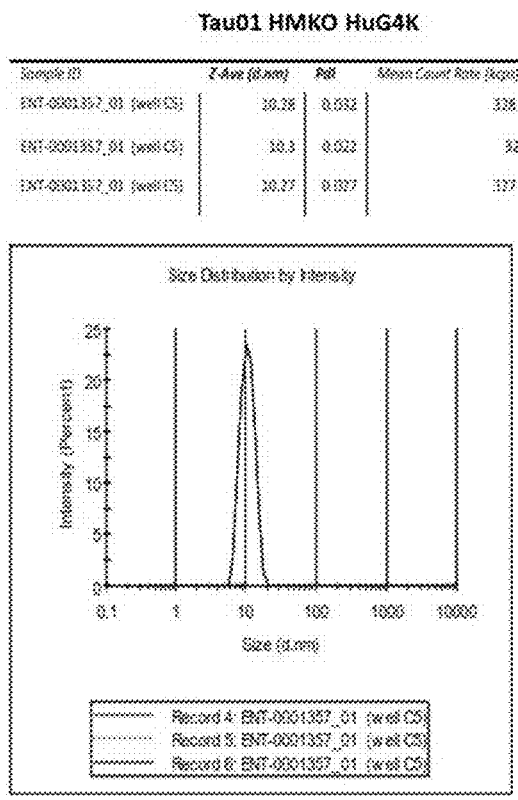
FIGS. 29A to 29D. DLS analysis of purified Tau01 HMKN, HMKO, HMKP, HMKE, and HMKM HuG4K antibodies.
Figure 29B:
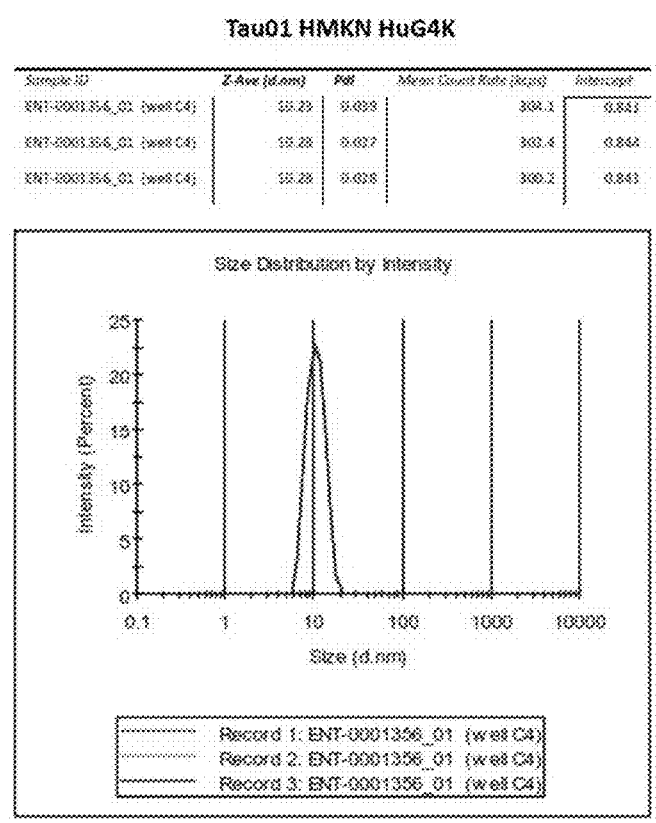
Figure 29C:
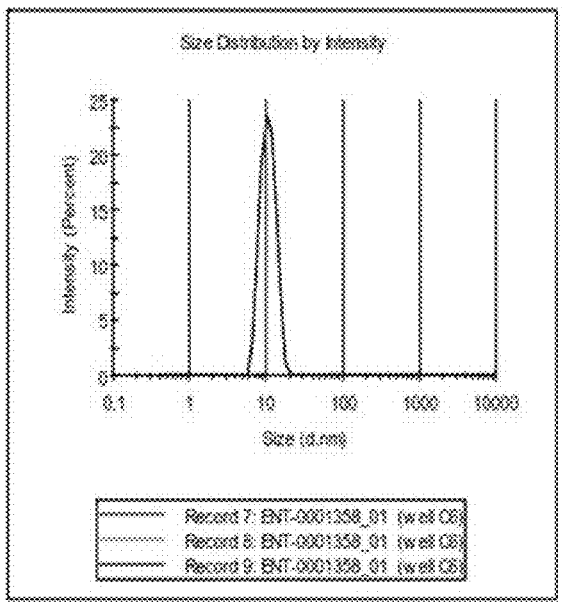
Figure 29D:
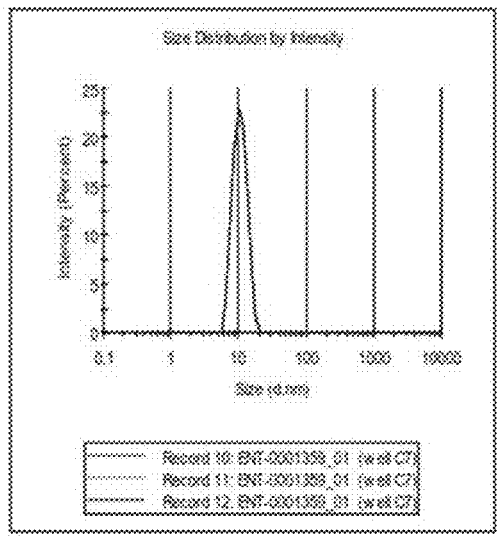

As part of the QC process after purification, the antibody samples are subjected to SEC-MALS/DLS followed by mass spectrometry. To determine the absolute molar masses and check for aggregation, the purified antibody samples were injected into a size exclusion column in an HPLC system and analyzed by multi-angle light scattering. The profiles for MoTau01 HuG4k and Tau01 HMKM show no signs of aggregation with an average molecular weight of about 147-8 kDa, which is the expected range for an IgG monomer in this analysis setup (FIG. 28 A). The Tau01 HCKB antibody profile has a broad peak which skews the data resulting in a molecular weight of 179.6 kDa (FIG. 28 B). All three antibodies are monodisperse (Mw/Mn<1.05) and display no signs of aggregation.

Dynamic light scattering is a complementary technique to static-light scattering (SEC-MALS) for the detection of soluble aggregates and was used to QC the humanized variants Tau01 HMKN, HMKO, HMKP and HMKE. The Z-Ave or hydrodynamic diameter is expected to be around 10 for an antibody and the Polydispersity index (PdI) should be <0.1 if the sample is monodisperse. As shown in FIG. 29, all of the antibody samples contain one major population which is monodisperse and are consistent with the size of a monoclonal antibody.

Figure 30C:
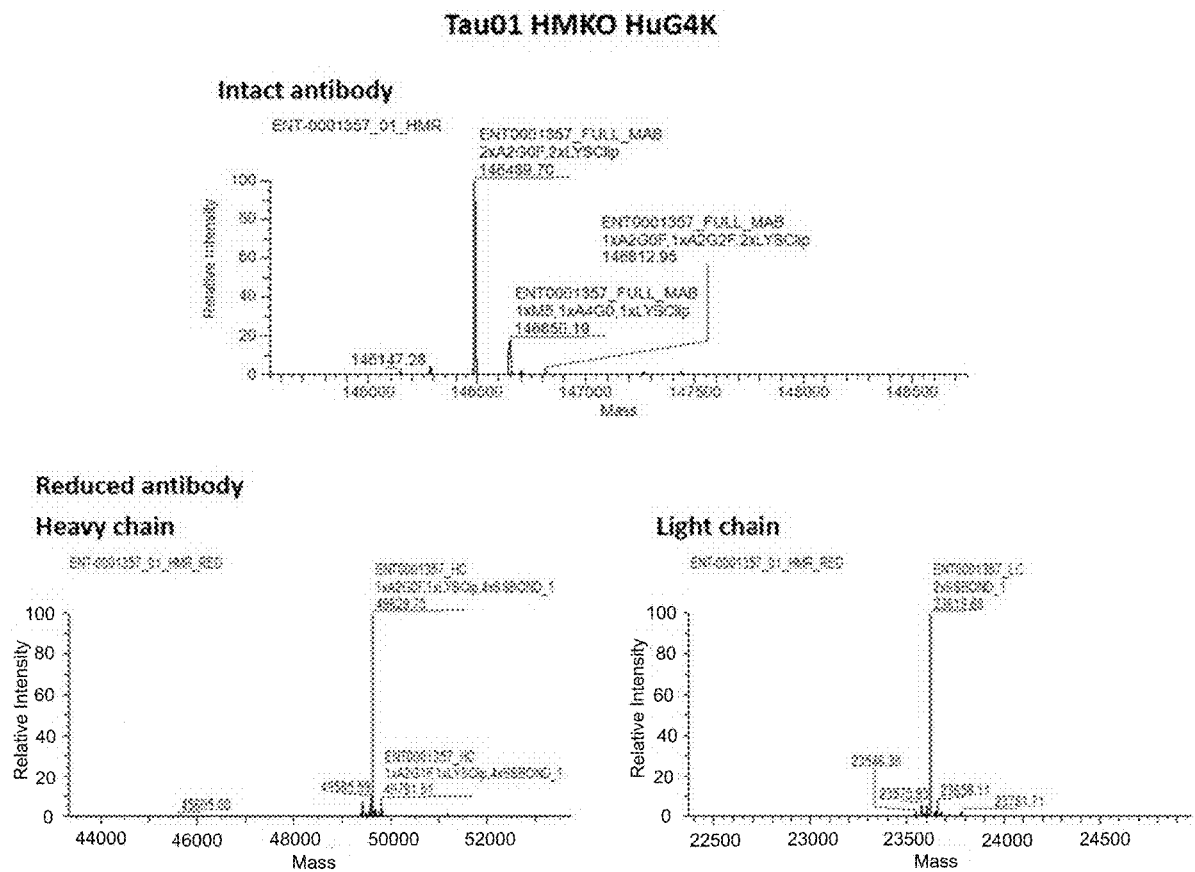
Figure 30D:
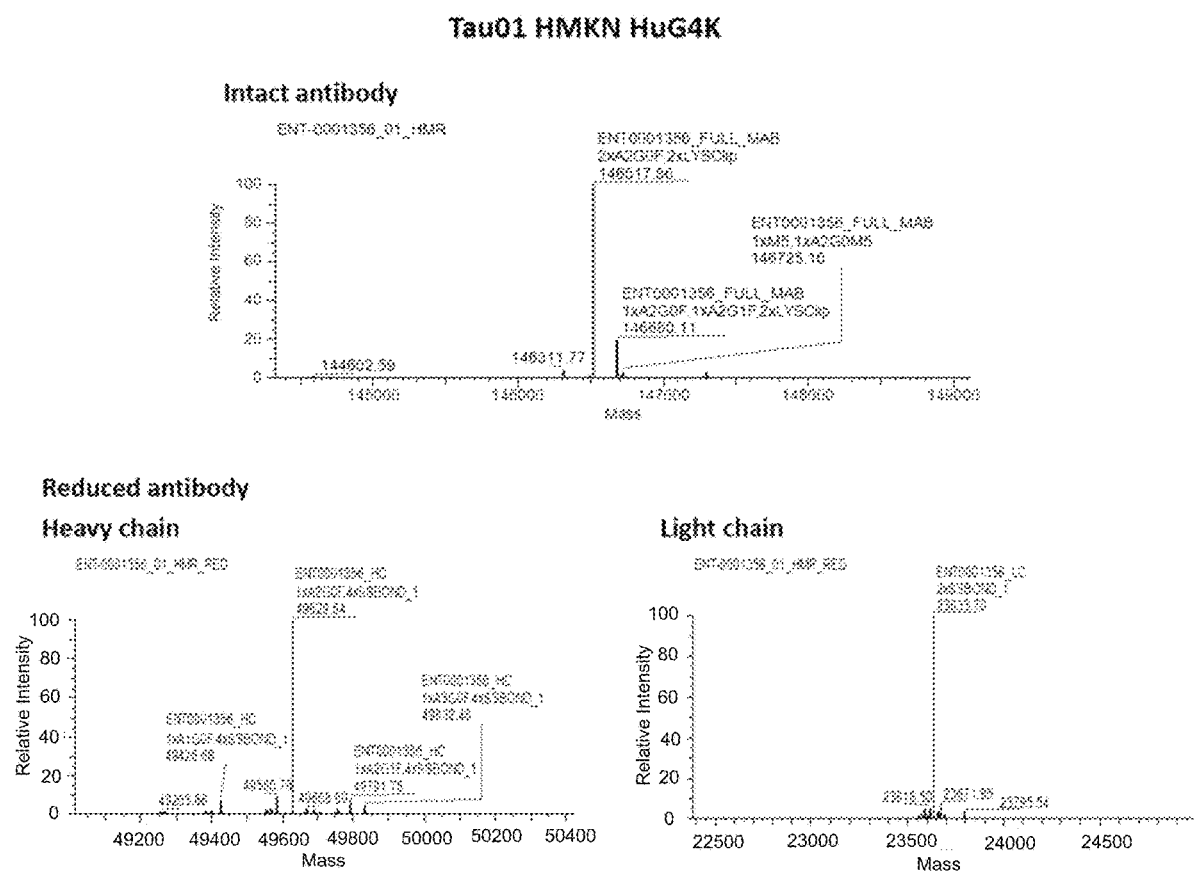
Figure 31A:
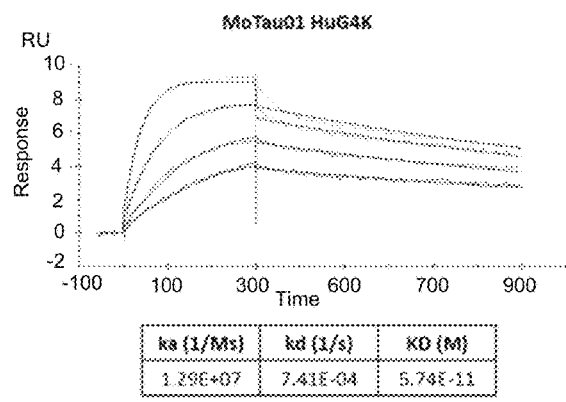
FIGS. 31A to 31G. Biacore kinetics of the humanized candidate antibodies.
Figure 31B:
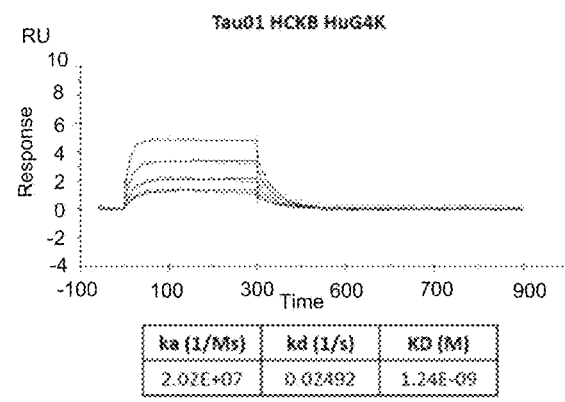
Figure 31C:
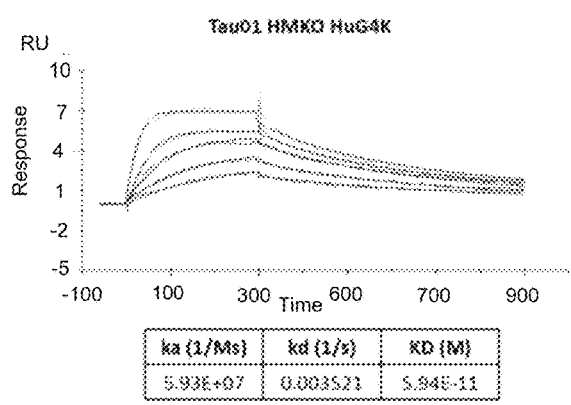
Figure 31D:
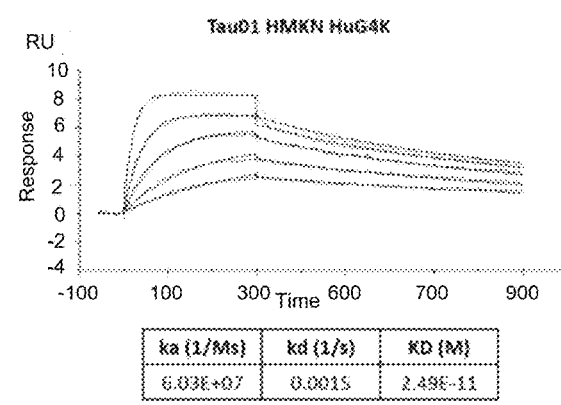
Figure 31E:
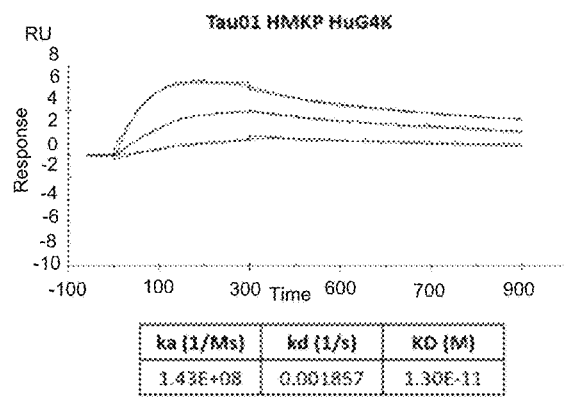
Figure 31F:
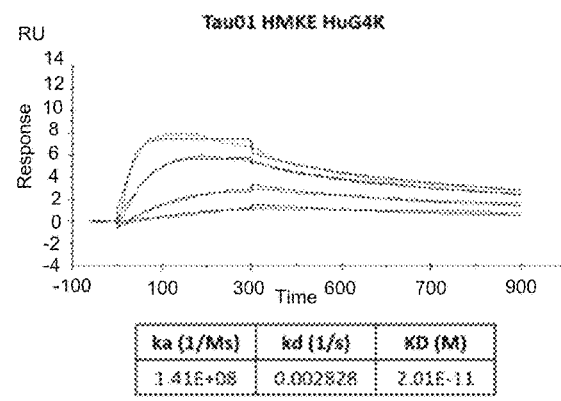
Figure 31G:
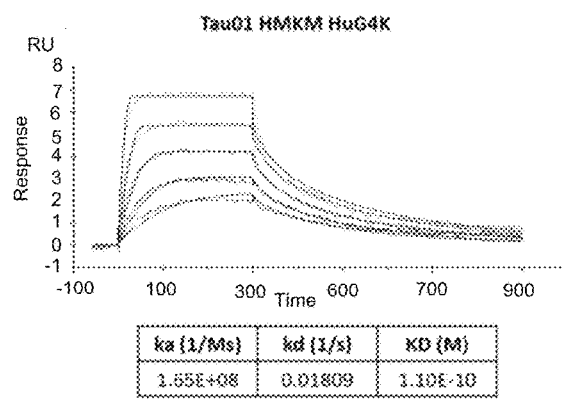
Figure 35A:
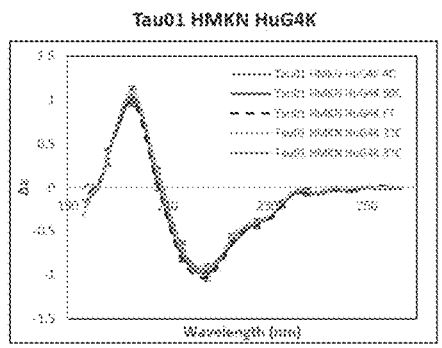
FIGS. 35A to 35D. Freeze/Thaw and heat stress analysis of the humanized candidate antibodies by Circular Dichroism.
Figure 35B:
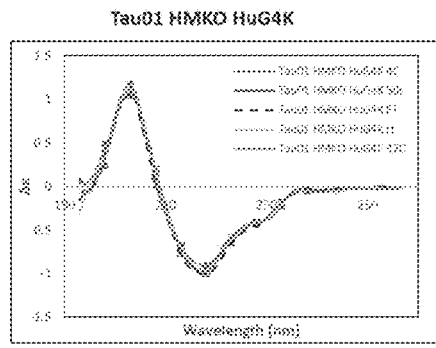
Figure 35C:
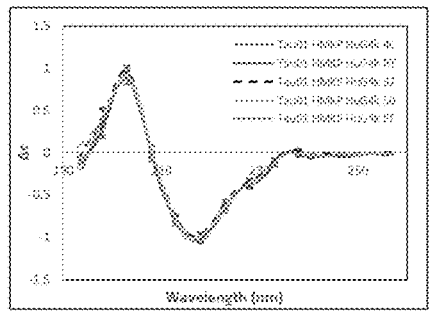
Figure 35D:
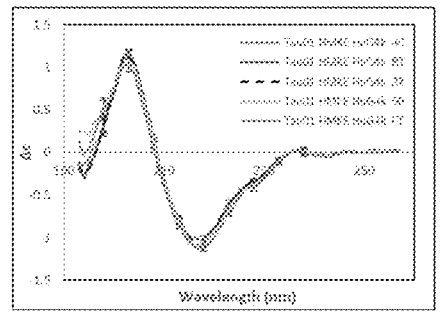
Figure 36A:
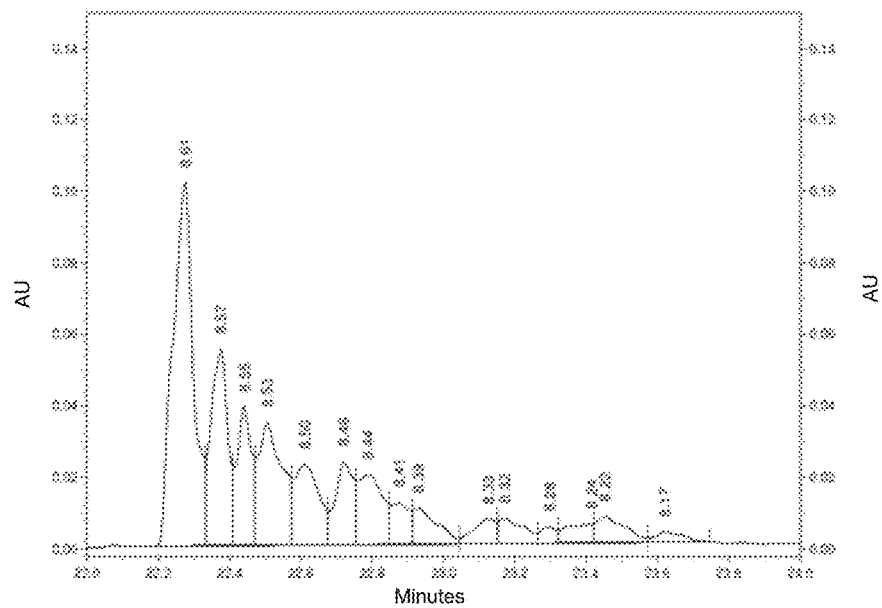
FIGS. 36A to 36D. Capillary Isoelectric focusing to determine the isoeletric points of the humanized candidates.
Figure 36B:
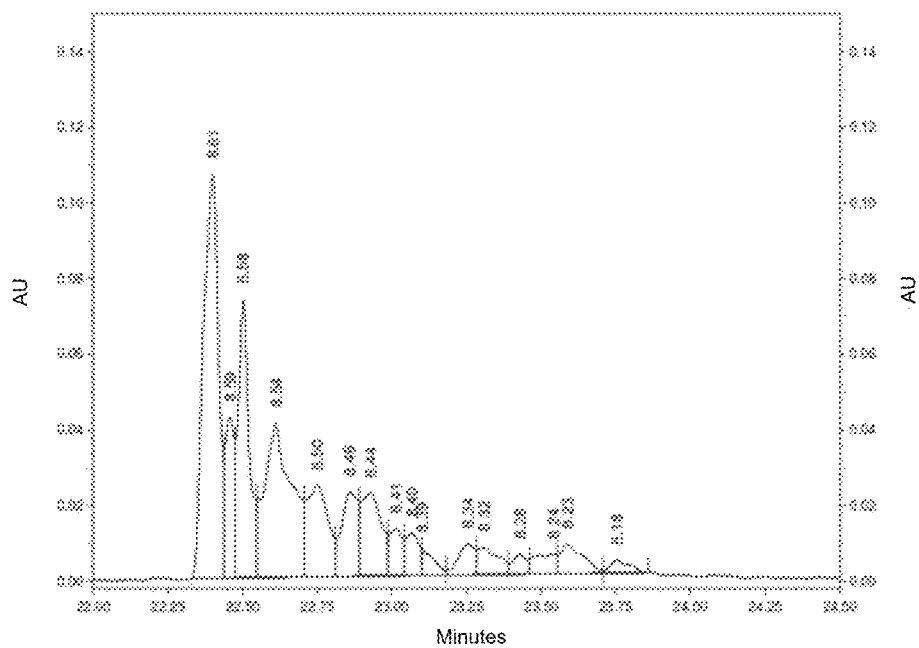
Figure 36C:
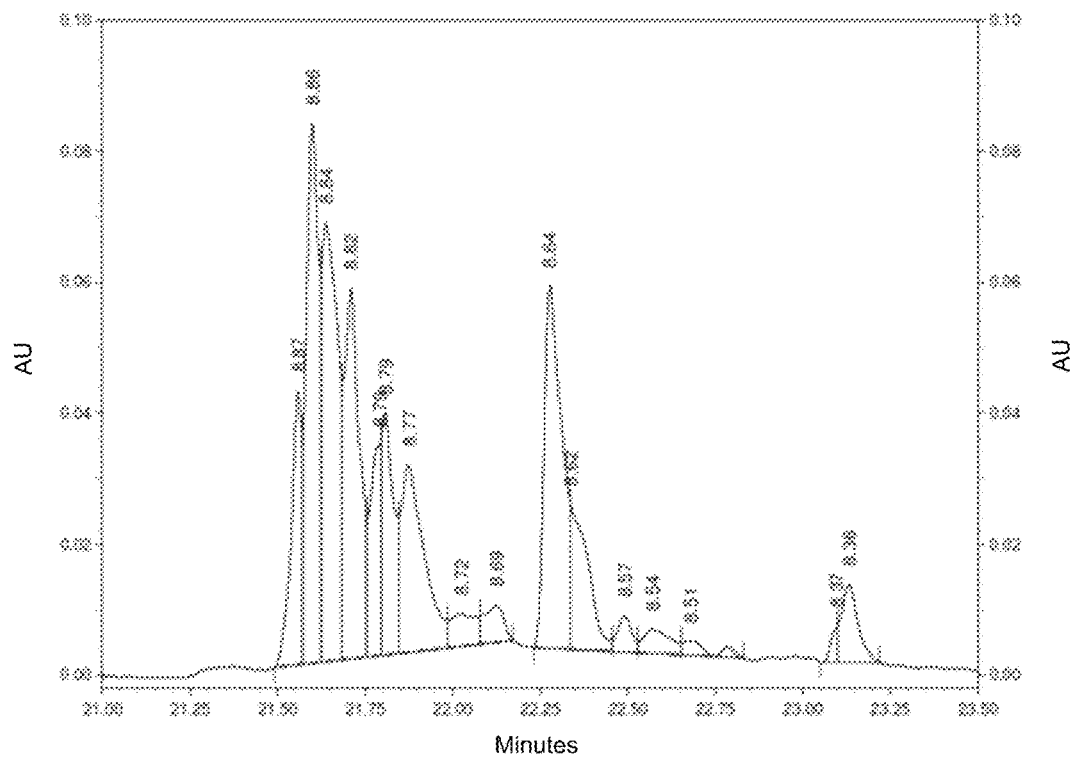
Figure 36D:
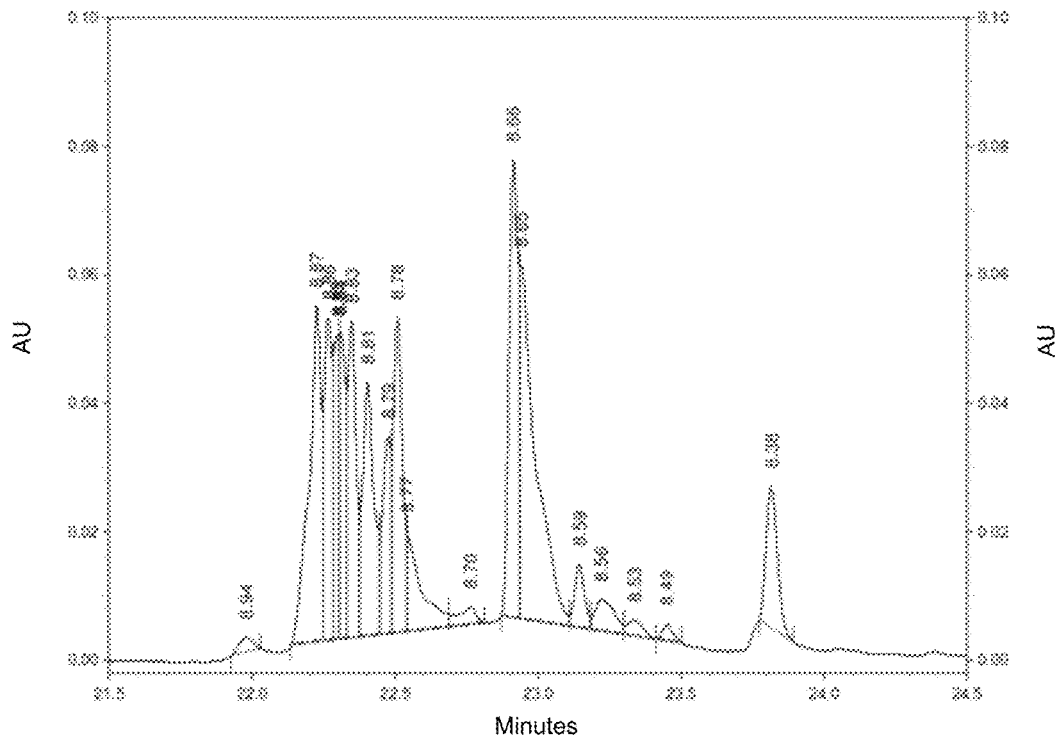
Figure 37A:
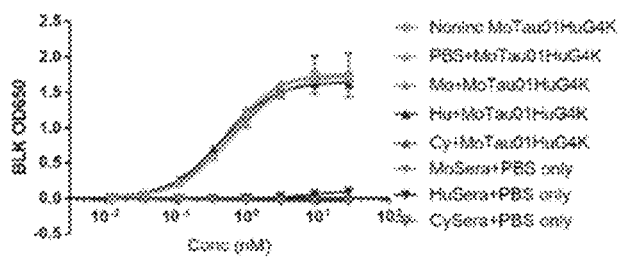
FIGS. 37A to 37F. Serum stability assessment of the humanized candidate antibodies.
Figure 37B:
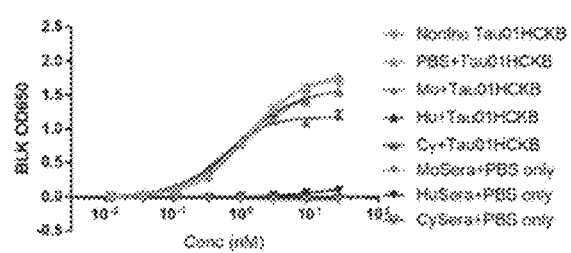
Figure 37C:
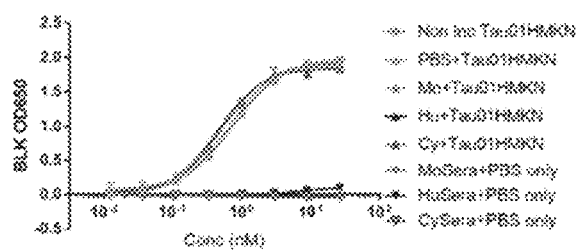
Figure 37D:
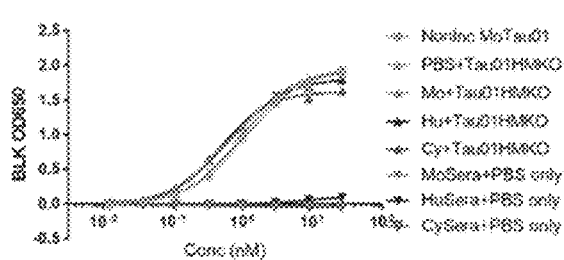
Figure 37E:
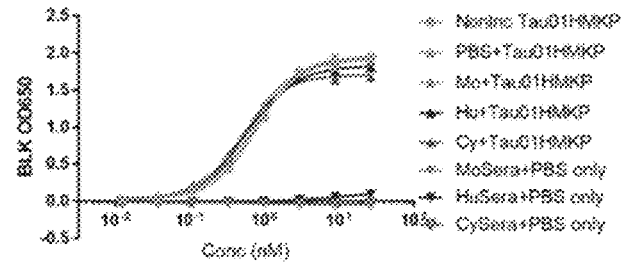
Figure 37F:
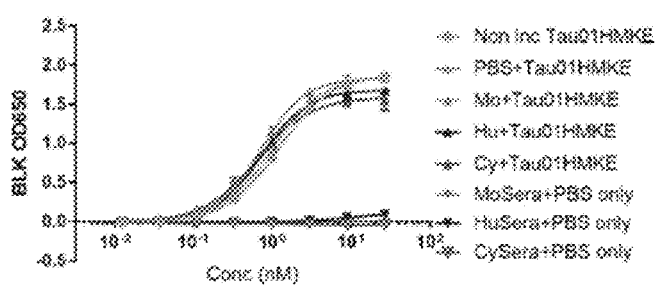

To confirm the accurate molecular weight of the antibodies, mass spectrometry was performed on intact and reduced antibody samples and are shown in FIG. 30 A-G. The molecular weights match the predicted molecular weights for all of the antibodies tested and the amino acid sequences confirmed. No other liabilities were flagged. Overall, the purified chimeric and humanized antibodies passed QC.

Kinetic Studies of the Humanized Tau01 Candidate Antibodies to TauC3

To determine the affinity of the binding interactions, a biacore kinetic assay was developed which involved immobilizing TauC3 on a CM5 chip via amine coupling and injecting a concentration series of the respective antibody over it. The chimeric antibody binds to TauC3 with a KD of 57 pM (FIG. 31 A).

FIG. 31 B shows Tau01 HCKB is the weakest binder to TauC3 (1.2 nM) followed by HMKM which binds to TauC3 with an affinity of 110 pM (FIG. 31 G). Tau01 HMKO, HMKN, HMKP and HMKE, shown in FIG. 31 C-F, have KD values comparable or tighter than the chimeric antibody. However, the off-rate is slightly faster for all humanized candidates compared to the chimeric (0.001-0.004 for humanized vs 0.0007 for the chimeric). It should be noted that the ka is at the limits of the instrument so the absolute values should be compared with caution. It can be concluded that the antibodies HMKN, HMKP and HMKE bind in the picomolar range and have the slowest off-rates of all the humanized variants tested.

Determination of the Melting Temperature (Tm) of Humanized Tau01 Candidate Antibodies In order to determine the melting temperature of the lead antibodies Tau01 HMKE, HMKM, HMKN, HMKO, HMKP a thermal shift assay was performed. Samples were incubated with a fluorescent dye (Sypro Orange) for 71 cycles with 1° C. increase per cycle in a qPCR thermal cycler (Section 8.21). Tm for the humanized antibodies were calculated to be 68-69° C. (FIG. 32).

Non-Specific Protein-Protein Interactions (CIC) of Humanized Tau01 Candidate Antibodies Cross-Interaction Chromatography using bulk purified human polyclonal IgG is a technique for monitoring non-specific protein-protein interactions and can provide an indication of any solubility issues, which can give rise to downstream manufacturing problems, as explained in Example 5. An elevated Retention Index (k') indicates a self-interaction propensity and a low solubility. Humanized Tau01 HMKE, HMKM, HMKN, HMKO, HMKP candidate antibodies show a Retention Index below 0.038, indicating a low propensity for non-specific interactions and good solubility (FIG. 33).

Solubility of Humanized Tau01 Candidate Antibodies

The humanized Tau01 HMKE, HMKM, HMKN, HMKO, HMKP candidate antibodies were concentrated using solvent absorption concentrators (MWCO 7500 kDa) and the concentration measured at timed intervals. Tau01 HMKP was concentrated to 123 mg/ml and Tau01 HMKN, HMKM and MoTau01 HuG4K antibodies were concentrated to 87-88 mg/mL (FIG. 34). Tau01 HMKO HuG4K was concentrated to 59 mg/ml without apparent precipitation and Tau01 HMKE HuG4K was concentrated to 57 mg/ml. The data suggest that the antibodies are not prone to precipitation at concentrations of up to 57 mg/mL.

Freeze/Thaw and Heat Stress Analysis of Humanized Tau01 Candidate Antibodies by Circular Dichroism Circular Dichroism (CD) is a spectroscopic technique which allows us to observe the overall secondary structure of a purified protein sample.

The freeze-thaw (FT) stress experiment involved subjecting samples of the purified candidate antibodies to 10 cycles of 15 minutes at −80° C. followed by thawing for 15 minutes at room temperature. To perform the heat stress experiment, samples of the purified candidate antibodies were exposed to temperatures of; a) 4° C., b) room temperature (RT), c) 37° C. and d) 50° C. for 25 days.

Samples were then analyzed by Circular dichroism to check if secondary structure had been retained (FIG. 35). All the humanized variants tested passes our internal threshold. Overall, the data suggests that the heat stress and freeze/thaw cycles do not affect the secondary structure of the humanized Tau01 HMKE, HMKM, HMKN, HMKO, HMKP candidate antibodies.

Isoelectric Point Analysis of Humanized Tau01 Candidate Antibodies pI analysis of the humanized candidate antibodies was performed using capillary isoelectric focusing (cIEF). This technique allows antibodies to be separated according to their isoelectric point (pI) using a pH gradient across the capillary. FIG. 36 shows the chromatograms and Table 15 displays the main pI isoform(s) of each antibody (defined as greater than 10% peak area) and the pI range for each antibody. The main isoelectric points for humanized Tau01 HMKE, HMKM, HMKN, HMKO, HMKP candidates are ~8.86-8.81.

Serum Stability Assessment of Humanized Tau01 Candidate Antibodies

Purified samples of the chimeric and humanized antibodies were incubated in mouse, human and cynomolgus serum for 21 days. The binding of the Tau01 HMKE, HMKM, HMKN, HMKO, HMKP candidate antibodies which had been incubated in the 3 different serums were compared with an antibody incubated in PBS and a 4° C. positive control sample by binding ELISA to TauC3 (FIG. 37). The Tau01 HMKE, HMKM, HMKN, HMKO, HMKP candidate antibodies retained their binding capability after being incubated in mouse, human and cynomolgus serum.

Summary of Data for the Lead Tau01 HMKE HMKN, HMKO, HMKP, HMKM Humanized Candidates Compared to MoTau01 HuG4k Table 16 shows a summary of the binding, kinetic affinity and biophysical properties of the lead humanized Tau01 HMKE HMKN, HMKO, HMKP, HMKM antibody candidates compared to the chimeric antibody MoTau01 HuG4k. All of the humanized candidates bind in the picomolar range but of these, Tau01 HMKN, HMKO and HMKP have the highest affinities and slowest off-rates and also pass all of our biophysical assays. Taking all the data into account, Tau01 HMKP was chosen as the lead humanized candidate as it has the highest affinity, a slow off-rate and shows no potential liabilities in the biophysical assays. Tau01 HMKN and Tau01 HMKO and KMKE are all good back up humanized lead candidates as they also have excellent properties.

TABLE 16

Final humanized candidate antibody summary

| | MoTau01 HuG4k | Tau01 HMKN HuG4k | Tau01 HMKO HuG4k | Tau01 HMKP HuG4k | Tau01 HMKE HuG4k | Tau01 HMKM HuG4k |
|---|---|---|---|---|---|---|
| Expression | 213.2 mg/L | *40 mg/L | *44 mg/L | 153 mg/L | 262.5 mg/L | 221.2 mg/L |
| ka (1/Ms) | $1.29 \times 10^7$ | $6.03 \times 10^7$ | $5.93 \times 10^7$ | $1.43 \times 10^7$ | $1.41 \times 10^8$ | $1.65 \times 10^8$ |
| kd (1/s) | $7.41 \times 10^{-4}$ | $1.50 \times 10^{-3}$ | $3.52 \times 10^{-3}$ | $1.86 \times 10^{-3}$ | $2.83 \times 10^{-3}$ | $1.81 \times 10^{-2}$ |
| KD (pM) | 57 | 25 | 59 | 13 | 20 | 110 |
| pI range | 6.68-7.16 | 8.17-8.61 | 8.18-8.61 | 8.36-8.87 | 8.38-8.94 | 8.29-8.57 |
| Average Tm (° C.) | 62 | 69 | 69 | 68 | 68 | 69 |
| Thermal stability | <60° C. | >67° C. | >67° C. | >67° C. | >67° C. | / |
| Solubility | ≥80 mg/ml | ≥80 mg/ml | ≥50 mg/ml | ≥100 mg/ml | ≥50 mg/ml | ≥80 mg/ml |
| CD-50° C. incubation | No data | pass | pass | pass | pass | pass |
| CD-repeated freeze-thaw | No data | pass | pass | pass | pass | pass |
| SEC-MALS-repeated freeze-thaw | <0.5% aggregation | 0 | / | / | / | / |
| Non-specific interactions | −0.01-Pass | 0.022-Pass | 0.03-Pass | 0.038-Pass | 0.025-Pass | −0.080-Pass |

TABLE 16-continued

Final humanized candidate antibody summary

|  | MoTau01 HuG4k | Tau01 HMKN HuG4k | Tau01 HMKO HuG4k | Tau01 HMKP HuG4k | Tau01 HMKE HuG4k | Tau01 HMKM HuG4k |
|---|---|---|---|---|---|---|
| Serum stability | Binding retained in all sera | Binding retained in all sera | Binding retained in all sera | Binding retained in all sera | Binding retained in all sera | Binding retained in all sera |
| No of aa identical to germline |  | 83 | 84 | 82 | 83 | 82 |
| % ID with germline V-segment* |  | 87.4 | 88.4 | 86.3 | 87.4 | 86.3 |

CONCLUSION

The aim of this project was to humanize the MoTau01 antibody and to ensure the resulting antibody is capable of binding to TauC3 with comparable affinity when compared to the chimeric antibody. The MoTau01 antibody has been engineered and expressed as a humanized antibody without significant loss of binding affinity. The Tau01 HMKE, HMKM, HMKN, HMKO, HMKP humanized antibodies showed high affinities in binding ELISAs, Octet ranking and kinetic studies using Biacore, in the picomolar range (FIG. 31) and also pass all of our biophysical assays.

The Tau01 HMKP antibody shows the best drug-like characteristics as well as excellent kinetics of binding so was chosen as the lead candidate (Table 16). In our view the combination of the excellent binding, expression, thermostability, affinity and biophysical characterization properties make Tau01 HMKP a suitable candidate antibody for further development. Tau01 HMKN, HMKO and HMKE also exhibit excellent properties and are very good back up humanized lead candidates.

Example 5 (Protocols)

The following protocols/procedures were used in Examples 1-4.

RNeasy Mini Protocol for Isolation of Total RNA (Qiagen)
1. Disrupt cells by addition of Buffer RLT. For pelleted cells, loosen the cell pellet thoroughly by flicking the tube. Add Buffer RLT (600 μl), and proceed to step 2. Note: Incomplete loosening of the cell pellet may lead to inefficient lysis and reduced yields.
2. Homogenize cells passing the lysate at least 5 times through an 18-20-gauge needle fitted to an RNase-free syringe.
3. Add 1 volume of 70% ethanol to the homogenized lysate, and mix thoroughly by pipetting. Do not centrifuge. The volume of lysate may be less than 600 μl due to loss during homogenization.
4. Transfer up to 700 μl of the sample, including any precipitate that may have formed, to an RNeasy spin column placed in a 2 mL collection tube. Close the lid gently, and centrifuge for 15 s at ≥8000×g. Discard the flow-through. Reuse the centrifuge tube in step 5.
5. Add 700 μl Buffer RW1 to the RNeasy column. Close the lid gently, and centrifuge for 15 s at ≥8000×g to wash the column membrane. Discard the flow-through. Reuse the centrifuge tube in step 6.
6. Add 500 μl Buffer RPE to the RNeasy column. Close the lid gently, and centrifuge for 15 s at ≥8000×g to wash the column membrane. Discard the flow-through. Reuse the centrifuge tube in step 7.
6. Add another 500 μl Buffer RPE to the RNeasy column. Close the lid gently, and centrifuge for 2 min at ≥8000×g to dry the RNeasy spin column membrane.
7. Place the RNeasy spin column in a new 2 mL collection tube and discard the old collection tube with the flow-through. Close the lid gently and centrifuge at full speed for 1 min.
8. To elute, transfer the RNeasy column to a new 1.5 mL collection tube. Add 30 μl of RNase-free water directly onto the RNeasy spin column membrane. Close the tube gently. Let it stand for 1 min, and then centrifuge for 1 min at ≥8000×g.

Protocol for $1^{st}$-Strand cDNA Synthesis (GE Life Sciences)
1. Place the RNA sample in a microcentrifuge tube and add RNase-free water to bring the RNA to the appropriate volume (20 μL-12× dilution, see Table A).
2. Heat the RNA solution to 65° C. for 10 minutes, then chill on ice. Gently pipette the Bulk First-Strand cDNA Reaction Mix to obtain a uniform suspension. (Upon storage, the BSA may precipitate in the Mix; this precipitate will dissolve during incubation).
3. Add Bulk First-Strand cDNA Reaction Mix (11 μL) to a sterile 1.5 or 0.5 mL microcentrifuge tube. To this tube add 1 μL of DTT Solution, 1 (0.2 μg, 1:25 dilution) of NotI-d(T)18 primer and the heat-denatured RNA. Pipette up and down several times to mix.
4. Incubate at 37° C. for 1 hour and heat inactivate transcriptase for 5 min at 95° C.

TABLE A

Volumes of Components in First-Strand Reaction

| Bulk $1^{st}$ Strand Reaction Mix | Primer | DTT | RNA | Final Volume First-Strand Reaction |
|---|---|---|---|---|
| 11 μL | 1 μL | 1 μL | 20 μL | 33 μL | cDNA Purification
1. A simple protocol designed to remove contaminating First-Strand cDNA primer that could interfere with subsequent PCR reactions.
2. Add 99 μl of Buffer QG (from Qiagen Gel Extraction Kit, Cat. No: 28704) and 33 μl IPA. Mix and add to a QiaQuick Gel Extraction Column. Spin and discard the flow-through.

3. Wash the column once with 500 µl Buffer QG. Discard the flow-through.
4. Wash the column once with 750 µl Buffer PE. Discard the flow-through.
5. Spin the column to remove any residual alcohol and allow the column to dry.
6. Elute the cDNA with 50 µl distilled water pre-heated to 65° C.

PCR Cloning of Mouse Variable Regions

1. Set up PCR reactions on the purified cDNA using the primers in Tables 1 and 2. Use a different forward primer in each reaction (MHV1-12 and 14 and MKV 1-11) as follows:

| *Kappa chain | *Heavy chain |
| --- | --- |
| 9 µl sterile water | 9 µl sterile water |
| 12.5 µl Phusion Flash Master Mix | 12.5 µl Phusion Flash Master Mix |
| 1.25 µl 10 µM MKCv2 primer | 1.25 µl 10 µM of MHCv2 primer mix |
| 1 µl 1st strand reaction cDNA template. | 1 µl 1st strand reaction cDNA template. |

*To each reaction add 1.25 µl of the appropriate MKV-v2 (Table 1) or MHV-v2 (Table 2) Forward primer 2. Cycle:

| | 3-step protocol | | |
| --- | --- | --- | --- |
| Cycle step | Time | Temp. | Cycles |
| Initial denaturation | 98° C. | 10 s | 1 |
| Denaturation Temp. | 98° C. | 1 s | 30 |
| Annealing | 60° C. | 5 s | |
| Extension | 72° C. | 6-7 s | |
| Final extension | 72° C. | 1 min | 1 |
| | 4° C. | hold | |

3. Electrophorese a 5 µl sample from each PCR-reaction on a 2% (w/v) agarose gel to determine which of the leader primers produces a PCR-product. Positive PCR-clones will be about 420-500 bp in size.
4. For the positive clones, PCR purify the remaining sample using the QIAGEN PCR Purification Kit, eluting into 40 µL nuclease-free water. Send to an outside contractor (e.g. GATC) for PCR-fragment sequencing using the M13 Forward and M13 Reverse primers.

QIAquick PCR Purification Microcentrifuge and Vacuum Protocol (QIAGEN)

1. All centrifugation steps are at 17,900×g (13,000 rpm) in a conventional table top microcentrifuge.
2. Add 5 volumes of Buffer PB to 1 volume of the PCR reaction and mix. If the colour of the mixture is orange or violet, add 10 µl of 3 M sodium acetate, pH 5.0, and mix. The colour of the mixture will turn yellow.
3. Place a QIAquick column in a provided 2 mL collection tube or into a vacuum manifold.
4. To bind DNA, apply the sample to the QIAquick column and centrifuge for 30-60 s or apply vacuum to the manifold until all samples have passed through the column. Discard flow-through and place the QIAquick column back into the same tube.
5. To wash, add 0.75 mL Buffer PE to the QIAquick column and centrifuge for 30-60 s or apply vacuum. Discard flow-through and place the QIAquick column back in the same tube.
6. Centrifuge the column in a 2 mL collection tube (provided) for 1 min.
7. Place each QIAquick column in a clean 1.5 mL microcentrifuge tube.
8. To elute DNA, add 40-50 µl Buffer EB (10 mM Tris.Cl, pH 8.5) to the centre of the QIAquick membrane and centrifuge the column for 1 min.

Generation of mAb Expression Vectors by LIC

Insert Preparation

1. Use sequence to generate LIC primers.
2. Perform LIC PCR on codon optimised, synthesised genes (Genscript) using LIC primers (Table 4).
3. Set up PCR reactions:

| Reagent | Volume (for 20 µl final reaction volume) |
| --- | --- |
| H$_2$O | add to 50 µl |
| 2x Phusion PCR Master Mix | 25 µl |
| Primer Rev | 2.5 µl, Cf = 0.5 µM |
| Primer For | 2.5 µl, Cf = 0.5 µM |
| DNA | 1 µl |

Note:
Polymerase that generates blunt ended PCR products must be used in this step. Other Polymerases which produce T overhangs are not suitable.

4. Cycle:

| | 3-step protocol | | |
| --- | --- | --- | --- |
| Cycle step | Time | Temp. | Cycles |
| Initial denaturation | 98° C. | 10 s | 1 |
| Denaturation Temp. | 98° C. | 1 s | 30 |
| Annealing | 72° C. | 5 s | |
| Extension | 72° C. | 15 s/1 kb | |
| Final extension | 72° C. | 1 min | 1 |
| | 4° C. | hold | |

5. Run 5 µL of PCR products on a gel to ensure correct sized product—should be around 370 bp.
6. PCR purify products using Qiagen PCR purification kit to remove nucleotides and primers. Elute into 40 µL nuclease-free water.
7. T4 DNA Polymerase treat inserts:

| PCR product | 40 µL |
| --- | --- |
| 10 × NEB 2 | 4.5 µL |
| dTTP (100 mM) NEB | 1.25 µL |
| T4 DNA Polymerase NEB | 1 µL |

8. Incubate at RT for 30 min and then inactivate enzyme at 70° C. for 20 min.

Vector Preparation

9. Digest the LIC vectors (vector maps shown in FIGS. 3 and 4) with BfuAI by incubating at 50° C. for 3 hours or overnight:

| 10x NEB buffer 3 | 10 µL |
| --- | --- |
| 100x BSA | 1 µL |
| BfuA1 | 5 µL |
| LIC vector | 5 µg |
| dH$_2$0 | to 100 µL |

10. Following BfuAI digestion add: 24, of Bam HI and incubate at 37° C. for 2 hours.

11. Run the digested vector on a 1% (w/v) agarose/1×TAE gel containing 1×SYBR Safe DNA Stain. Two bands may be visible—cut out the higher MW band and extract using gel extraction kit, elute in 50 μL of EB.
12. T4 DNA polymerase treat the vector as follows:

| | |
|---|---|
| 10x NEB buffer 2 | 6 μL |
| 100 mM dATP | 1.5 μL |
| T4 DNA Pol | 1 μL |
| BfuA1 digested vector | 50 μL |

13. Incubate at RT for 30 min and then inactivate the enzyme at 70° C. for 20 min.

Cloning

14. Mix 1 μL of insert with 0.5 μL vector in a total of 10 μL nuclease-free water for 20 min RT. Always perform vector alone transformation.
15. Use the ligation mix to transform 25-504, of chemically competent Invitrogen TOP 10 bacteria following the manufacturer's instructions and spread on 90 mm diameter LB agar plates containing Kanamycin (50 μg/mL). Incubate overnight at 37° C.

Pick Colonies from Transformation

16. PCR confirm using Phusion PCR Master Mix:

| Reagent | Volume (for 20 μl final reaction volume) |
|---|---|
| 2x Phusion PCR Master Mix | 25 μL |
| HCMVi primer | 1 μL |
| HuG4/HuK LIC primer | 1 μL |
| dH₂0 | to 23 μL |
| DNA | Dip of colony (grow day culture of same colony) |

| | 3-step protocol | | |
|---|---|---|---|
| Cycle step | Time | Temp. | Cycles |
| Initial denaturation | 98° C. | 30 s | 1 |
| Denaturation Temp. | 98° C. | 30 s | 25-30 |
| Annealing | 65° C. | 5 s | |
| Extension | 72° C. | 15 s/1 kb | |
| Final extension | 72° C. | 5 min | 1 |
| | 4° C. | hold | |

17. Run each PCR-reaction on a 2% agarose e-gel cassette and run for 15 min to determine the size of any PCR-product bands on the gel.
18. Grow starter cultures overnight using LB supplemented with Kanamycin to miniprep constructs and sequence the DNA (using the same primers) from at least two separate positive clones of the variable genes to identify any possible errors due to the PCR-reaction itself.

Transformation of TOP10™ E. coli (Invitrogen Protocol)
1. Centrifuge the vial(s) containing the ligation reaction(s) briefly and place on ice.
2. Thaw, on ice, one 50 μL vial of One Shot cells for one or two ligations/transformations.
3. Pipet 1 to 2 μL of each ligation reaction directly into vial of competent cells and mix by tapping gently. Do not mix by pipetting up and down. The remaining ligation mixture(s) can be stored at −20° C.
4. Incubate the vial(s) on ice for 15-30 minutes.
5. Incubate for exactly 30 seconds in the 42° C. water bath then place on ice for 2 min.
6. Add 250 μL of pre-warmed S.O.C. medium to each vial.
7. Shake the vial(s) at 37° C. for exactly 1 hour at 225 rpm in a shaking incubator.
8. Spread 200 μL from each transformation vial on separate, labeled LB agar plates containing 500 μg/mL kanamycin.
9. Invert the plate(s) and incubate at 37° C. overnight.

Plasmid DNA Miniprep Isolation Using QIAprep® (Qiagen Protocol)
1. Resuspend pelleted bacterial cells in 250 μL Buffer P1 and transfer to a microcentrifuge tube. Ensure that RNase A has been added to Buffer P1.
2. Add 250 μL Buffer P2 and invert the tube gently 4-6 times to mix.
3. Add 350 μL Buffer N3 and invert the tube immediately but gently 4-6 times. The solution should become cloudy.
4. Centrifuge for 10 min at 13,000 rpm (~17,900×g) in a table-top microcentrifuge. A compact white pellet will form.
5. Apply the supernatant from step 4 to the QIAprep Spin Column by pipetting.
6. Centrifuge for 30-60 s. Discard the flow-through.
7. Wash column by adding 0.5 mL of Buffer PB and centrifuging for 30-60 s.
8. Wash column by adding 0.75 mL Buffer PE and centrifuging for 30-60 s.
9. Discard the flow-through and centrifuge for an additional 1 min.
10. Place the QIAprep column in a clean 1.5 mL microcentrifuge tube. To elute DNA, add 50 nuclease-free water to the center of the QIAprep Spin Column, let stand for 1 min, and centrifuge for 1 min.

ExpiCHO Transfection in 24-Well Plates 1 ml Transfection (the ExpiCHO™ Expression System Kit—Invitrogen)
1. Subculture and expand expiCHO cells until the cells reach a density of approximately $4\text{-}6\times10^6$ viable cells/mL.
2. On the day prior to transfection (Day −1), split the expiCHO culture to a final density of $3\text{-}4\times10^6$ viable cells/mL and allow the cells to grow overnight.
3. Dilute cells to $6\times10^6$ viable cells/mL.
4. Aliquot 0.9 mL of cells into each well of the 24-well plate to be used for transfection.
5. Prepare ExpiFectamine/DNA complexes.
6. Dilute plasmid DNA by adding 1 μL DNA to a final volume of 50 μL OptiPro for each well to be transfected (1 ug of plasmid DNA per mL of culture volume to be transfected).
7. Dilute 4 μL ExpiFectamine CHO reagent in 46 μL OptiPro medium for each well to be transfected (no incubation time required).
8. Add the diluted ExpiFectamine CHO to the diluted DNA and mix by gentle pipetting 3-4 times (incubation 1 to 5 min).
9. Add 100 μL of the complexation mixture to each well containing culture in the 24-well plate.
10. Cover the plates with a gas-permeable lid.
11. Incubate the 24-well plate in a 37° C. incubator with 8% CO2 on an orbital shaker (recommended shake speed 225 rpm for shakers with a 19 mm orbital throw).

12. Add ExpiFectamine Enhancer (6 ul ExpiCHO enhancer) and ExpiCHO Feed (190 ul ExpiCHO feed) 18-22 hours post-transfection
13. Protein expression is typically complete and supernatant ready to be harvested by Day 7-8 post transfection.

IgG quantitation by Octet
1. Prepare 100 µl of each concentration of standard curve and ExpiCHO supernatant as follows:
    a. HuG4K Isotype standard at 500, 250, 125, 62.5, 31.25, 15.6, 7.81, 3.9 µg/ml, using ExpiCHO expression medium as a diluent
    b. Test (unknown) samples
2. Pre-soak (≥10 mins) protein G-coated biosensors (Pall ForteBio) in 200 µl ExpiCHO expression medium.
3. Aliquot 45 µl standards and test samples into a 384-well tilted-bottom plate in duplicate, including a media only control. Seal plate and spin (1000 rpm for 1 min) in bench-top centrifuge.
4. Remove plate seal and insert plate and presoaked sensors into Octet.
5. Perform quantitation as follows:
    a. Regenerate protein G-coated sensors in 10 mM glycine, pH1.5 for 5 seconds and neutralize in ExpiCHO expression medium for 5 seconds. Repeat three times.
    b. Measure standard or sample for 120 seconds.
    c. Repeat regeneration and neutralization step as above.
6. Import data into analysis software and fit data to a dose response-5PL weighted fit to give IgG concentrations in µg/ml.

TauC3 Binding ELISA
1. Coat each well of a 94/384-well MaxiSorp plate with 50/30 µL aliquots of 1 µg/mL of TauC3 in PBS per well in a 96/384-well plate respectively. Incubate overnight at 4° C.
2. Wash 3× with PBS-T (0.1% Tween20).
3. Block with 150/80 µL of PBS+5% BSA+0.1% Tween 20 per well in a 96/384-well plate respectively.
4. Incubate at 37° C. for 1 hour. Wash 3× with PBS-T (0.1% Tween20).
5. Add 50/30 µl of primary antibody serially diluted in PBS+0.2% BSA+0.1% Tween 20 to the assay plate (96/384-well plate respectively). Use a 3-fold dilution series starting from ~4 µg/mL. Repeat the incubation and washing step (step 4).
6. Dilute the anti-human kappa chain HRP (Sigma A7164-1 mL) 3 ul per 10 ml in PBS+0.2% BSA+0.1% Tween 20 and add 50/30 µL to each well in a 96/384-well plate respectively. Repeat the incubation and washing step (step 4).
7. Add 75/20 µL of K-Blue substrate (Neogen) per well and incubate for 5-10 minutes at RT.
8. Stop the reaction by adding 50/10 µl of RED STOP solution (Neogen) to each well in a 96/384-well plate respectively.
9. Read the optical density at 650 nm using the Pherastar Plus.

Tau01 Variant Screening and Affinity Determination by Octet
1. Immediately prior to use, incubate protein G-coated sensors (Pall ForteBio) in HBS-P$^+$ buffer for 10 min.
2. Load 1 µg/mL antibody in HBS-P$^+$ onto Protein G sensors for 600 seconds (immobilisation level of 0.8-1 nm).
3. Allow sensors to equilibrate in HBS-P$^+$ for 180 seconds.
4. For screening assay, perform association step using 10 nM TauC3 for 600 seconds. For kinetics assay, load ~0.5 µg/mL antibody in HBS-P$^+$ for 10 mins and perform association step using a concentration range from 20 nM to 0.31 nM TauC3 for 10 mins.
5. Perform dissociation step in HBS-P$^+$ for 600 seconds.
6. Regenerate sensors with 10 mM glycine, pH1.5-2.0 for 5-30 seconds and neutralise by incubating in HBS-P$^+$ buffer for 30-60 seconds. Repeat three times.

QuikChange Lightning Site-Directed Mutagenesis Kit (Stratagene)
1. Prepare the reaction(s) as indicated below:
    a. 5 µL of 10× reaction buffer
    b. 0.12 µL (25 ng) of RHA or RKA template
    c. 1.3 µL (125 ng) of oligonucleotide mutation primer For
    d. 1.3 µL (125 ng) of oligonucleotide mutation primer Rev
    e. 1 µL of dNTP mix
    f. 1.5 µL of QuikSolution reagent
    g. ddH2O to a final volume of 50 µL
    h. 1 µL of QuikChange Lightning Enzyme.
2. Cycle each reaction using the cycling parameters outlined in the following table:

| Cycle step | 3-step protocol | | |
|---|---|---|---|
| | Time | Temp. | Cycles |
| Initial denaturation | 95° C. | 2 min | 1 |
| Denaturation Temp. | 95° C. | 20 s | 18 |
| Annealing | 60° C. | 10 s | |
| Extension | 68° C. | 3 min | |
| Final extension | 68° C. | 5 min | 1 |
| | 4° C. | hold | |

3. Add 2 µL of the Dpn I restriction enzyme
4. Gently and thoroughly mix each reaction, microcentrifuge briefly, then immediately incubate at 37° C. for 5 min to digest the parental dsDNA
5. Transform 2 µL of the Dpn I-treated DNA from each reaction into separate 45-4, (+2 µL β-ME) aliquots of XL10-Gold ultracompetent cells (see Transformation of TOP 10Tm E. coli).
6. Screen colonies using the Phusion method, miniprep and sequence to check for the correct mutation.

Qiagen HiSpeed Maxiprep System Protocol
1. Pick from a freshly streaked selective plate or a glycerol stock of the clone of interest and inoculate a starter culture of 2-5 ml LB media supplemented with Kanamycin. Incubate for ~8 hours at 37° C. with 250-300 rpm shaking.
2. Dilute the starter culture 1/1000 and inoculate 150-250 mL of LB media supplemented with Kanamycin from the starter culture and incubate overnight at 37° C. with 250-300 rpm shaking (12-16 hours).
3. Harvest the cells at 6,000×g for 15 mins. Discard the supernatant.
4. Resuspend cell pellet thoroughly in 10 mL of Buffer P1 by vortexing or pipetting.
5. Add 10 mL of Buffer P2. Invert vigorously 4-6 times to mix. Incubate for 5 min at room temperature.
6. Add 10 mL of chilled Buffer P3. Invert vigorously 4-6 times to mix.
7. Pour lysate into the barrel of a QIAfilter Cartridge. Incubate at room temperature for 10 min.

8. Equilibrate a HiSpeed Maxi Tip by applying 10 ml Buffer QBT and allow to empty by gravity flow.
9. Using a QIAfilter, filter the lysate into the equilibrated HiSpeed Maxi Tip. Allow the lysate to enter the resin by gravity flow.
10. Wash the HiSpeed Maxi Tip with 60 ml Buffer QC.
11. Elute DNA with 15 ml Buffer QF
12. Precipitate DNA by adding 10.5 ml isopropanol to the eluted DNA. Mix and incubate at room temperature for 5 min.
13. Transfer the eluate/isopropanol mixture into a 30 ml syringe and filter through the QIAprecipitator module.
14. Wash the DNA in the QIAprecipitator with 2 ml 70% Ethanol. Dry the membrane by pressing air through the QIAprecipitator numerous times.
15. Using a 5 ml syringe, elute the DNA in 1 ml nuclease-free water. Transfer the eluate into the syringe and elute for a second time.

Thermal Stability Comparison

1. Dilute fully humanized antibodies and the chimeric control to 1 µg/mL in PBS/0.2% Tween and aliquot at the appropriate volume for the EC80 concentration into PCR tubes. Bring the volume up to 100 µl with the same buffer.
2. Heat separately each tube for 10 min at temperatures between 30° C. and 85° C. with a 5° C. interval and cool to 4° C.
3. Freeze down the 1 µg/mL stock for 1 h and then dilute to the EC80 concentration.
4. Perform the binding assay against TauC3 (Section 8.11) using 100 µl of each antibody per well (assay each temperature in duplicate) in a 96-well plate.

Biacore Off-Rate Ranking and Kinetic Studies of the Tau01 Humanized Antibodies

Off-Rate Ranking

1. Amine couple 0.5 µg/mL Human TauC3 in Acetate buffer pH 5 on 1 flow channel in a CMS chip (GE Healthcare). Use the immobilization wizard to aim for ~15 RU with HBS-EP+ as the running buffer.
2. Load antibody supernatants at 2.5 nM HBS-EP+ buffer at a flow rate of 30 µL/min for 300 s followed by 600 s dissociation and a 30 s regeneration using 3M MgCl$_2$. Export the raw data, subtract the buffer baseline and fit the data using a one-phase decay or two-phase decay in GraphPad Prism.

Kinetics

1. Amine couple 0.5 µg/mL Human TauC3 in Acetate buffer pH 5 on 1 flow channel in a CM5 chip. Use the immobilization wizard to aim for ~15 RU with HBS-EP+ as the running buffer.
2. Dilute each antibody to 5 nM and produce a 2-fold dilution series down to 0.08 nM in HBS-EP+ buffer. Inject each concentration at 30 µL/min for 300 s, followed by a dissociation of 600 s, a 30 s regeneration using 3M MgCl$_2$ and a stabilization period of 600 s between cycles. Fit the data using a 1:1 Global fit.

Binding Test FL Tau

1. Load 0.25 µg/mL antibody in HBS-EP+ buffer on a Protein G chip (GE Healthcare) at 10 µL/min for 30 s. Increase the flow rate to 30 µL/min and add 250 nM FL Tau in HBS-EP+ buffer for 180 s. Regenerate using 10 mM Glycine pH 1.5 for 30 s Purification of Antibody Candidates Instrument: GE Healthcare AKTAxpress™ Purification System
Software: UNICORN
Columns: HiTrap MabSelect SuRe, 1 mL; HiLoad 16/600 Superdex 200 pg
Mobile phase: IgG Elution Buffer; Dulbecco's 1×PBS
Sample prep: Filtering through 0.22 µm
Injection volume: 200 mL Expi293 conditioned medium (1:1) in DPBS
Flow rate: Sample loading at 0.5 mL/min; Gel filtration at 1.5 mL/min;
Elution at 1 mL/min

SEC-MALS 1. 10 µl of each sample (1 mg/mL) was injected onto a SEC column (AdvanceBio SEC 300 Å, 4.6×150 mm, 2.7 µm, LC column, Agilent) and subsequently detected by three in-series detectors:
    a. UV (Agilent 1260 Infinity HPLC system with thermostated column compartment)
    b. Light-scattering (Wyatt Technology DAWN HELEOS)
    c. Differential Refractometer (Wyatt Technology Optilab TRex)
2. A constant flow-rate of 0.4 mL/min was applied using a mobile phase of Gibco's PBS (ThermoFisher) containing 0.05% sodium azide. All experiments were carried out at 25° C.
3. The data was analyzed with Wyatt Technology ASTRA software (version 6.1.2.83) and with the refractive index increment (dn/dc) set to 0.185 (i.e. for protein analysis).
4. All samples were stored at 4° C., prior to analysis by SEC-MALS.

Dynamic Light Scattering (DLS)

1. Prepare 50 µl samples at 1.3 mg/ml (in Dulbecco's PBS; Sigma D8537) and aliquot into a 384-well polypropylene plate (Greiner bio-one).
2. Data is recorded on a Zetasizer APS (Malvern). All values were recorded in triplicate and processed using the associated Zetasizer software (version 7.11).
3. A cumulants analysis was performed to obtain mean particle size (z-average) and the polydispersity index (PDI).

Mass Spectrometry

Mass spectrometry of purified chimeric and humanized candidate antibodies is depicted in FIG. 30.

Thermal Shift Comparison

1. Prepare samples directly into 96 well white PCR plate in a final volume of 25 µL (purified antibody final concentration of 1 and 2 µM).
2. Sypro Orange—make stock 1:100 in PBS buffer, then add 1:10 to final samples (e.g. 2.5 µL in 25 µL)
3. Load into the qPCR machine and use the MxPro software, SYBR Green method, (filter=FRROX, no reference dye). Thermal profile setup—71 cycles of 1° increase
4. Plot the results and determine Tm.

Cross-Interaction Chromatography (CIC)

1. Samples were analyzed by two separate 20 µl injections (0.5 mg/mL); firstly onto a 1 mL NHS activated resin (GE Healthcare) coupled with 30 mg human polyclonal IgG (Sigma 14506) and secondly onto a 1 mL NHS activated resin blank coupled, as control column.

2. The mobile phase consisted of Dulbecco's PBS (Sigma D8537) containing 0.01% sodium azide (0.1 mL/min) and all experiments were performed at 25° C.
3. Eluted samples were detected by UV absorbance (Agilent 1260 Infinity HPLC system with thermostatted column compartment) and data was analyzed using Wyatt Technology ASTRA software (version 6.1.2.83) to determine sample peak retention times. These were then used to calculate a retention factor k':

$$k' = \frac{(Tr - Tm)}{Tm}$$

where $T_r$ is the retention time of the sample on the poly-IgG column and $T_m$ is the retention time on the mock (control) column.

Solubility

Load a Vivapore solvent absorption concentrator 7500 kDa MWCO (VP0502 Satorius) with 3.5-5.0 ml antibody solution at 1 mg/ml in PBS.
1. Monitor antibody concentration every 10 min by sampling a small amount for measuring on the Nanodrop 2000 ($\varepsilon$=1.4) and continue until the concentrated volume reaches the dead volume of ~30-50 µl.
2. Plot the concentration values (mg/ml) against the corresponding time points to generate the concentration profiles.

Circular Dichroism
1. Prepare 30 µL of sample, at 1 mg/ml (in Dulbecco's PBS; Sigma D8537).
2. Dilute the 1 mg/mL sample to 0.15× with 10 mM Phosphate buffer.
3. Readings were taken in a 1 mM spectrosil cuvette. Readings were taken with a DIT of 4 seconds, and a scanning speed of 20 nm/min, with a step size of 1 nm.
4. The averaged blank spectra was subtracted from the sample spectra, and then spectra converted to $\Delta\varepsilon$. Spectra were then zeroed against their 256-260 nm values. Smoothing was performed by savitsky-golay filter via a custom excel function, sgFilter( ) using a quadratic polynomial with a a window size of 7 (–2, 3, 6, 7, 6, 3, –2). Spectra are shown with error bars, which are the average of the standard deviation at wavelengths +/–2 nm.

pI Analysis Using cIEF
1. Samples were concentrated to >5 mg/ml and desalted to <50 mM NaCl levels whereupon 10 µl was added to 240 µl of a pharmalyte/urea gel mastermix that contains the pI markers of 4.5/5.1/9.5 and 10.
2. The sample was mixed for at least 5 min and then 200 µl was added to the sample PCR vial.
3. Samples were loaded onto the PA800 sample block along with the cIEF gel, catholyte, anolyte and chemical mobilizer rinse buffers into the chemical buffer block. The PA800 was loaded with a neutral capillary and the default "condition" method is run to prepare the capillary for sample analysis.
4. Each sample was run using the correct "separation" method that is dependant on the level of Urea present within the sample.
5. Data is analysed using 32 Karat software and the pI markers provide the standard curve to quantify the sample peak pI values.

Antibody Serum Stability Assessment
1. Prepare 600 µl of polished antibody at 0.4 mg/mL in PBS.
2. Use Mouse serum (SCD-808), Human serum (S-123) and Cyno serum (S-118) from Seralab. Aliquot 150 ul serum and PBS control in a round bottom 96-well plate and add 50 ul 0.4 mg/mL antibody solution in PBS (final concentration of 100 ug/mL) in triplicates to each serum type in a tissue culture cabinet (BSL-2). Keep some at 4° C. to use as a control.

Serum Incubation Plate Layout

| PBS | Mouse serum | Human serum | Cyno serum |
| PBS | Mouse serum | Human serum | Cyno serum |
| PBS | Mouse serum | Human serum | Cyno serum |

3. Seal the plate and incubate at 37° C.
4. Take 20 ul samples at specific intervals (e.g. day 10, day 20) under sterile conditions (BSL-2) to avoid contamination. Freeze at –20° C. until analysis.
5. Analyze the longest incubation first. Dilute samples appropriately and assay for antigen binding to TauC3 by generating ELISA binding curves for each sample (3*dilutions) (section 8.11). Compare the PBS/all serums per mAb sample on the same plate, using non-incubated antibody as control (NI).

All references, publications and patent documents cited herein, as well as text appearing in the figures and sequence listing, are hereby incorporated by reference in their entirety for all purposes to the same extent as if each were so individually denoted.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

What is claimed is:

1. An isolated anti-tauC3 antibody, which has a binding affinity (KD) for TauC3 from $1\times10^{-10}$ to $1\times10^{-12}$ M, and a binding affinity (KD) for a full length tau of from $1\times10^{-4}$ to $1\times10^{-8}$ M, wherein the antibody comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, the variable heavy chain ($V_H$) polypeptide possessing at least 70% sequence identity to SEQ ID NO: 13; and (b) a variable light chain ($V_L$) polypeptide comprising CDR1 represented by SEQ ID NO: 10, CDR2 represented by SEQ ID NO: 11, and CDR3 represented by SEQ ID NO: 12, the variable light chain ($V_L$) polypeptide possessing at least 70% sequence identity to SEQ ID NO: 14, SEQ ID NO: 15, SEQ ID NO: 16, SEQ ID NO: 17, or SEQ ID NO: 18; and is a humanized antibody or a chimeric antibody.

2. The anti-TauC3 antibody of claim 1, wherein the off-rate $K_d$ for TauC3 is from $1\times10^{-4}$ to $1\times10^{-3}$ s$^{-1}$.

3. The anti-TauC3 antibody of claim 1, wherein the variable heavy chain ($V_H$) polypeptide comprises SEQ ID NO: 13; and the variable light chain ($V_L$) polypeptide comprises a sequence selected from the group consisting of SEQ ID NO: 14, SEQ ID NO: 15, SEQ ID NO: 16, SEQ ID NO: 17, and SEQ ID NO: 18.

4. The anti-TauC3 antibody of claim 1, which comprises a $V_L$ chain polypeptide possessing at least 95% sequence identity to SEQ ID NO: 13, and a $V_H$ chain polypeptide possessing at least 95% sequence identity to SEQ ID NO: 14, SEQ ID NO: 15, SEQ ID NO: 16, SEQ ID NO: 17, or SEQ ID NO: 18.

5. The anti-TauC3 antibody of claim 1, which has an aqueous solubility from about 50 mg/ml to about 200 mg/ml.

6. The anti-TauC3 antibody of claim 1, which is a humanized antibody.

7. The anti-TauC3 antibody of claim 1, which is a chimeric antibody.

8. The anti-TauC3 antibody of claim 1, wherein, on the variable heavy chain ($V_H$) polypeptide, CDR1 is a polypeptide of SEQ ID NO: 7, CDR2 is a polypeptide of SEQ ID NO: 8, and CDR3 is a polypeptide of SEQ ID NO: 9; and on the light chain ($V_L$) polypeptide, CDR1 is a polypeptide of SEQ ID NO: 10, CDR2 is a polypeptide of SEQ ID NO: 11, and CDR3 is a polypeptide of SEQ ID NO: 12.

9. The anti-TauC3 antibody of claim 8, wherein the variable heavy chain ($V_H$) polypeptide is a polypeptide of SEQ ID NO: 13 and the variable light chain ($V_L$) polypeptide is a polypeptide of SEQ ID NO: 14, SEQ ID NO: 15, SEQ ID NO: 16, SEQ ID NO: 17, or SEQ ID NO: 18.

10. The anti-TauC3 antibody of claim 1, which is a humanized antibody having a binding affinity (KD) for TauC3 from about 10 pM to about 40 pM.

11. The anti-TauC3 antibody of claim 10, which has a binding affinity (KD) for TauC3 from about 10 to about 35 pM.

12. A pharmaceutical compositions comprising an anti-TauC3 antibody according to claim 1 and one or more pharmaceutically acceptable excipient(s).

13. The pharmaceutical composition of claim 12, wherein the anti-TauC3 comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, and (b) a variable light chain ($V_L$) polypeptide comprising CDR1 represented by Seq. ID No. 10, CDR2 represented by SEQ. ID NO: 11, and CDR3 represented by SEQ ID NO: 12.

14. The pharmaceutical composition of claim 13, wherein the anti-TauC3 antibody has an aqueous solubility of from about 50 mg/ml to about 200 mg/ml.

15. The pharmaceutical composition of claim 13, wherein the anti-TauC3 antibody is a humanized antibody having a binding affinity (KD) for TauC3 from about $1\times10^{-11}$ M to about $4\times10^{-11}$ M.

16. The pharmaceutical composition of claim 13, which has a binding affinity (KD) for TauC3 from about 10 pM to about 40 pM.

17. A method of treating a tauopathy in a subject comprising administering a therapeutically effective amount of an anti-TauC3 antibody to the subject, wherein the anti-TauC3 antibody comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, the variable heavy chain ($V_H$) polypeptide possessing at least 70% sequence identity to SEQ ID NO: 13; and (b) a variable light chain ($V_L$) polypeptide comprising CDR1 represented by SEQ ID NO: 10, CDR2 represented by SEQ ID NO: 11, and CDR3 represented by SEQ ID NO: 12, the variable light chain ($V_L$)

polypeptide possessing at least 70% sequence identity to SEQ ID NO: 14, SEQ ID NO: 15, SEQ ID NO: 16, SEQ ID NO: 17, or SEQ ID NO: 18; and has a binding affinity (KD) for TauC3 from $1\times10^{-10}$ to $1\times10^{-12}$ M; a binding affinity (KD) for a full length tau of from $1\times10^{-4}$ to $1\times10^{-8}$ M; and is a humanized antibody or a chimeric antibody.

18. The method of claim 17, wherein the antibody is a humanized antibody.

19. The method of claim 17, wherein the tauopathy is selected from the group consisting of Alzheimer disease, progressive supranuclear palsy, frontotemporal dementia, traumatic brain injury, Pick's disease, corticobasal degeneration, and frontotemporal lobar degeneration.

20. The method of claim 19, wherein the tauopathy is Alzheimer disease.

* * * * *

SEQUENCE LISTING

<160> NUMBER OF SEQ ID NOS: 153

<210> SEQ ID NO 1
<211> LENGTH: 441
<212> TYPE: PRT
<213> ORGANISM: Artificial Sequence
<220> FEATURE:
<223> OTHER INFORMATION: htau 40

<400> SEQUENCE: 1

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400
```

```
Gly Asp Thr Ser Pro Arg His Leu Ser Asn Val Ser Thr Gly Ser
            405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
            435                 440

<210> SEQ ID NO 2
<211> LENGTH: 410
<212> TYPE: PRT
<213> ORGANISM: Artificial Sequence
<220> FEATURE:
<223> OTHER INFORMATION: Tau 2N3R

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
            85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Leu Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
            165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
            260                 265                 270

Gly Lys Val Gln Ile Val Tyr Lys Pro Val Asp Leu Ser Lys Val Thr
        275                 280                 285

Ser Lys Cys Gly Ser Leu Gly Asn Ile His His Lys Pro Gly Gly Gly
    290                 295                 300

Gln Val Glu Val Lys Ser Glu Lys Leu Asp Phe Lys Asp Arg Val Gln
305                 310                 315                 320
```

-continued

Ser Lys Ile Gly Ser Leu Asp Asn Ile Thr His Val Pro Gly Gly Gly
            325                 330                 335

Asn Lys Lys Ile Glu Thr His Lys Leu Thr Phe Arg Glu Asn Ala Lys
        340                 345                 350

Ala Lys Thr Asp His Gly Ala Glu Ile Val Tyr Lys Ser Pro Val Val
    355                 360                 365

Ser Gly Asp Thr Ser Pro Ala His Leu Ser Asn Val Ser Ser Thr Gly
370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
                405                 410

<210> SEQ ID NO 3
<211> LENGTH: 412
<212> TYPE: PRT
<213> ORGANISM: Artificial Sequence
<220> FEATURE:
<223> OTHER INFORMATION: Tau IN4R

<400> SEQUENCE: 3

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Gly Asp Gly Ser Glu Glu Pro Gly Ser Glu Thr Ser
    50                  55                  60

Asp Ala Lys Ser Thr Pro Thr Ala Glu Ala Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Leu Asp Gly Thr Gly Ser Asp Asp Lys Lys
            100                 105                 110

Ala Lys Gly Ala Asp Gly Lys Thr Leu Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Leu Asp Asn Ile Leu His Val Pro
            260                 265                 270

-continued

```
Gly Gly Gly Ser Val Gln Ile Val Tyr Lys Pro Val Asp Leu Ser Lys
            275                 280                 285
Val Thr Ser Lys Cys Gly Ser Leu Gly Asn Ile His His Lys Pro Gly
    290                 295                 300
Gly Gln Val Glu Val Lys Ser Glu Lys Leu Asp Phe Lys Asp Arg
305                 310                 315                 320
Val Gln Ser Lys Ile Gly Ser Leu Asp Asn Ile Thr His Val Pro Gly
                325                 330                 335
Gly Gly Asn Lys Lys Ile Glu Thr His Lys Leu Thr Phe Arg Glu Asn
            340                 345                 350
Ala Lys Ala Lys Thr Asp His Gly Ala Glu Ile Val Tyr Lys Ser Pro
                355                 360                 365
Val Val Ser Gly Asp Thr Ser Pro Arg His Leu Ser Asn Val Ser Ser
    370                 375                 380
Thr Gly Ser Ile Asp Met Val Asp Ser Pro Gln Leu Ala Thr Leu Ala
385                 390                 395                 400
Asp Glu Val Ser Ala Ser Leu Ala Lys Gln Gly Leu
                405                 410

<210> SEQ ID NO 4
<211> LENGTH: 383
<212> TYPE: PRT
<213> ORGANISM: Artificial Sequence
<220> FEATURE:
<223> OTHER INFORMATION: Tau 0N4R

<400> SEQUENCE: 4

Met Ala Glu Pro Arg Gln Glu Phe Glu Val Met Glu Asp His Ala Gly
1               5                   10                  15
Thr Tyr Gly Leu Gly Asp Arg Leu Asp Gln Gly Gly Tyr Thr Met His
                20                  25                  30
Gln Asp Gln Glu Gly Asp Thr Asp Ala Gly Leu Lys Ala Glu Glu Ala
            35                  40                  45
Gly Ile Gly Asp Thr Pro Ser Leu Glu Asp Glu Ala Ala Gly His Val
    50                  55                  60
Thr Gln Ala Arg Met Val Ser Lys Ser Lys Asp Gly Thr Gly Ser Asp
65                  70                  75                  80
Asp Lys Lys Ala Lys Gly Ala Asp Gly Lys Thr Lys Ile Ala Thr Pro
                85                  90                  95
Arg Gly Ala Ala Pro Pro Gly Gln Lys Gly Gln Ala Asn Ala Thr Arg
                100                 105                 110
Ile Pro Ala Lys Thr Pro Pro Ala Pro Lys Thr Pro Pro Ser Ser Gly
            115                 120                 125
Glu Pro Pro Lys Ser Gly Asp Arg Ser Gly Tyr Ser Ser Pro Gly Ser
    130                 135                 140
Pro Gly Thr Pro Gly Ser Arg Ser Arg Thr Pro Ser Leu Pro Thr Pro
145                 150                 155                 160
Pro Thr Arg Glu Pro Lys Lys Val Ala Val Val Arg Thr Pro Pro Lys
                165                 170                 175
Ser Pro Ser Ser Ala Lys Ser Arg Leu Gln Thr Ala Pro Val Pro Met
                180                 185                 190
Pro Asp Leu Lys Asn Val Lys Ser Leu Ile Gly Ser Thr Glu Asn Leu
            195                 200                 205
Lys His Gln Pro Gly Gly Gly Lys Val Gln Ile Ile Asn Lys Lys Leu
    210                 215                 220
```

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
            245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
            275                 280                 285

Lys Asp Arg Val Gln Ser Lys Ile Gly Ser Leu Asp Asn Ile Thr His
            290                 295                 300

Val Pro Gly Gly Gly Asn Lys Lys Ile Glu Thr His Lys Leu Thr Phe
305                 310                 315                 320

Arg Glu Asn Ala Lys Ala Leu Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
            355                 360                 365

Thr Leu Ala Asp Glu Val Ser Ala Ser Leu Ala Lys Gln Gly Leu
        370                 375                 380

<210> SEQ ID NO 5
<211> LENGTH: 381
<212> TYPE: PRT
<213> ORGANISM: Artificial Sequence
<220> FEATURE:
<223> OTHER INFORMATION: Tau 1N3R

<400> SEQUENCE: 5

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

```
Ser Ala Lys Ser Arg Leu Gln Thr Ala Pro Val Pro Met Pro Asp Leu
        210                 215                 220
Lys Asn Val Lys Ser Lys Ile Gly Ser Thr Glu Asn Leu Lys His Gln
225                 230                 235                 240
Pro Gly Gly Gly Lys Val Gln Ile Val Tyr Lys Pro Val Asp Leu Ser
                245                 250                 255
Lys Val Thr Ser Lys Cys Gly Ser Leu Gly Asn Ile His His Lys Pro
            260                 265                 270
Gly Gly Gly Gln Val Glu Val Lys Ser Glu Lys Leu Asp Phe Lys Asp
        275                 280                 285
Arg Val Gln Ser Lys Ile Gly Ser Leu Asp Asn Ile Thr His Val Pro
    290                 295                 300
Gly Gly Gly Asn Lys Lys Ile Glu Thr His Lys Leu Thr Phe Arg Glu
305                 310                 315                 320
Asn Ala Lys Ala Lys Thr Asp His Gly Ala Glu Ile Val Tyr Lys Ser
                325                 330                 335
Pro Val Val Ser Gly Asp Thr Ser Pro Arg His Leu Ser Asn Val Ser
            340                 345                 350
Ser Thr Gly Ser Ile Asp Met Val Asp Ser Pro Gln Leu Ala Thr Leu
        355                 360                 365
Ala Asp Glu Val Ser Ala Ser Leu Ala Lys Gln Gly Leu
    370                 375                 380

<210> SEQ ID NO 6
<211> LENGTH: 381
<212> TYPE: PRT
<213> ORGANISM: Artificial Sequence
<220> FEATURE:
<223> OTHER INFORMATION: Tau 0N3R

<400> SEQUENCE: 6

Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
            20                  25                  30
Gln Asp Gln Glu Gly Asp Thr Asp Ala Gly Leu Lys Glu Ser Pro Leu
        35                  40                  45
Gln Thr Pro Thr Glu Asp Gly Ser Glu Glu Pro Gly Ser Glu Thr Ser
    50                  55                  60
Asp Ala Lys Ser Thr Pro Thr Ala Glu Ala Glu Glu Ala Gly Ile Gly
65                  70                  75                  80
Asp Thr Pro Ser Leu Glu Asp Glu Ala Ala Gly His Val Thr Gln Ala
                85                  90                  95
Arg Met Val Ser Lys Ser Lys Asp Gly Thr Gly Ser Asp Asp Lys Lys
            100                 105                 110
Ala Lys Gly Ala Asp Gly Lys Thr Lys Ile Ala Thr Pro Arg Gly Ala
        115                 120                 125
Ala Pro Pro Gly Gln Lys Gly Gln Ala Asn Ala Thr Arg Ile Pro Ala
    130                 135                 140
Lys Thr Pro Pro Ala Pro Lys Thr Pro Ser Ser Gly Glu Pro Pro
145                 150                 155                 160
Lys Ser Gly Asp Arg Ser Gly Tyr Ser Ser Pro Gly Ser Pro Gly Thr
                165                 170                 175
Pro Gly Ser Arg Ser Arg Thr Pro Ser Leu Pro Thr Pro Pro Thr Arg
            180                 185                 190
```

Glu Pro Lys Lys Val Ala Val Arg Thr Pro Pro Lys Ser Pro Ser
            195                 200                 205

Ser Ala Lys Ser Arg Leu Gln Thr Ala Pro Val Pro Met Pro Asp Leu
        210                 215                 220

Lys Asn Val Lys Ser Lys Ile Gly Ser Thr Glu Asn Leu Lys His Gln
225                 230                 235                 240

Pro Gly Gly Gly Lys Val Gln Ile Val Tyr Lys Pro Val Asp Leu Ser
                245                 250                 255

Lys Val Thr Ser Lys Cys Gly Ser Leu Gly Asn Ile His His Lys Pro
        260                 265                 270

Gly Gly Gly Gln Val Glu Val Lys Ser Glu Lys Leu Asp Phe Lys Asp
                275                 280                 285

Arg Val Gln Ser Lys Ile Gly Ser Leu Asp Asn Ile Thr His Val Pro
        290                 295                 300

Gly Gly Gly Asn Lys Lys Ile Glu Thr His Lys Leu Thr Phe Arg Glu
305                 310                 315                 320

Asn Ala Lys Ala Lys Thr Asp His Gly Ala Glu Ile Val Tyr Lys Ser
                325                 330                 335

Pro Val Val Ser Gly Asp Thr Ser Pro Arg His Leu Ser Asn Val Ser
        340                 345                 350

Ser Thr Gly Ser Ile Asp Met Val Asp Ser Pro Gln Leu Ala Thr Leu
                355                 360                 365

Ala Asp Glu Val Ser Ala Ser Leu Ala Lys Gln Gly Leu
        370                 375                 380

<210> SEQ ID NO 7
<211> LENGTH: 8
<212> TYPE: PRT
<213> ORGANISM: Artificial Sequence
<220> FEATURE:
<223> OTHER INFORMATION: Heavy Chain CDR1

<400> SEQUENCE: 7

Gly Phe Thr Phe Asn Thr Tyr Ala
1               5

<210> SEQ ID NO 8
<211> LENGTH: 10
<212> TYPE: PRT
<213> ORGANISM: Artificial Sequence
<220> FEATURE:
<223> OTHER INFORMATION: Heavy Chain CDR2

<400> SEQUENCE: 8

Ile Arg Ser Lys Ser Asn Asn Tyr Ala Thr
1               5                   10

<210> SEQ ID NO 9
<211> LENGTH: 6
<212> TYPE: PRT
<213> ORGANISM: Artificial Sequence
<220> FEATURE:
<223> OTHER INFORMATION: VGGGDF

<400> SEQUENCE: 9

Val Gly Gly Gly Asp Phe
1               5

<210> SEQ ID NO 10
<211> LENGTH: 6

```
<212> TYPE: PRT
<213> ORGANISM: Artificial Sequence
<220> FEATURE:
<223> OTHER INFORMATION: Light Chain CDR1

<400> SEQUENCE: 10

Gln Glu Ile Ser Val Tyr
1               5

<210> SEQ ID NO 11
<211> LENGTH: 3
<212> TYPE: PRT
<213> ORGANISM: Artificial Sequence
<220> FEATURE:
<223> OTHER INFORMATION: Light Chain CDR2

<400> SEQUENCE: 11

Gly Ala Phe
1

<210> SEQ ID NO 12
<211> LENGTH: 9
<212> TYPE: PRT
<213> ORGANISM: Artificial Sequence
<220> FEATURE:
<223> OTHER INFORMATION: LQYVRYPWT

<400> SEQUENCE: 12

Leu Gln Tyr Val Arg Tyr Pro Trp Thr
1               5

<210> SEQ ID NO 13
<211> LENGTH: 115
<212> TYPE: PRT
<213> ORGANISM: Artificial Sequence
<220> FEATURE:
<223> OTHER INFORMATION: Heavy Chain HM

<400> SEQUENCE: 13

Leu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Ala Arg Ile Arg Ser Lys Ser Asn Asn Tyr Ala Thr Tyr Tyr Ala Ala
    50                  55                  60

Ser Val Lys Gly Arg Phe Thr Ile Ser Arg Asp Asp Ser Lys Ser Met
65                  70                  75                  80

Ala Tyr Leu Gln Met Asp Ser Leu Lys Thr Glu Asp Thr Ala Val Tyr
                85                  90                  95

Tyr Cys Val Gly Gly Asp Phe Trp Gly Gln Gly Thr Leu Val Thr
            100                 105                 110

Val Ser Ser
        115

<210> SEQ ID NO 14
<211> LENGTH: 107
<212> TYPE: PRT
<213> ORGANISM: Artificial Sequence
<220> FEATURE:
<223> OTHER INFORMATION: light Chain KE

<400> SEQUENCE: 14
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
            20                  25                  30

Leu Gly Trp Phe Gln Lys Pro Gly Lys Ala Pro Lys Arg Leu Ile
        35                  40                  45

Tyr Gly Ala Phe Lys Leu Gln Ser Gly Val Pro Ser Arg Phe Ser Gly
    50                  55                  60

Ser Arg Ser Gly Thr Glu Phe Thr Leu Thr Ile Ser Ser Leu Gln Pro
65              70                  75                  80

Glu Asp Phe Ala Thr Tyr Tyr Cys Leu Gln Tyr Val Arg Tyr Pro Trp
                85                  90                  95

Thr Phe Gly Gly Gly Thr Lys Val Glu Ile Lys
            100                 105

<210> SEQ ID NO 15
<211> LENGTH: 107
<212> TYPE: PRT
<213> ORGANISM: Artificial Sequence
<220> FEATURE:
<223> OTHER INFORMATION: light Chain KN

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
            20                  25                  30

Leu Gly Trp Tyr Gln Gln Lys Pro Gly Lys Ala Pro Lys Arg Leu Ile
        35                  40                  45

Tyr Gly Ala Phe Thr Leu Gln Ser Gly Val Pro Ser Arg Phe Ser Gly
    50                  55                  60

Ser Arg Ser Gly Thr Glu Tyr Thr Leu Thr Ile Ser Ser Leu Gln Pro
65              70                  75                  80

Glu Asp Phe Ala Thr Tyr Tyr Cys Leu Gln Tyr Val Arg Tyr Pro Trp
                85                  90                  95

Thr Phe Gly Gly Gly Thr Lys Val Glu Ile Lys
            100                 105

<210> SEQ ID NO 16
<211> LENGTH: 107
<212> TYPE: PRT
<213> ORGANISM: Artificial Sequence
<220> FEATURE:
<223> OTHER INFORMATION: light Chain KO

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
            20                  25                  30

Leu Gly Trp Tyr Gln Gln Lys Pro Gly Lys Ala Pro Lys Arg Leu Ile
        35                  40                  45

Tyr Gly Ala Phe Ser Leu Gln Ser Gly Val Pro Ser Arg Phe Ser Gly
    50                  55                  60

Ser Arg Ser Gly Thr Glu Tyr Thr Leu Thr Ile Ser Ser Leu Gln Pro
65              70                  75                  80

Glu Asp Phe Ala Thr Tyr Tyr Cys Leu Gln Tyr Val Arg Tyr Pro Trp

```
                        85                  90                  95

Thr Phe Gly Gly Gly Thr Lys Val Glu Ile Lys
                100                 105

<210> SEQ ID NO 17
<211> LENGTH: 107
<212> TYPE: PRT
<213> ORGANISM: Artificial Sequence
<220> FEATURE:
<223> OTHER INFORMATION: light Chain KP

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
            20                  25                  30

Leu Gly Trp Phe Gln Gln Lys Pro Gly Lys Ala Pro Lys Arg Leu Ile
        35                  40                  45

Tyr Gly Ala Phe Lys Leu Gln Ser Gly Val Pro Ser Arg Phe Ser Gly
    50                  55                  60

Ser Arg Ser Gly Thr Glu Tyr Thr Leu Thr Ile Ser Ser Leu Gln Pro
65                  70                  75                  80

Glu Asp Phe Ala Thr Tyr Tyr Cys Leu Gln Tyr Val Arg Tyr Pro Trp
                85                  90                  95

Thr Phe Gly Gly Gly Thr Lys Val Glu Ile Lys
                100                 105

<210> SEQ ID NO 18
<211> LENGTH: 107
<212> TYPE: PRT
<213> ORGANISM: Artificial Sequence
<220> FEATURE:
<223> OTHER INFORMATION: light Chain KM

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
            20                  25                  30

Leu Ser Trp Phe Gln Gln Lys Pro Gly Lys Ala Ile Lys Arg Leu Ile
        35                  40                  45

Tyr Gly Ala Phe Ser Leu Gln Ser Gly Val Pro Ser Arg Phe Ser Gly
    50                  55                  60

Ser Arg Ser Gly Thr Glu Tyr Thr Leu Thr Ile Ser Ser Leu Gln Pro
65                  70                  75                  80

Glu Asp Phe Ala Thr Tyr Tyr Cys Leu Gln Tyr Val Arg Tyr Pro Trp
                85                  90                  95

Thr Phe Gly Gly Gly Thr Lys Val Glu Ile Lys
                100                 105

<210> SEQ ID NO 19
<211> LENGTH: 10
<212> TYPE: PRT
<213> ORGANISM: Artificial Sequence
<220> FEATURE:
<223> OTHER INFORMATION: immunizing peptide

<400> SEQUENCE: 19

Ser Ser Thr Gly Ser Ile Asp Met Val Asp
1               5                   10
```

<210> SEQ ID NO 20
<211> LENGTH: 48
<212> TYPE: DNA
<213> ORGANISM: Artificial Sequence
<220> FEATURE:
<223> OTHER INFORMATION: primer

<400> SEQUENCE: 20
tgtaaaacga cggccagtat gaagttgcct gttaggctgt tggtgctg        48

<210> SEQ ID NO 21
<211> LENGTH: 48
<212> TYPE: DNA
<213> ORGANISM: Artificial Sequence
<220> FEATURE:
<223> OTHER INFORMATION: primer

<400> SEQUENCE: 21
tgtaaaacga cggccagtat ggagwcagac acactcctgy tatgggtg        48

<210> SEQ ID NO 22
<211> LENGTH: 48
<212> TYPE: DNA
<213> ORGANISM: Artificial Sequence
<220> FEATURE:
<223> OTHER INFORMATION: primer

<400> SEQUENCE: 22
tgtaaaacga cggccagtat gagtgtgctc actcaggtcc tggsgttg        48

<210> SEQ ID NO 23
<211> LENGTH: 51
<212> TYPE: DNA
<213> ORGANISM: Artificial Sequence
<220> FEATURE:
<223> OTHER INFORMATION: primer

<400> SEQUENCE: 23
tgtaaaacga cggccagtat gaggrcccct gctcagwtty ttggmwtctt g        51

<210> SEQ ID NO 24
<211> LENGTH: 47
<212> TYPE: DNA
<213> ORGANISM: Artificial Sequence
<220> FEATURE:
<223> OTHER INFORMATION: primer

<400> SEQUENCE: 24
tgtaaaacga cggccagtat ggatttwagg tgcagattwt cagcttc        47

<210> SEQ ID NO 25
<211> LENGTH: 45
<212> TYPE: DNA
<213> ORGANISM: Artificial Sequence
<220> FEATURE:
<223> OTHER INFORMATION: primer

<400> SEQUENCE: 25
tgtaaaacga cggccagtat gaggtkckkt gktsagstsc tgrgg        45

<210> SEQ ID NO 26
<211> LENGTH: 49
<212> TYPE: DNA
<213> ORGANISM: Artificial Sequence
<220> FEATURE:

<223> OTHER INFORMATION: primer

<400> SEQUENCE: 26
tgtaaaacga cggccagtat gggcwtcaag atggagtcac akwyycwgg         49

<210> SEQ ID NO 27
<211> LENGTH: 49
<212> TYPE: DNA
<213> ORGANISM: Artificial Sequence
<220> FEATURE:
<223> OTHER INFORMATION: primer

<400> SEQUENCE: 27
tgtaaaacga cggccagtat gtggggayct ktttycmmtt tttcaattg         49

<210> SEQ ID NO 28
<211> LENGTH: 43
<212> TYPE: DNA
<213> ORGANISM: Artificial Sequence
<220> FEATURE:
<223> OTHER INFORMATION: primer

<400> SEQUENCE: 28
tgtaaaacga cggccagtat ggtrtccwca sctcagttcc ttg               43

<210> SEQ ID NO 29
<211> LENGTH: 45
<212> TYPE: DNA
<213> ORGANISM: Artificial Sequence
<220> FEATURE:
<223> OTHER INFORMATION: primer

<400> SEQUENCE: 29
tgtaaaacga cggccagtat gtatatatgt ttgttgtcta tttct             45

<210> SEQ ID NO 30
<211> LENGTH: 46
<212> TYPE: DNA
<213> ORGANISM: Artificial Sequence
<220> FEATURE:
<223> OTHER INFORMATION: primer

<400> SEQUENCE: 30
tgtaaaacga cggccagtat ggaagcccca gctcagcttc tcttcc            46

<210> SEQ ID NO 31
<211> LENGTH: 44
<212> TYPE: DNA
<213> ORGANISM: Artificial Sequence
<220> FEATURE:
<223> OTHER INFORMATION: primer

<400> SEQUENCE: 31
tgtaaaacga cggccagtat gragtywcag acccaggtct tyrt              44

<210> SEQ ID NO 32
<211> LENGTH: 44
<212> TYPE: DNA
<213> ORGANISM: Artificial Sequence
<220> FEATURE:
<223> OTHER INFORMATION: primer

<400> SEQUENCE: 32
tgtaaaacga cggccagtat ggagacacat tctcaggtct ttgt              44

<210> SEQ ID NO 33
<211> LENGTH: 44
<212> TYPE: DNA
<213> ORGANISM: Artificial Sequence
<220> FEATURE:
<223> OTHER INFORMATION: primer

<400> SEQUENCE: 33
tgtaaaacga cggccagtat ggattcacag gcccaggttc ttat                    44

<210> SEQ ID NO 34
<211> LENGTH: 44
<212> TYPE: DNA
<213> ORGANISM: Artificial Sequence
<220> FEATURE:
<223> OTHER INFORMATION: primer

<400> SEQUENCE: 34
tgtaaaacga cggccagtat gatgagtcct gcccagttcc tgtt                    44

<210> SEQ ID NO 35
<211> LENGTH: 47
<212> TYPE: DNA
<213> ORGANISM: Artificial Sequence
<220> FEATURE:
<223> OTHER INFORMATION: primer

<400> SEQUENCE: 35
tgtaaaacga cggccagtat gaatttgcct gttcatctct tggtgct                 47

<210> SEQ ID NO 36
<211> LENGTH: 47
<212> TYPE: DNA
<213> ORGANISM: Artificial Sequence
<220> FEATURE:
<223> OTHER INFORMATION: primer

<400> SEQUENCE: 36
tgtaaaacga cggccagtat ggattttcaa ttggtcctca tctcctt                 47

<210> SEQ ID NO 37
<211> LENGTH: 44
<212> TYPE: DNA
<213> ORGANISM: Artificial Sequence
<220> FEATURE:
<223> OTHER INFORMATION: primer

<400> SEQUENCE: 37
tgtaaaacga cggccagtat gaggtgccta rctsagttcc tgrg                    44

<210> SEQ ID NO 38
<211> LENGTH: 44
<212> TYPE: DNA
<213> ORGANISM: Artificial Sequence
<220> FEATURE:
<223> OTHER INFORMATION: primer

<400> SEQUENCE: 38
tgtaaaacga cggccagtat gaagtactct gctcagtttc tagg                    44

<210> SEQ ID NO 39
<211> LENGTH: 44
<212> TYPE: DNA
<213> ORGANISM: Artificial Sequence
<220> FEATURE:
<223> OTHER INFORMATION: primer

<400> SEQUENCE: 39
tgtaaaacga cggccagtat gaggcattct cttcaattct tggg                44

<210> SEQ ID NO 40
<211> LENGTH: 38
<212> TYPE: DNA
<213> ORGANISM: Artificial Sequence
<220> FEATURE:
<223> OTHER INFORMATION: primer

<400> SEQUENCE: 40
caggaaacag ctatgaccac tggatggtgg gaagatgg                       38

<210> SEQ ID NO 41
<211> LENGTH: 45
<212> TYPE: DNA
<213> ORGANISM: Artificial Sequence
<220> FEATURE:
<223> OTHER INFORMATION: primer

<400> SEQUENCE: 41
tgtaaaacga cggccagtat gaaatgcagc tggggcatst tcttc               45

<210> SEQ ID NO 42
<211> LENGTH: 44
<212> TYPE: DNA
<213> ORGANISM: Artificial Sequence
<220> FEATURE:
<223> OTHER INFORMATION: primer

<400> SEQUENCE: 42
tgtaaaacga cggccagtat gggatggagc trtatcatsy tctt                44

<210> SEQ ID NO 43
<211> LENGTH: 45
<212> TYPE: DNA
<213> ORGANISM: Artificial Sequence
<220> FEATURE:
<223> OTHER INFORMATION: primer

<400> SEQUENCE: 43
tgtaaaacga cggccagtat gaagwtgtgg ttaaactggg ttttt               45

<210> SEQ ID NO 44
<211> LENGTH: 43
<212> TYPE: DNA
<213> ORGANISM: Artificial Sequence
<220> FEATURE:
<223> OTHER INFORMATION: primer

<400> SEQUENCE: 44
tgtaaaacga cggccagtat gractttggg ytcagcttgr ttt                 43

<210> SEQ ID NO 45
<211> LENGTH: 48
<212> TYPE: DNA
<213> ORGANISM: Artificial Sequence
<220> FEATURE:
<223> OTHER INFORMATION: primer

<400> SEQUENCE: 45
tgtaaaacga cggccagtat ggactccagg ctcaatttag ttttcctt            48

<210> SEQ ID NO 46
<211> LENGTH: 45

<212> TYPE: DNA
<213> ORGANISM: Artificial Sequence
<220> FEATURE:
<223> OTHER INFORMATION: primer

<400> SEQUENCE: 46
tgtaaaacga cggccagtat ggctgtcytr gsgctrctct tctgc                45

<210> SEQ ID NO 47
<211> LENGTH: 44
<212> TYPE: DNA
<213> ORGANISM: Artificial Sequence
<220> FEATURE:
<223> OTHER INFORMATION: primer

<400> SEQUENCE: 47
tgtaaaacga cggccagtat ggratggagc kggrtctttm tctt                 44

<210> SEQ ID NO 48
<211> LENGTH: 41
<212> TYPE: DNA
<213> ORGANISM: Artificial Sequence
<220> FEATURE:
<223> OTHER INFORMATION: primer

<400> SEQUENCE: 48
tgtaaaacga cggccagtat gagagtgctg attcttttgt g                    41

<210> SEQ ID NO 49
<211> LENGTH: 48
<212> TYPE: DNA
<213> ORGANISM: Artificial Sequence
<220> FEATURE:
<223> OTHER INFORMATION: primer

<400> SEQUENCE: 49
tgtaaaacga cggccagtat ggmttgggtg tggamcttgc tattcctg             48

<210> SEQ ID NO 50
<211> LENGTH: 45
<212> TYPE: DNA
<213> ORGANISM: Artificial Sequence
<220> FEATURE:
<223> OTHER INFORMATION: primer

<400> SEQUENCE: 50
tgtaaaacga cggccagtat gggcagactt acattctcat tcctg                45

<210> SEQ ID NO 51
<211> LENGTH: 46
<212> TYPE: DNA
<213> ORGANISM: Artificial Sequence
<220> FEATURE:
<223> OTHER INFORMATION: primer

<400> SEQUENCE: 51
tgtaaaacga cggccagtat ggattttggg ctgatttttt ttattg               46

<210> SEQ ID NO 52
<211> LENGTH: 45
<212> TYPE: DNA
<213> ORGANISM: Artificial Sequence
<220> FEATURE:
<223> OTHER INFORMATION: primer

<400> SEQUENCE: 52

```
tgtaaaacga cggccagtat gatggtgtta agtcttctgt acctg          45

<210> SEQ ID NO 53
<211> LENGTH: 49
<212> TYPE: DNA
<213> ORGANISM: Artificial Sequence
<220> FEATURE:
<223> OTHER INFORMATION: primer

<400> SEQUENCE: 53
tgtaaaacga cggccagtat gaacaggctt acttcctcat tgctgctgc      49

<210> SEQ ID NO 54
<211> LENGTH: 39
<212> TYPE: DNA
<213> ORGANISM: Artificial Sequence
<220> FEATURE:
<223> OTHER INFORMATION: primer

<400> SEQUENCE: 54
caggaaacag ctatgaccca gtggatagac agatggggg                 39

<210> SEQ ID NO 55
<211> LENGTH: 39
<212> TYPE: DNA
<213> ORGANISM: Artificial Sequence
<220> FEATURE:
<223> OTHER INFORMATION: primer

<400> SEQUENCE: 55
caggaaacag ctatgaccca gtggatagac cgatggggc                 39

<210> SEQ ID NO 56
<211> LENGTH: 39
<212> TYPE: DNA
<213> ORGANISM: Artificial Sequence
<220> FEATURE:
<223> OTHER INFORMATION: primer

<400> SEQUENCE: 56
caggaaacag ctatgaccca gtggatagac tgatggggg                 39

<210> SEQ ID NO 57
<211> LENGTH: 39
<212> TYPE: DNA
<213> ORGANISM: Artificial Sequence
<220> FEATURE:
<223> OTHER INFORMATION: primer

<400> SEQUENCE: 57
caggaaacag ctatgaccca agggatagac agatggggc                 39

<210> SEQ ID NO 58
<211> LENGTH: 41
<212> TYPE: DNA
<213> ORGANISM: Artificial Sequence
<220> FEATURE:
<223> OTHER INFORMATION: primer

<400> SEQUENCE: 58
tgtaaaacga cggccagtga ggtgcaggtt gttgagtctg g              41

<210> SEQ ID NO 59
<211> LENGTH: 20
<212> TYPE: DNA
<213> ORGANISM: Artificial Sequence
```

-continued

```
<220> FEATURE:
<223> OTHER INFORMATION: primer

<400> SEQUENCE: 59
tgttcctttc catgggtctt                                                    20

<210> SEQ ID NO 60
<211> LENGTH: 21
<212> TYPE: DNA
<213> ORGANISM: Artificial Sequence
<220> FEATURE:
<223> OTHER INFORMATION: primer

<400> SEQUENCE: 60
ctctcggagg tgctcctgga g                                                  21

<210> SEQ ID NO 61
<211> LENGTH: 20
<212> TYPE: DNA
<213> ORGANISM: Artificial Sequence
<220> FEATURE:
<223> OTHER INFORMATION: primer

<400> SEQUENCE: 61
gcagttccag atttcaactg                                                    20

<210> SEQ ID NO 62
<211> LENGTH: 18
<212> TYPE: DNA
<213> ORGANISM: Artificial Sequence
<220> FEATURE:
<223> OTHER INFORMATION: primer

<400> SEQUENCE: 62
tgtaaaacga cggccagt                                                      18

<210> SEQ ID NO 63
<211> LENGTH: 18
<212> TYPE: DNA
<213> ORGANISM: Artificial Sequence
<220> FEATURE:
<223> OTHER INFORMATION: primer

<400> SEQUENCE: 63
caggaaacag ctatgacc                                                      18

<210> SEQ ID NO 64
<211> LENGTH: 45
<212> TYPE: DNA
<213> ORGANISM: Artificial Sequence
<220> FEATURE:
<223> OTHER INFORMATION: primer

<400> SEQUENCE: 64
ctctggctcc ctgataccac cggagaggtg caggtggtgg agagc                        45

<210> SEQ ID NO 65
<211> LENGTH: 45
<212> TYPE: DNA
<213> ORGANISM: Artificial Sequence
<220> FEATURE:
<223> OTHER INFORMATION: primer

<400> SEQUENCE: 65
ctctggctcc ctgataccac cggagatatc cagatgacac agtct                        45
```

<210> SEQ ID NO 66
<211> LENGTH: 38
<212> TYPE: DNA
<213> ORGANISM: Artificial Sequence
<220> FEATURE:
<223> OTHER INFORMATION: primer

<400> SEQUENCE: 66
gggcccttgg tggaggcgga gctcactgtc agggcggt          38

<210> SEQ ID NO 67
<211> LENGTH: 44
<212> TYPE: DNA
<213> ORGANISM: Artificial Sequence
<220> FEATURE:
<223> OTHER INFORMATION: primer

<400> SEQUENCE: 67
cgcttggtgc tgccacagtt ctcttgatct ccagctttgt gccg          44

<210> SEQ ID NO 68
<211> LENGTH: 46
<212> TYPE: DNA
<213> ORGANISM: Artificial Sequence
<220> FEATURE:
<223> OTHER INFORMATION: primer

<400> SEQUENCE: 68
ctctggctcc ctgataccac cggactggtg cagctggtgg aaagcg          46

<210> SEQ ID NO 69
<211> LENGTH: 46
<212> TYPE: DNA
<213> ORGANISM: Artificial Sequence
<220> FEATURE:
<223> OTHER INFORMATION: primer

<400> SEQUENCE: 69
ctctggctcc ctgataccac cggagaggtg caggtggtgg aaagcg          46

<210> SEQ ID NO 70
<211> LENGTH: 39
<212> TYPE: DNA
<213> ORGANISM: Artificial Sequence
<220> FEATURE:
<223> OTHER INFORMATION: primer

<400> SEQUENCE: 70
gggcccttgg tggaggcgga gctcactgtc accagggtg          39

<210> SEQ ID NO 71
<211> LENGTH: 30
<212> TYPE: DNA
<213> ORGANISM: Artificial Sequence
<220> FEATURE:
<223> OTHER INFORMATION: primer

<400> SEQUENCE: 71
cctgatacca ccggagaggt gcagctggtg          30

<210> SEQ ID NO 72
<211> LENGTH: 30
<212> TYPE: DNA
<213> ORGANISM: Artificial Sequence
<220> FEATURE:
<223> OTHER INFORMATION: primer

<400> SEQUENCE: 72
caccagctgc acctctccgg tggtatcagg                                        30

<210> SEQ ID NO 73
<211> LENGTH: 27
<212> TYPE: DNA
<213> ORGANISM: Artificial Sequence
<220> FEATURE:
<223> OTHER INFORMATION: primer

<400> SEQUENCE: 73
cggactggtg caggtggtgg aaagcgg                                           27

<210> SEQ ID NO 74
<211> LENGTH: 27
<212> TYPE: DNA
<213> ORGANISM: Artificial Sequence
<220> FEATURE:
<223> OTHER INFORMATION: primer

<400> SEQUENCE: 74
ccgctttcca ccacctgcac cagtccg                                           27

<210> SEQ ID NO 75
<211> LENGTH: 34
<212> TYPE: DNA
<213> ORGANISM: Artificial Sequence
<220> FEATURE:
<223> OTHER INFORMATION: primer

<400> SEQUENCE: 75
tttaacacat atgcaatgaa ctgggtgcgg cagg                                   34

<210> SEQ ID NO 76
<211> LENGTH: 34
<212> TYPE: DNA
<213> ORGANISM: Artificial Sequence
<220> FEATURE:
<223> OTHER INFORMATION: primer

<400> SEQUENCE: 76
cctgccgcac ccagttcatt gcatatgtgt taaa                                   34

<210> SEQ ID NO 77
<211> LENGTH: 27
<212> TYPE: DNA
<213> ORGANISM: Artificial Sequence
<220> FEATURE:
<223> OTHER INFORMATION: primer

<400> SEQUENCE: 77
ctggagtggg tggcccggat cagatct                                           27

<210> SEQ ID NO 78
<211> LENGTH: 27
<212> TYPE: DNA
<213> ORGANISM: Artificial Sequence
<220> FEATURE:
<223> OTHER INFORMATION: primer

<400> SEQUENCE: 78
agatctgatc cgggccaccc actccag                                           27

<210> SEQ ID NO 79

```
<211> LENGTH: 49
<212> TYPE: DNA
<213> ORGANISM: Artificial Sequence
<220> FEATURE:
<223> OTHER INFORMATION: primer

<400> SEQUENCE: 79
ctaagagcaa caattatgca acatattatg cagcatctgt gaagggcag          49

<210> SEQ ID NO 80
<211> LENGTH: 49
<212> TYPE: DNA
<213> ORGANISM: Artificial Sequence
<220> FEATURE:
<223> OTHER INFORMATION: primer

<400> SEQUENCE: 80
ctgcccttca cagatgctgc ataatatgtt gcataattgt tgctcttag          49

<210> SEQ ID NO 81
<211> LENGTH: 40
<212> TYPE: DNA
<213> ORGANISM: Artificial Sequence
<220> FEATURE:
<223> OTHER INFORMATION: primer

<400> SEQUENCE: 81
tatgcaacag catatgcaga ttctgtgaag ggcaggttca                    40

<210> SEQ ID NO 82
<211> LENGTH: 40
<212> TYPE: DNA
<213> ORGANISM: Artificial Sequence
<220> FEATURE:
<223> OTHER INFORMATION: primer

<400> SEQUENCE: 82
tgaacctgcc cttcacagaa tctgcatatg ctgttgcata                    40

<210> SEQ ID NO 83
<211> LENGTH: 35
<212> TYPE: DNA
<213> ORGANISM: Artificial Sequence
<220> FEATURE:
<223> OTHER INFORMATION: primer

<400> SEQUENCE: 83
ccgcgacgat tctaagagta cagcctatct gcaga                         35

<210> SEQ ID NO 84
<211> LENGTH: 35
<212> TYPE: DNA
<213> ORGANISM: Artificial Sequence
<220> FEATURE:
<223> OTHER INFORMATION: primer

<400> SEQUENCE: 84
tctgcagata ggctgtactc ttagaatcgt cgcgg                         35

<210> SEQ ID NO 85
<211> LENGTH: 40
<212> TYPE: DNA
<213> ORGANISM: Artificial Sequence
<220> FEATURE:
<223> OTHER INFORMATION: primer

<400> SEQUENCE: 85
```

-continued tctcccgcga cgattctaag aatatggcct atctgcagat 40

<210> SEQ ID NO 86
<211> LENGTH: 40
<212> TYPE: DNA
<213> ORGANISM: Artificial Sequence
<220> FEATURE:
<223> OTHER INFORMATION: primer

<400> SEQUENCE: 86
atctgcagat aggccatatt cttagaatcg tcgcgggaga 40

<210> SEQ ID NO 87
<211> LENGTH: 39
<212> TYPE: DNA
<213> ORGANISM: Artificial Sequence
<220> FEATURE:
<223> OTHER INFORMATION: primer

<400> SEQUENCE: 87
gacgattcta agaatacagt ctatctgcag atggactcc 39

<210> SEQ ID NO 88
<211> LENGTH: 39
<212> TYPE: DNA
<213> ORGANISM: Artificial Sequence
<220> FEATURE:
<223> OTHER INFORMATION: primer

<400> SEQUENCE: 88
ggagtccatc tgcagataga ctgtattctt agaatcgtc 39

<210> SEQ ID NO 89
<211> LENGTH: 46
<212> TYPE: DNA
<213> ORGANISM: Artificial Sequence
<220> FEATURE:
<223> OTHER INFORMATION: primer

<400> SEQUENCE: 89
ctctggctcc ctgataccac cggagacatc cagatgaccc agtctc 46

<210> SEQ ID NO 90
<211> LENGTH: 46
<212> TYPE: DNA
<213> ORGANISM: Artificial Sequence
<220> FEATURE:
<223> OTHER INFORMATION: primer

<400> SEQUENCE: 90
ctctggctcc ctgataccac cggagacatc cagatgacac agtctc 46

<210> SEQ ID NO 91
<211> LENGTH: 44
<212> TYPE: DNA
<213> ORGANISM: Artificial Sequence
<220> FEATURE:
<223> OTHER INFORMATION: primer

<400> SEQUENCE: 91
cgcttggtgc tgccacagtt ctcttgatct ccacctttgt gccg 44

<210> SEQ ID NO 92
<211> LENGTH: 33
<212> TYPE: DNA

```
<213> ORGANISM: Artificial Sequence
<220> FEATURE:
<223> OTHER INFORMATION: primer

<400> SEQUENCE: 92
ttctgctgat accagctcag gtacacggag atc                                33

<210> SEQ ID NO 93
<211> LENGTH: 29
<212> TYPE: DNA
<213> ORGANISM: Artificial Sequence
<220> FEATURE:
<223> OTHER INFORMATION: primer

<400> SEQUENCE: 93
tgtacctggg ctggtttcag cagaagccc                                     29

<210> SEQ ID NO 94
<211> LENGTH: 29
<212> TYPE: DNA
<213> ORGANISM: Artificial Sequence
<220> FEATURE:
<223> OTHER INFORMATION: primer

<400> SEQUENCE: 94
gggcttctgc tgaaaccagc ccaggtaca                                     29

<210> SEQ ID NO 95
<211> LENGTH: 34
<212> TYPE: DNA
<213> ORGANISM: Artificial Sequence
<220> FEATURE:
<223> OTHER INFORMATION: primer

<400> SEQUENCE: 95
gaagcccggc aaggccatta agcggctgat ctac                               34

<210> SEQ ID NO 96
<211> LENGTH: 34
<212> TYPE: DNA
<213> ORGANISM: Artificial Sequence
<220> FEATURE:
<223> OTHER INFORMATION: primer

<400> SEQUENCE: 96
gtagatcagc cgcttaatgg ccttgccggg cttc                               34

<210> SEQ ID NO 97
<211> LENGTH: 28
<212> TYPE: DNA
<213> ORGANISM: Artificial Sequence
<220> FEATURE:
<223> OTHER INFORMATION: primer

<400> SEQUENCE: 97
atctacggcg ccttcacgct gcagtccg                                      28

<210> SEQ ID NO 98
<211> LENGTH: 28
<212> TYPE: DNA
<213> ORGANISM: Artificial Sequence
<220> FEATURE:
<223> OTHER INFORMATION: primer

<400> SEQUENCE: 98
cggactgcag cgtgaaggcg ccgtagat                                      28
```

<210> SEQ ID NO 99
<211> LENGTH: 31
<212> TYPE: DNA
<213> ORGANISM: Artificial Sequence
<220> FEATURE:
<223> OTHER INFORMATION: primer

<400> SEQUENCE: 99
ggatccagat ctggcagcga gtttaccctg a                          31

<210> SEQ ID NO 100
<211> LENGTH: 31
<212> TYPE: DNA
<213> ORGANISM: Artificial Sequence
<220> FEATURE:
<223> OTHER INFORMATION: primer

<400> SEQUENCE: 100
tcagggtaaa ctcgctgcca gatctggatc c                          31

<210> SEQ ID NO 101
<211> LENGTH: 35
<212> TYPE: DNA
<213> ORGANISM: Artificial Sequence
<220> FEATURE:
<223> OTHER INFORMATION: primer

<400> SEQUENCE: 101
cagatctggc accgagtata ccctgacaat ctcta                      35

<210> SEQ ID NO 102
<211> LENGTH: 35
<212> TYPE: DNA
<213> ORGANISM: Artificial Sequence
<220> FEATURE:
<223> OTHER INFORMATION: primer

<400> SEQUENCE: 102
tagagattgt cagggtatac tcggtgccag atctg                      35

<210> SEQ ID NO 103
<211> LENGTH: 30
<212> TYPE: DNA
<213> ORGANISM: Artificial Sequence
<220> FEATURE:
<223> OTHER INFORMATION: primer

<400> SEQUENCE: 103
ctacggcgcc ttcagcctgc agtccggagt                            30

<210> SEQ ID NO 104
<211> LENGTH: 30
<212> TYPE: DNA
<213> ORGANISM: Artificial Sequence
<220> FEATURE:
<223> OTHER INFORMATION: primer

<400> SEQUENCE: 104
actccggact gcaggctgaa ggcgccgtag                            30

<210> SEQ ID NO 105
<211> LENGTH: 115
<212> TYPE: PRT
<213> ORGANISM: Artificial Sequence
<220> FEATURE:

<223> OTHER INFORMATION: heavy chain

<400> SEQUENCE: 105

Glu Val Gln Val Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Val Tyr Leu Gln Met Asn Asn Leu Lys Thr Glu Asp Thr Ala Met Tyr
                85                  90                  95

Tyr Cys Val Gly Gly Gly Asp Phe Trp Gly Gln Gly Thr Ala Leu Thr
            100                 105                 110

Val Ser Ser
        115

<210> SEQ ID NO 106
<211> LENGTH: 114
<212> TYPE: PRT
<213> ORGANISM: Artificial Sequence
<220> FEATURE:
<223> OTHER INFORMATION: heavy chain

<400> SEQUENCE: 106

Leu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asp Ser Leu Lys Thr Glu Asp Thr Ala Val Tyr
                85                  90                  95

Tyr Cys Thr Thr Tyr Glu Gly Trp Gly Gln Gly Thr Leu Val Thr Val
            100                 105                 110

Ser Ser

<210> SEQ ID NO 107
<211> LENGTH: 115
<212> TYPE: PRT
<213> ORGANISM: Artificial Sequence
<220> FEATURE:
<223> OTHER INFORMATION: heavy chain

<400> SEQUENCE: 107

Leu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met His Trp Val Arg Gln Ala Ser Gly Lys Gly Leu Glu Trp Val
        35                  40                  45

```
Gly Arg Ile Arg Ser Lys Ser Asn Asn Tyr Ala Thr Ala Tyr Ala Ala
        50                  55                  60

Ser Val Lys Gly Arg Phe Thr Ile Ser Arg Asp Asp Ser Lys Asn Thr
 65                  70                  75                  80

Ala Tyr Leu Gln Met Asp Ser Leu Lys Thr Glu Asp Thr Ala Val Tyr
                    85                  90                  95

Tyr Cys Val Gly Gly Asp Phe Trp Gly Gln Gly Thr Leu Val Thr
                100                 105                 110

Val Ser Ser
        115

<210> SEQ ID NO 108
<211> LENGTH: 115
<212> TYPE: PRT
<213> ORGANISM: Artificial Sequence
<220> FEATURE:
<223> OTHER INFORMATION: heavy chain

<400> SEQUENCE: 108

Glu Val Gln Val Val Glu Ser Gly Gly Gly Leu Val Gln Pro Gly Gly
 1               5                  10                  15

Ser Leu Lys Leu Ser Cys Ala Ala Ser Gly Phe Thr Phe Asn Thr Tyr
                20                  25                  30

Ala Met Asn Trp Val Arg Gln Ala Ser Gly Lys Gly Leu Glu Trp Val
                35                  40                  45

Ala Arg Ile Arg Ser Lys Ser Asn Asn Tyr Ala Thr Tyr Tyr Ala Asp
        50                  55                  60

Ser Val Lys Gly Arg Phe Thr Ile Ser Arg Asp Asp Ser Lys Ser Met
 65                  70                  75                  80

Val Tyr Leu Gln Met Asp Ser Leu Lys Thr Glu Asp Thr Ala Val Tyr
                    85                  90                  95

Tyr Cys Val Gly Gly Asp Phe Trp Gly Gln Gly Thr Leu Val Thr
                100                 105                 110

Val Ser Ser
        115

<210> SEQ ID NO 109
<211> LENGTH: 115
<212> TYPE: PRT
<213> ORGANISM: Artificial Sequence
<220> FEATURE:
<223> OTHER INFORMATION: heavy chain

<400> SEQUENCE: 109

Leu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Asn Thr Tyr
                20                  25                  30

Ala Met Asn Trp Val Arg Gln Ala Ser Gly Lys Gly Leu Glu Trp Val
                35                  40                  45

Gly Arg Ile Arg Ser Lys Ser Asn Asn Tyr Ala Thr Tyr Tyr Ala Ala
        50                  55                  60

Ser Val Lys Gly Arg Phe Thr Ile Ser Arg Asp Asp Ser Lys Ser Met
 65                  70                  75                  80

Ala Tyr Leu Gln Met Asp Ser Leu Lys Thr Glu Asp Thr Ala Val Tyr
                    85                  90                  95

Tyr Cys Val Gly Gly Gly Asp Phe Trp Gly Gln Gly Thr Leu Val Thr
```

```
                  100                 105                 110

Val Ser Ser
        115

<210> SEQ ID NO 110
<211> LENGTH: 115
<212> TYPE: PRT
<213> ORGANISM: Artificial Sequence
<220> FEATURE:
<223> OTHER INFORMATION: heavy chain

<400> SEQUENCE: 110

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met His Trp Val Arg Gln Ala Ser Gly Lys Gly Leu Glu Trp Val
        35                  40                  45

Gly Arg Ile Arg Ser Lys Ser Asn Asn Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asp Ser Leu Lys Thr Glu Asp Thr Ala Val Tyr
                85                  90                  95

Tyr Cys Val Gly Gly Gly Asp Phe Trp Gly Gln Gly Thr Leu Val Thr
            100                 105                 110

Val Ser Ser
        115

<210> SEQ ID NO 111
<211> LENGTH: 115
<212> TYPE: PRT
<213> ORGANISM: Artificial Sequence
<220> FEATURE:
<223> OTHER INFORMATION: heavy chain

<400> SEQUENCE: 111

Leu Val Gln Val Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met His Trp Val Arg Gln Ala Ser Gly Lys Gly Leu Glu Trp Val
        35                  40                  45

Gly Arg Ile Arg Ser Lys Ser Asn Asn Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asp Ser Leu Lys Thr Glu Asp Thr Ala Val Tyr
                85                  90                  95

Tyr Cys Val Gly Gly Gly Asp Phe Trp Gly Gln Gly Thr Leu Val Thr
            100                 105                 110

Val Ser Ser
        115

<210> SEQ ID NO 112
<211> LENGTH: 115
<212> TYPE: PRT
<213> ORGANISM: Artificial Sequence
<220> FEATURE:
```

<223> OTHER INFORMATION: heavy chain

<400> SEQUENCE: 112

Leu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Ser Asn Asn Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asp Ser Leu Lys Thr Glu Asp Thr Ala Val Tyr
                85                  90                  95

Tyr Cys Val Gly Gly Asp Phe Trp Gly Gln Gly Thr Leu Val Thr
            100                 105                 110

Val Ser Ser
        115

<210> SEQ ID NO 113
<211> LENGTH: 115
<212> TYPE: PRT
<213> ORGANISM: Artificial Sequence
<220> FEATURE:
<223> OTHER INFORMATION: heavy chain

<400> SEQUENCE: 113

Leu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met His Trp Val Arg Gln Ala Ser Gly Lys Gly Leu Glu Trp Val
        35                  40                  45

Ala Arg Ile Arg Ser Lys Ser Asn Asn Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asp Ser Leu Lys Thr Glu Asp Thr Ala Val Tyr
                85                  90                  95

Tyr Cys Val Gly Gly Asp Phe Trp Gly Gln Gly Thr Leu Val Thr
            100                 105                 110

Val Ser Ser
        115

<210> SEQ ID NO 114
<211> LENGTH: 115
<212> TYPE: PRT
<213> ORGANISM: Artificial Sequence
<220> FEATURE:
<223> OTHER INFORMATION: heany chain

<400> SEQUENCE: 114

Leu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met His Trp Val Arg Gln Ala Ser Gly Lys Gly Leu Glu Trp Val

-continued

```
                35                  40                  45
Gly Arg Ile Arg Ser Lys Ser Asn Asn Tyr Ala Thr Tyr Tyr Ala Ala
         50                  55                  60
Ser Val Lys Gly Arg Phe Thr Ile Ser Arg Asp Asp Ser Lys Asn Thr
 65                  70                  75                  80
Ala Tyr Leu Gln Met Asp Ser Leu Lys Thr Glu Asp Thr Ala Val Tyr
                 85                  90                  95
Tyr Cys Val Gly Gly Asp Phe Trp Gly Gln Gly Thr Leu Val Thr
             100                 105                 110
Val Ser Ser
        115

<210> SEQ ID NO 115
<211> LENGTH: 115
<212> TYPE: PRT
<213> ORGANISM: Artificial Sequence
<220> FEATURE:
<223> OTHER INFORMATION: heavy chain

<400> SEQUENCE: 115

Leu Val Gln Leu Val Glu Ser Gly Gly Gly Leu Val Gln Pro Gly Gly
 1               5                  10                  15
Ser Leu Lys Leu Ser Cys Ala Ala Ser Gly Phe Thr Phe Asn Thr Tyr
                 20                  25                  30
Ala Met His Trp Val Arg Gln Ala Ser Gly Lys Gly Leu Glu Trp Val
             35                  40                  45
Gly Arg Ile Arg Ser Lys Ser Asn Asn Tyr Ala Thr Ala Tyr Ala Asp
         50                  55                  60
Ser Val Lys Gly Arg Phe Thr Ile Ser Arg Asp Asp Ser Lys Asn Thr
 65                  70                  75                  80
Ala Tyr Leu Gln Met Asp Ser Leu Lys Thr Glu Asp Thr Ala Val Tyr
                 85                  90                  95
Tyr Cys Val Gly Gly Asp Phe Trp Gly Gln Gly Thr Leu Val Thr
             100                 105                 110
Val Ser Ser
        115

<210> SEQ ID NO 116
<211> LENGTH: 115
<212> TYPE: PRT
<213> ORGANISM: Artificial Sequence
<220> FEATURE:
<223> OTHER INFORMATION: heavy chain

<400> SEQUENCE: 116

Leu Val Gln Leu Val Glu Ser Gly Gly Gly Leu Val Gln Pro Gly Gly
 1               5                  10                  15
Ser Leu Lys Leu Ser Cys Ala Ala Ser Gly Phe Thr Phe Asn Thr Tyr
                 20                  25                  30
Ala Met His Trp Val Arg Gln Ala Ser Gly Lys Gly Leu Glu Trp Val
             35                  40                  45
Gly Arg Ile Arg Ser Lys Ser Asn Asn Tyr Ala Thr Ala Tyr Ala Ala
         50                  55                  60
Ser Val Lys Gly Arg Phe Thr Ile Ser Arg Asp Asp Ser Lys Ser Thr
 65                  70                  75                  80
Ala Tyr Leu Gln Met Asp Ser Leu Lys Thr Glu Asp Thr Ala Val Tyr
                 85                  90                  95
```

Tyr Cys Val Gly Gly Gly Asp Phe Trp Gly Gln Gly Thr Leu Val Thr
            100                 105                 110

Val Ser Ser
        115

<210> SEQ ID NO 117
<211> LENGTH: 115
<212> TYPE: PRT
<213> ORGANISM: Artificial Sequence
<220> FEATURE:
<223> OTHER INFORMATION: heavy chain

<400> SEQUENCE: 117

Leu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met His Trp Val Arg Gln Ala Ser Gly Lys Gly Leu Glu Trp Val
        35                  40                  45

Gly Arg Ile Arg Ser Lys Ser Asn Asn Tyr Ala Thr Ala Tyr Ala Ala
    50                  55                  60

Ser Val Lys Gly Arg Phe Thr Ile Ser Arg Asp Asp Ser Lys Asn Met
65                  70                  75                  80

Ala Tyr Leu Gln Met Asp Ser Leu Lys Thr Glu Asp Thr Ala Val Tyr
                85                  90                  95

Tyr Cys Val Gly Gly Gly Asp Phe Trp Gly Gln Gly Thr Leu Val Thr
            100                 105                 110

Val Ser Ser
        115

<210> SEQ ID NO 118
<211> LENGTH: 115
<212> TYPE: PRT
<213> ORGANISM: Artificial Sequence
<220> FEATURE:
<223> OTHER INFORMATION: heavy chain

<400> SEQUENCE: 118

Leu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met His Trp Val Arg Gln Ala Ser Gly Lys Gly Leu Glu Trp Val
        35                  40                  45

Gly Arg Ile Arg Ser Lys Ser Asn Asn Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Val Tyr Leu Gln Met Asp Ser Leu Lys Thr Glu Asp Thr Ala Val Tyr
                85                  90                  95

Tyr Cys Val Gly Gly Gly Asp Phe Trp Gly Gln Gly Thr Leu Val Thr
            100                 105                 110

Val Ser Ser
        115

<210> SEQ ID NO 119
<211> LENGTH: 115
<212> TYPE: PRT
<213> ORGANISM: Artificial Sequence
<220> FEATURE:
<223> OTHER INFORMATION: heavy chain

<400> SEQUENCE: 119

Leu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Ala Arg Ile Arg Ser Lys Ser Asn Asn Tyr Ala Thr Tyr Tyr Ala Ala
    50                  55                  60

Ser Val Lys Gly Arg Phe Thr Ile Ser Arg Asp Asp Ser Lys Ser Met
65                  70                  75                  80

Ala Tyr Leu Gln Met Asp Ser Leu Lys Thr Glu Asp Thr Ala Val Tyr
                85                  90                  95

Tyr Cys Val Gly Gly Gly Asp Phe Trp Gly Gln Gly Thr Leu Val Thr
            100                 105                 110

Val Ser Ser
        115

<210> SEQ ID NO 120
<211> LENGTH: 115
<212> TYPE: PRT
<213> ORGANISM: Artificial Sequence
<220> FEATURE:
<223> OTHER INFORMATION: heavy chain

<400> SEQUENCE: 120

Leu Val Gln Val Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Ser Asn Asn Tyr Ala Thr Tyr Tyr Ala Ala
    50                  55                  60

Ser Val Lys Gly Arg Phe Thr Ile Ser Arg Asp Asp Ser Lys Ser Met
65                  70                  75                  80

Ala Tyr Leu Gln Met Asp Ser Leu Lys Thr Glu Asp Thr Ala Val Tyr
                85                  90                  95

Tyr Cys Val Gly Gly Gly Asp Phe Trp Gly Gln Gly Thr Leu Val Thr
            100                 105                 110

Val Ser Ser
        115

<210> SEQ ID NO 121
<211> LENGTH: 115
<212> TYPE: PRT
<213> ORGANISM: Artificial Sequence
<220> FEATURE:
<223> OTHER INFORMATION: heavy chain

<400> SEQUENCE: 121

Leu Val Gln Val Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

```
Ala Met Asn Trp Val Arg Gln Ala Ser Gly Lys Gly Leu Glu Trp Val
            35                  40                  45
Ala Arg Ile Arg Ser Lys Ser Asn Asn Tyr Ala Thr Tyr Tyr Ala Ala
 50                  55                  60
Ser Val Lys Gly Arg Phe Thr Ile Ser Arg Asp Asp Ser Lys Ser Met
 65                  70                  75                  80
Ala Tyr Leu Gln Met Asp Ser Leu Lys Thr Glu Asp Thr Ala Val Tyr
                 85                  90                  95
Tyr Cys Val Gly Gly Gly Asp Phe Trp Gly Gln Gly Thr Leu Val Thr
                100                 105                 110
Val Ser Ser
        115

<210> SEQ ID NO 122
<211> LENGTH: 107
<212> TYPE: PRT
<213> ORGANISM: Artificial Sequence
<220> FEATURE:
<223> OTHER INFORMATION: light chain

<400> SEQUENCE: 122

Asp Ile Gln Met Thr Gln Ser Pro Ser Ser Leu Ser Ala Ser Leu Gly
  1               5                  10                  15
Glu Arg Val Ser Leu Thr Cys Arg Ala Ser Gln Glu Ile Ser Val Tyr
                 20                  25                  30
Leu Ser Trp Phe Gln Gln Lys Pro Asp Gly Thr Ile Lys Arg Leu Ile
             35                  40                  45
Tyr Gly Ala Phe Thr Leu Asp Ser Gly Val Pro Lys Arg Phe Ser Gly
 50                  55                  60
Ser Arg Ser Gly Ser Asp Tyr Ser Leu Thr Ile Ser Ser Leu Glu Ser
 65                  70                  75                  80
Glu Asp Phe Ala Asp Tyr Tyr Cys Leu Gln Tyr Val Arg Tyr Pro Trp
                 85                  90                  95
Thr Phe Gly Gly Gly Thr Lys Leu Glu Ile Lys
                100                 105

<210> SEQ ID NO 123
<211> LENGTH: 107
<212> TYPE: PRT
<213> ORGANISM: Artificial Sequence
<220> FEATURE:
<223> OTHER INFORMATION: light chain

<400> SEQUENCE: 123

Asp Ile Gln Met Thr Gln Ser Pro Ser Ser Leu Ser Ala Ser Val Gly
  1               5                  10                  15
Asp Arg Val Thr Ile Thr Cys Arg Ala Ser Gln Glu Ile Ser Val Tyr
                 20                  25                  30
Leu Gly Trp Tyr Gln Gln Lys Pro Gly Lys Ala Pro Lys Arg Leu Ile
             35                  40                  45
Tyr Gly Ala Phe Lys Leu Gln Ser Gly Val Pro Ser Arg Phe Ser Gly
 50                  55                  60
Ser Arg Ser Gly Thr Glu Phe Thr Leu Thr Ile Ser Ser Leu Gln Pro
 65                  70                  75                  80
Glu Asp Phe Ala Thr Tyr Tyr Cys Leu Gln Tyr Val Arg Tyr Pro Trp
                 85                  90                  95
Thr Phe Gly Gly Gly Thr Lys Val Glu Ile Lys
                100                 105
```

<210> SEQ ID NO 124
<211> LENGTH: 107
<212> TYPE: PRT
<213> ORGANISM: Artificial Sequence
<220> FEATURE:
<223> OTHER INFORMATION: light chain

<400> SEQUENCE: 124

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
            20                  25                  30

Leu Gly Trp Tyr Gln Gln Lys Pro Gly Lys Ala Pro Lys Arg Leu Ile
        35                  40                  45

Tyr Gly Ala Phe Lys Leu Gln Ser Gly Val Pro Ser Arg Phe Ser Gly
50                  55                  60

Ser Arg Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Val Arg Tyr Pro Trp
                85                  90                  95

Thr Phe Gly Gly Gly Thr Lys Val Glu Ile Lys
            100                 105
```

<210> SEQ ID NO 125
<211> LENGTH: 107
<212> TYPE: PRT
<213> ORGANISM: Artificial Sequence
<220> FEATURE:
<223> OTHER INFORMATION: light chain

<400> SEQUENCE: 125

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
            20                  25                  30

Leu Ser Trp Phe Gln Gln Lys Pro Gly Lys Ala Ile Lys Arg Leu Ile
        35                  40                  45

Tyr Gly Ala Phe Thr Leu Gln Ser Gly Val Pro Ser Arg Phe Ser Gly
50                  55                  60

Ser Arg Ser Gly Ser Glu Tyr Thr Leu Thr Ile Ser Ser Leu Gln Pro
65                  70                  75                  80

Glu Asp Phe Ala Thr Tyr Tyr Cys Leu Gln Tyr Val Arg Tyr Pro Trp
                85                  90                  95

Thr Phe Gly Gly Gly Thr Lys Val Glu Ile Lys
            100                 105
```

<210> SEQ ID NO 126
<211> LENGTH: 107
<212> TYPE: PRT
<213> ORGANISM: Artificial Sequence
<220> FEATURE:
<223> OTHER INFORMATION: ligh chain

<400> SEQUENCE: 126

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
            20                  25                  30
```

Leu Ser Trp Phe Gln Gln Lys Pro Gly Lys Ala Pro Lys Arg Leu Ile
            35                  40                  45

Tyr Gly Ala Phe Lys Leu Gln Ser Gly Val Pro Ser Arg Phe Ser Gly
    50                  55                  60

Ser Arg Ser Gly Thr Glu Tyr Thr Leu Thr Ile Ser Ser Leu Gln Pro
65                  70                  75                  80

Glu Asp Phe Ala Thr Tyr Tyr Cys Leu Gln Tyr Val Arg Tyr Pro Trp
                85                  90                  95

Thr Phe Gly Gly Gly Thr Lys Val Glu Ile Lys
                100                 105

<210> SEQ ID NO 127
<211> LENGTH: 107
<212> TYPE: PRT
<213> ORGANISM: Artificial Sequence
<220> FEATURE:
<223> OTHER INFORMATION: light chain

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
            20                  25                  30

Leu Ser Trp Tyr Gln Gln Lys Pro Gly Lys Ala Pro Lys Arg Leu Ile
            35                  40                  45

Tyr Gly Ala Phe Lys Leu Gln Ser Gly Val Pro Ser Arg Phe Ser Gly
    50                  55                  60

Ser Arg Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Val Arg Tyr Pro Trp
                85                  90                  95

Thr Phe Gly Gly Gly Thr Lys Val Glu Ile Lys
                100                 105

<210> SEQ ID NO 128
<211> LENGTH: 107
<212> TYPE: PRT
<213> ORGANISM: Artificial Sequence
<220> FEATURE:
<223> OTHER INFORMATION: light chain

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
            20                  25                  30

Leu Gly Trp Phe Gln Gln Lys Pro Gly Lys Ala Pro Lys Arg Leu Ile
            35                  40                  45

Tyr Gly Ala Phe Lys Leu Gln Ser Gly Val Pro Ser Arg Phe Ser Gly
    50                  55                  60

Ser Arg Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Val Arg Tyr Pro Trp
                85                  90                  95

Thr Phe Gly Gly Gly Thr Lys Val Glu Ile Lys
                100                 105

<210> SEQ ID NO 129

<211> LENGTH: 107
<212> TYPE: PRT
<213> ORGANISM: Artificial Sequence
<220> FEATURE:
<223> OTHER INFORMATION: light chain

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
            20                  25                  30

Leu Gly Trp Tyr Gln Gln Lys Pro Gly Lys Ala Ile Lys Arg Leu Ile
        35                  40                  45

Tyr Gly Ala Phe Lys Leu Gln Ser Gly Val Pro Ser Arg Phe Ser Gly
    50                  55                  60

Ser Arg Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Val Arg Tyr Pro Trp
                85                  90                  95

Thr Phe Gly Gly Gly Thr Lys Val Glu Ile Lys
            100                 105

<210> SEQ ID NO 130
<211> LENGTH: 107
<212> TYPE: PRT
<213> ORGANISM: Artificial Sequence
<220> FEATURE:
<223> OTHER INFORMATION: light chain

<400> SEQUENCE: 130

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
            20                  25                  30

Leu Gly Trp Tyr Gln Gln Lys Pro Gly Lys Ala Pro Lys Arg Leu Ile
        35                  40                  45

Tyr Gly Ala Phe Thr Leu Gln Ser Gly Val Pro Ser Arg Phe Ser Gly
    50                  55                  60

Ser Arg Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Val Arg Tyr Pro Trp
                85                  90                  95

Thr Phe Gly Gly Gly Thr Lys Val Glu Ile Lys
            100                 105

<210> SEQ ID NO 131
<211> LENGTH: 107
<212> TYPE: PRT
<213> ORGANISM: Artificial Sequence
<220> FEATURE:
<223> OTHER INFORMATION: light chain

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
            20                  25                  30

Leu Gly Trp Tyr Gln Gln Lys Pro Gly Lys Ala Pro Lys Arg Leu Ile
        35                  40                  45

Tyr Gly Ala Phe Lys Leu Gln Ser Gly Val Pro Ser Arg Phe Ser Gly
            50                  55                  60

Ser Arg Ser Gly Ser Glu Phe Thr Leu Thr Ile Ser Ser Leu Gln Pro
65                  70                  75                  80

Glu Asp Phe Ala Thr Tyr Tyr Cys Leu Gln Tyr Val Arg Tyr Pro Trp
                85                  90                  95

Thr Phe Gly Gly Gly Thr Lys Val Glu Ile Lys
            100                 105

<210> SEQ ID NO 132
<211> LENGTH: 107
<212> TYPE: PRT
<213> ORGANISM: Artificial Sequence
<220> FEATURE:
<223> OTHER INFORMATION: light chain

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
                20                  25                  30

Leu Gly Trp Tyr Gln Gln Lys Pro Gly Lys Ala Pro Lys Arg Leu Ile
            35                  40                  45

Tyr Gly Ala Phe Lys Leu Gln Ser Gly Val Pro Ser Arg Phe Ser Gly
    50                  55                  60

Ser Arg Ser Gly Thr Glu Tyr Thr Leu Thr Ile Ser Ser Leu Gln Pro
65                  70                  75                  80

Glu Asp Phe Ala Thr Tyr Tyr Cys Leu Gln Tyr Val Arg Tyr Pro Trp
                85                  90                  95

Thr Phe Gly Gly Gly Thr Lys Val Glu Ile Lys
            100                 105

<210> SEQ ID NO 133
<211> LENGTH: 107
<212> TYPE: PRT
<213> ORGANISM: Artificial Sequence
<220> FEATURE:
<223> OTHER INFORMATION: light chain

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
                20                  25                  30

Leu Gly Trp Tyr Gln Gln Lys Pro Gly Lys Ala Pro Lys Arg Leu Ile
            35                  40                  45

Tyr Gly Ala Phe Ser Leu Gln Ser Gly Val Pro Ser Arg Phe Ser Gly
    50                  55                  60

Ser Arg Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Val Arg Tyr Pro Trp
                85                  90                  95

Thr Phe Gly Gly Gly Thr Lys Val Glu Ile Lys
            100                 105

<210> SEQ ID NO 134
<211> LENGTH: 107
<212> TYPE: PRT
<213> ORGANISM: Artificial Sequence
<220> FEATURE:
<223> OTHER INFORMATION: light chain

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
            20                  25                  30

Leu Ser Trp Phe Gln Gln Lys Pro Gly Lys Ala Ile Lys Arg Leu Ile
        35                  40                  45

Tyr Gly Ala Phe Lys Leu Gln Ser Gly Val Pro Ser Arg Phe Ser Gly
    50                  55                  60

Ser Arg Ser Gly Thr Glu Tyr Thr Leu Thr Ile Ser Ser Leu Gln Pro
65                  70                  75                  80

Glu Asp Phe Ala Thr Tyr Tyr Cys Leu Gln Tyr Val Arg Tyr Pro Trp
                85                  90                  95

Thr Phe Gly Gly Gly Thr Lys Val Glu Ile Lys
            100                 105

<210> SEQ ID NO 135
<211> LENGTH: 107
<212> TYPE: PRT
<213> ORGANISM: Artificial Sequence
<220> FEATURE:
<223> OTHER INFORMATION: light chain

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
            20                  25                  30

Leu Ser Trp Phe Gln Gln Lys Pro Gly Lys Ala Ile Lys Arg Leu Ile
        35                  40                  45

Tyr Gly Ala Phe Ser Leu Gln Ser Gly Val Pro Ser Arg Phe Ser Gly
    50                  55                  60

Ser Arg Ser Gly Thr Glu Tyr Thr Leu Thr Ile Ser Ser Leu Gln Pro
65                  70                  75                  80

Glu Asp Phe Ala Thr Tyr Tyr Cys Leu Gln Tyr Val Arg Tyr Pro Trp
                85                  90                  95

Thr Phe Gly Gly Gly Thr Lys Val Glu Ile Lys
            100                 105

<210> SEQ ID NO 136
<211> LENGTH: 107
<212> TYPE: PRT
<213> ORGANISM: Artificial Sequence
<220> FEATURE:
<223> OTHER INFORMATION: light chain

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
            20                  25                  30

Leu Gly Trp Tyr Gln Gln Lys Pro Gly Lys Ala Pro Lys Arg Leu Ile
        35                  40                  45

Tyr Gly Ala Phe Thr Leu Gln Ser Gly Val Pro Ser Arg Phe Ser Gly
    50                  55                  60

```
Ser Arg Ser Gly Thr Glu Tyr Thr Leu Thr Ile Ser Ser Leu Gln Pro
 65                  70                  75                  80

Glu Asp Phe Ala Thr Tyr Tyr Cys Leu Gln Tyr Val Arg Tyr Pro Trp
                 85                  90                  95

Thr Phe Gly Gly Gly Thr Lys Val Glu Ile Lys
            100                 105

<210> SEQ ID NO 137
<211> LENGTH: 107
<212> TYPE: PRT
<213> ORGANISM: Artificial Sequence
<220> FEATURE:
<223> OTHER INFORMATION: light chain

<400> SEQUENCE: 137

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Glu Ile Ser Val Tyr
                 20                  25                  30

Leu Gly Trp Tyr Gln Gln Lys Pro Gly Lys Ala Pro Lys Arg Leu Ile
             35                  40                  45

Tyr Gly Ala Phe Ser Leu Gln Ser Gly Val Pro Ser Arg Phe Ser Gly
 50                  55                  60

Ser Arg Ser Gly Thr Glu Tyr Thr Leu Thr Ile Ser Ser Leu Gln Pro
 65                  70                  75                  80

Glu Asp Phe Ala Thr Tyr Tyr Cys Leu Gln Tyr Val Arg Tyr Pro Trp
                 85                  90                  95

Thr Phe Gly Gly Gly Thr Lys Val Glu Ile Lys
            100                 105

<210> SEQ ID NO 138
<211> LENGTH: 107
<212> TYPE: PRT
<213> ORGANISM: Artificial Sequence
<220> FEATURE:
<223> OTHER INFORMATION: light chain

<400> SEQUENCE: 138

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Glu Ile Ser Val Tyr
                 20                  25                  30

Leu Gly Trp Phe Gln Gln Lys Pro Gly Lys Ala Pro Lys Arg Leu Ile
             35                  40                  45

Tyr Gly Ala Phe Lys Leu Gln Ser Gly Val Pro Ser Arg Phe Ser Gly
 50                  55                  60

Ser Arg Ser Gly Thr Glu Tyr Thr Leu Thr Ile Ser Ser Leu Gln Pro
 65                  70                  75                  80

Glu Asp Phe Ala Thr Tyr Tyr Cys Leu Gln Tyr Val Arg Tyr Pro Trp
                 85                  90                  95

Thr Phe Gly Gly Gly Thr Lys Val Glu Ile Lys
            100                 105

<210> SEQ ID NO 139
<211> LENGTH: 41
<212> TYPE: DNA
<213> ORGANISM: Artificial Sequence
<220> FEATURE:
<223> OTHER INFORMATION: primer
```

<400> SEQUENCE: 139
tgtaaaacga cggccagtga ggtgcaggtt gttgagtctg g        41

<210> SEQ ID NO 140
<211> LENGTH: 43
<212> TYPE: DNA
<213> ORGANISM: Artificial Sequence
<220> FEATURE:
<223> OTHER INFORMATION: primer

<400> SEQUENCE: 140
tgtaaaacga cggccagtat gacattgaac atgctgttgg ggc       43

<210> SEQ ID NO 141
<211> LENGTH: 33
<212> TYPE: DNA
<213> ORGANISM: Artificial Sequence
<220> FEATURE:
<223> OTHER INFORMATION: primer

<400> SEQUENCE: 141
gatctccgtg tacctgagct ggtatcagca gaa              33

<210> SEQ ID NO 142
<211> LENGTH: 321
<212> TYPE: DNA
<213> ORGANISM: Artificial Sequence
<220> FEATURE:
<223> OTHER INFORMATION: MoTau01_VK

<400> SEQUENCE: 142
gacatccaga tgacccagtc tccatcctcc ttatctgcct ctctgggaga aagagtcagt    60
ctcacttgtc gggcaagtca ggaaattagt gtttacttaa gctggtttca gcagaaacca   120
gatggaacta ttaaacgcct gatctacggc gcattcactt tagattctgg tgtcccaaaa   180
aggttcagtg gcagtaggtc tgggtcagat tattctctca ccatcagcag ccttgagtct   240
gaagattttg cagactatta ctgtctacaa tatgttaggt atccgtggac gttcggtgga   300
ggcaccaagt tggaaatcaa a                                             321

<210> SEQ ID NO 143
<211> LENGTH: 345
<212> TYPE: DNA
<213> ORGANISM: Artificial Sequence
<220> FEATURE:
<223> OTHER INFORMATION: MoTau01_VH

<400> SEQUENCE: 143
gaggtgcagg ttgttgagtc tgtggaggga ttggtgcagc ctaaagggtc attgaaactc    60
tcatgtgcag cctctggatt caccttcaat acctacgcca tgaactgggt ccgccaggct   120
ccaggaaagg gtttggaatg ggttgctcgc ataagaagta aaagtaataa ttatgcgaca   180
tattatgccg attcagtgaa agacaggttc accatctcca gagatgattc acaaagcatg   240
gtatatctgc aaatgaacaa cttgaaaact gaggacacag ccatgtatta ttgtgtggga   300
gggggtgact ctggggccaa ggcaccgctc tcacagtct cctca                    345

<210> SEQ ID NO 144
<211> LENGTH: 440
<212> TYPE: DNA
<213> ORGANISM: Artificial Sequence
<220> FEATURE:
<223> OTHER INFORMATION: MoTau01 VK

<400> SEQUENCE: 144

```
tccttgacac gcgtctcggg aagcttgccg ccaccatgga agccccagcg cagcttctct      60
tcctcctgct actctggctc cctgatacca ccggagatat ccagatgaca cagtctcctt     120
ctagcctgtc cgcctctctg ggagagaggg tgtccctgac tgtagagca tcccaggaga      180
tcagcgtgta cctgagctgg tttcagcaga agcccgacgg caccatcaag aggctgatct     240
atggcgcctt cacactggat tctggcgtgc ctaagcggtt tagcggctcc agatctggca     300
gcgactactc cctgacaatc tctagcctgg agtctgagga cttcgccgat tactattgcc     360
tgcagtacgt gagatatccc tggaccttcg gcggcggcac aaagctggag atcaagagaa     420
ctgtggcagc accaagcgtc                                                 440
```

<210> SEQ ID NO 145
<211> LENGTH: 135
<212> TYPE: PRT
<213> ORGANISM: Artificial Sequence
<220> FEATURE:
<223> OTHER INFORMATION: MoTau01 VK

<400> SEQUENCE: 145

```
Met Glu Ala Pro Ala Gln Leu Leu Phe Leu Leu Leu Trp Leu Pro
1               5                   10                  15
Asp Thr Thr Gly Asp Ile Gln Met Thr Gln Ser Pro Ser Ser Leu Ser
            20                  25                  30
Ala Ser Leu Gly Glu Arg Val Ser Leu Thr Cys Arg Ala Ser Gln Glu
        35                  40                  45
Ile Ser Val Tyr Leu Ser Trp Phe Gln Gln Lys Pro Asp Gly Thr Ile
    50                  55                  60
Lys Arg Leu Ile Tyr Gly Ala Phe Thr Leu Asp Ser Gly Val Pro Lys
65                  70                  75                  80
Arg Phe Ser Gly Ser Arg Ser Gly Ser Asp Tyr Ser Leu Thr Ile Ser
                85                  90                  95
Ser Leu Glu Ser Glu Asp Phe Ala Asp Tyr Tyr Cys Leu Gln Tyr Val
            100                 105                 110
Arg Tyr Pro Trp Thr Phe Gly Gly Gly Thr Lys Leu Glu Ile Lys Arg
        115                 120                 125
Thr Val Ala Ala Pro Ser Val
    130                 135
```

<210> SEQ ID NO 146
<211> LENGTH: 551
<212> TYPE: DNA
<213> ORGANISM: Artificial Sequence
<220> FEATURE:
<223> OTHER INFORMATION: MoTau01VH codon optimised

<400> SEQUENCE: 146

```
tccttgacac gcgtctcggg aagcttgccg ccaccatgga agccccagcg cagcttctct      60
tcctcctgct actctggctc cctgatacca ccggagaggt gcaggtggtg gagagcggcg     120
gcggcctggt gcagcccaag ggcagcctga agctgtcctg tgccgcctct ggcttcacct     180
ttaacacata tgccatgaat tgggtgcggc aggcacctgg caagggactg gagtgggtgg     240
caagaatcag atctaagagc aacaattacg ccacctacta tgccgacagc gtgaaggata     300
ggttcacaat ctcccgcgac gattcccagt ctatggtgta tctgcagatg aacaattctg     360
aagaccgagg acacagccat gtactattgc gtgggcggcg gcgacttttg gggacagggc     420
```
accgccctga cagtgagctc cgcctccacc aagggcccat ccgtcttccc cctggcgccc    480
tgctccagga gcacctccga gagcacagcc gccctgggct gcctggtcaa ggactacttc    540
cccgaaccgg t    551

```
<210> SEQ ID NO 147
<211> LENGTH: 172
<212> TYPE: PRT
<213> ORGANISM: Artificial Sequence
<220> FEATURE:
<223> OTHER INFORMATION: MoTau01 VH codon opimised
```

<400> SEQUENCE: 147

Met Glu Ala Pro Ala Gln Leu Leu Phe Leu Leu Leu Trp Leu Pro
1               5                   10                  15

Asp Thr Thr Gly Glu Val Gln Val Val Glu Ser Gly Gly Gly Leu Val
            20                  25                  30

Gln Pro Lys Gly Ser Leu Lys Leu Ser Cys Ala Ala Ser Gly Phe Thr
        35                  40                  45

Phe Asn Thr Tyr Ala Met Asn Trp Val Arg Gln Ala Pro Gly Lys Gly
    50                  55                  60

Leu Glu Trp Val Ala Arg Ile Arg Ser Lys Ser Asn Asn Tyr Ala Thr
65                  70                  75                  80

Tyr Tyr Ala Asp Ser Val Lys Asp Arg Phe Thr Ile Ser Arg Asp Asp
                85                  90                  95

Ser Gln Ser Met Val Tyr Leu Gln Met Asn Asn Leu Lys Thr Glu Asp
            100                 105                 110

Thr Ala Met Tyr Tyr Cys Val Gly Gly Gly Asp Phe Trp Gly Gln Gly
        115                 120                 125

Thr Ala Leu Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val
                165                 170

```
<210> SEQ ID NO 148
<211> LENGTH: 345
<212> TYPE: DNA
<213> ORGANISM: Artificial Sequence
<220> FEATURE:
<223> OTHER INFORMATION: Tau01 HA
```

<400> SEQUENCE: 148
ctggtgcagc tggtggaaag cggcggcggc ctggtgcagc ctggcggctc cctgaagctg    60
tcttgtgcag caagcggctt cacctttaac acatatgcaa tgcactgggt gcggcaggca    120
tctggcaagg gactggagtg ggtgggccgg atcagatcta agagcaacaa ttatgcaaca    180
gcatatgcag catctgtgaa gggcaggttc accatctccc gcgacgattc taagaataca    240
gcctatctgc agatggactc cctgaagacc gaggatacag ccgtgtacta ttgcgtgggc    300
ggcggcgact ttggggaca gggcaccctg gtgacagtga gctcc    345

```
<210> SEQ ID NO 149
<211> LENGTH: 345
<212> TYPE: DNA
<213> ORGANISM: Artificial Sequence
<220> FEATURE:
<223> OTHER INFORMATION: Tau01 HB
```

<400> SEQUENCE: 149

```
gaggtgcagg tggtggaaag cggcggcggc ctggtgcagc tggcggcag cctgaagctg    60 tcctgtgcag catctggctt cacctttaac acatacgcca tgaattgggt gcggcaggca   120
tctggcaagg gactggagtg ggtggcccgg atcagatcta agagcaacaa ttacgccacc   180
tactatgccg acagcgtgaa gggcaggttc acaatctccc gcgacgattc caagtctatg   240
gtgtatctgc agatggactc cctgaagacc gaggatacag ccgtgtacta ttgcgtgggc   300
ggcggcgact tttggggaca gggcaccctg gtgacagtga gctcc                   345
```

<210> SEQ ID NO 150  
<211> LENGTH: 345  
<212> TYPE: DNA  
<213> ORGANISM: Artificial Sequence  
<220> FEATURE:  
<223> OTHER INFORMATION: Tau01 HC

<400> SEQUENCE: 150

```
ctggtgcagc tggtggaaag cggcggcggc ctggtgcagc tggcggcag cctgaagctg    60 tcctgtgcag catctggctt cacctttaac acatacgcca tgaattgggt gcggcaggca   120
tctggcaagg gactggagtg ggtggcccgg atcagatcta agagcaacaa ttacgccacc   180
tactatgccg ccagcgtgaa gggcaggttc acaatctccc gcgacgattc caagtctatg   240
gcctatctgc agatggactc cctgaagacc gaggatacag ccgtgtacta ttgcgtgggc   300
ggcggcgact tttggggaca gggcaccctg gtgacagtga gctcc                   345
```

<210> SEQ ID NO 151  
<211> LENGTH: 321  
<212> TYPE: DNA  
<213> ORGANISM: Artificial Sequence  
<220> FEATURE:  
<223> OTHER INFORMATION: Tau01 KA

<400> SEQUENCE: 151

```
gacatccaga tgacccagtc tccaagctcc ctgtccgcct ctgtgggcga tagggtgacc    60
atcacatgcc gcgccagcca ggagatctcc gtgtacctgg ctggtatca gcagaagccc   120 ggcaaggccc ctaagcggct gatctacggc gccttcaagc tgcagtccgg agtgccaagc   180
cggttcagcg gatccagatc tggcaccgag tttaccctga caatctctag cctgcagcca   240
gaggacttcg ccacatacta ttgtctgcag tacgtgaggt atccctggac cttcggcggc   300
ggcacaaagg tggagatcaa g                                             321
```

<210> SEQ ID NO 152  
<211> LENGTH: 321  
<212> TYPE: DNA  
<213> ORGANISM: Artificial Sequence  
<220> FEATURE:  
<223> OTHER INFORMATION: Tau01 KB

<400> SEQUENCE: 152

```
gacatccaga tgacacagtc tcctagctcc ctgtccgcct ctgtgggcga tagggtgacc    60
atcacatgcc gcgcctccca ggagatcagc gtgtacctga ctggttcca gcagaagcca   120 ggcaaggcca tcaagcggct gatctatgga gccttcaccc tgcagtctgg agtgccatct   180
cggtttagcg gctccagatc tggcagcgag tacaccctga caatctctag cctgcagccc   240
gaggacttcg ccacatacta ttgtctgcag tacgtgaggt atccttggac cttcggcggc   300
```

```
ggcacaaagg tggagatcaa g                                          321

<210> SEQ ID NO 153
<211> LENGTH: 321
<212> TYPE: DNA
<213> ORGANISM: Artificial Sequence
<220> FEATURE:
<223> OTHER INFORMATION: Tau01 KC

<400> SEQUENCE: 153
gacatccaga tgacccagtc tcctagctcc ctgtccgcct ctgtgggcga tagggtgacc     60
atcacatgcc gcgccagcca ggagatctcc gtgtacctgt cttggttcca gcagaagccc    120
ggcaaggccc ctaagcggct gatctatgga gccttcaagc tgcagtctgg agtgccatcc    180
cggtttagcg gatccagatc tggcaccgag tacaccctga caatctctag cctgcagcca    240
gaggacttcg ccacatacta ttgtctgcag tacgtgaggt atccctggac cttcggcggc    300
ggcacaaagg tggagatcaa g                                              321
```